US010906987B2

(12) United States Patent
Mandelboim et al.

(10) Patent No.: US 10,906,987 B2
(45) Date of Patent: Feb. 2, 2021

(54) ANTIBODIES SPECIFIC TO HUMAN POLIOVIRUS RECEPTOR (PVR)

(71) Applicants: Yissum Research Development Company of the Hebrew University of Jerusalem Ltd., Jerusalem (IL); University of Rijeka Faculty of Medicine, Rijeka (HR)

(72) Inventors: Ofer Mandelboim, Shoham (IL); Noa S. Kaynan, Kibbutz Barkai (IL); Pinchas Tsukerman, Jerusalem (IL); Stipan Jonjic, Rijeka (HR)

(73) Assignees: YISSUM RESEARCH DEVELOPMENT COMPANY OF THE HEBREW UNIVERSITY OF JERUSALEM LTD., Jerusalem (IL); UNIVERSITY OF RUEKA FACULTY OF MEDICINE RIJEKA, CROATIA, Rueka (CW)

( * ) Notice: Subject to any disclaimer, the term of this patent is extended or adjusted under 35 U.S.C. 154(b) by 214 days.

(21) Appl. No.: 16/081,667

(22) PCT Filed: Feb. 28, 2017

(86) PCT No.: PCT/IL2017/050256
§ 371 (c)(1),
(2) Date: Aug. 31, 2018

(87) PCT Pub. No.: WO2017/149538
PCT Pub. Date: Sep. 8, 2017

(65) Prior Publication Data
US 2020/0040092 A1 Feb. 6, 2020

Related U.S. Application Data

(60) Provisional application No. 62/301,727, filed on Mar. 1, 2016, provisional application No. 62/364,924, filed on Jul. 21, 2016.

(51) Int. Cl.
C07K 16/28 (2006.01)
C07K 16/10 (2006.01)
(Continued)

(52) U.S. Cl.
CPC ....... *C07K 16/2896* (2013.01); *G01N 33/574* (2013.01); *C07K 2317/24* (2013.01);
(Continued)

(58) Field of Classification Search
None
See application file for complete search history.

(56) References Cited

U.S. PATENT DOCUMENTS 3,791,932 A 2/1974 Schuurs
3,839,153 A 10/1974 Schuurs
(Continued)

FOREIGN PATENT DOCUMENTS

EP 0404097 A2 12/1990
RU 2451689 C2 5/2012
(Continued)

OTHER PUBLICATIONS

Nelson et al. Demystified . . . Monoclonal Antibodies. J Clin Pathol: Mol Pathol 2000;53:111-117 (Year: 2000).*
(Continued)

*Primary Examiner* — Michelle S Horning
(74) *Attorney, Agent, or Firm* — Rothwell, Figg, Ernst & Manbeck, P.C.

(57) ABSTRACT

The present invention provides monoclonal antibodies that recognize polio virus receptor (PVR) and inhibit its binding to T cell immunoreceptor with Ig and ITIM domains (TIGIT). The present invention further provides pharmaceu-
(Continued)

tical compositions comprising the antibodies and methods for their use in cancer immunotherapy, treating infections and in diagnosis.

11 Claims, 28 Drawing Sheets

Specification includes a Sequence Listing.

(51) Int. Cl.
    *C07K 14/705* (2006.01)
    *A61K 39/395* (2006.01)
    *G01N 33/574* (2006.01)

(52) U.S. Cl.
    CPC ...... *C07K 2317/30* (2013.01); *C07K 2317/73* (2013.01); *C07K 2317/76* (2013.01); *C07K 2317/92* (2013.01); *G01N 2333/70596* (2013.01)

(56) References Cited

U.S. PATENT DOCUMENTS

| | | | |
|---|---|---|---|
| 3,850,578 | A | 11/1974 | McConnell |
| 3,850,752 | A | 11/1974 | Schuurs |
| 3,853,987 | A | 12/1974 | Dreyer |
| 3,867,517 | A | 2/1975 | Ling |
| 3,879,262 | A | 4/1975 | Schuurs |
| 3,901,654 | A | 8/1975 | Gross |
| 3,935,074 | A | 1/1976 | Rubenstein |
| 3,984,533 | A | 10/1976 | Uzgiris |
| 3,996,345 | A | 12/1976 | Ullman |
| 4,034,074 | A | 7/1977 | Miles |
| 4,036,945 | A | 7/1977 | Haber |
| 4,098,876 | A | 7/1978 | Piasio |
| 4,331,647 | A | 5/1982 | Goldenberg |
| 4,666,828 | A | 5/1987 | Gusella |
| 4,683,202 | A | 7/1987 | Mullis |
| 4,801,531 | A | 1/1989 | Frossard |
| 4,816,567 | A | 3/1989 | Cabilly |
| 4,879,219 | A | 11/1989 | Wands |
| 4,946,778 | A | 8/1990 | Ladner |
| 5,011,771 | A | 4/1991 | Bellet |
| 5,192,659 | A | 3/1993 | Simons |
| 5,225,539 | A | 7/1993 | Winter |
| 5,272,057 | A | 12/1993 | Smulson |
| 5,281,521 | A | 1/1994 | Trojanowski |
| 5,530,101 | A | 6/1996 | Queen |
| 5,545,806 | A | 8/1996 | Lonberg |
| 5,545,807 | A | 8/1996 | Surani |
| 5,569,825 | A | 10/1996 | Lonberg |
| 5,585,089 | A | 12/1996 | Queen |
| 5,625,126 | A | 4/1997 | Lonberg |
| 5,633,425 | A | 5/1997 | Lonberg |
| 5,641,870 | A | 6/1997 | Rinderknecht |
| 5,661,016 | A | 8/1997 | Lonberg |
| 5,693,761 | A | 12/1997 | Queen |
| 5,693,762 | A | 12/1997 | Queen |
| 6,518,033 | B1 | 2/2003 | Gromeier et al. |
| 7,045,605 | B2 | 5/2006 | Bander |
| 7,244,429 | B2 | 7/2007 | Zhou |
| 7,365,167 | B2 | 4/2008 | Watkins |
| 7,709,610 | B2 | 5/2010 | Williams |
| 7,744,874 | B2 | 6/2010 | Korytko |
| 7,785,593 | B2 | 8/2010 | Barske |
| 8,637,643 | B2 | 1/2014 | Latham |
| 8,652,469 | B2 | 2/2014 | Kavanaugh |
| 8,841,418 | B2 | 9/2014 | Karsunky |
| 2005/0153447 | A1 | 7/2005 | Berenson |
| 2007/0041985 | A1 | 2/2007 | Unger |
| 2008/0019974 | A1 | 1/2008 | Kim |
| 2009/0215175 | A1 | 8/2009 | Unger |
| 2009/0258013 | A1 | 10/2009 | Clark |
| 2009/0280128 | A1 | 11/2009 | Kamogawa |
| 2013/0095116 | A1 | 4/2013 | Gurney |
| 2014/0056890 | A1 | 2/2014 | Gurney |
| 2014/0186380 | A1 | 7/2014 | Gurney |
| 2014/0302034 | A1 | 10/2014 | Bankovich |
| 2015/0216970 | A1 | 8/2015 | Grogan |
| 2017/0037133 | A1 | 2/2017 | Fiedler |

FOREIGN PATENT DOCUMENTS

| | | |
|---|---|---|
| WO | 8601533 A1 | 3/1986 |
| WO | 9007861 A1 | 7/1990 |
| WO | 9222653 A1 | 12/1992 |
| WO | 9311161 A1 | 6/1993 |
| WO | 9315210 A1 | 8/1993 |
| WO | 9402610 A1 | 2/1994 |
| WO | 9503832 A1 | 2/1995 |
| WO | 9613583 A2 | 5/1996 |
| WO | 9637621 A2 | 11/1996 |
| WO | WO-2004074324 A2 | 9/2004 |
| WO | 2006124667 A2 | 11/2006 |
| WO | WO-2007072866 A1 | 6/2007 |
| WO | 2014130879 A2 | 8/2014 |
| WO | WO-2015009856 A2 | 1/2015 |
| WO | 2015031693 A1 | 3/2015 |
| WO | 2015051159 A1 | 4/2015 |
| WO | 2015142303 A1 | 9/2015 |
| WO | 2017021526 A1 | 2/2017 |
| WO | WO 2017/149538 A1 | 9/2017 |

OTHER PUBLICATIONS

International Application No. PCT/IL2017/050256 International Preliminary Report on Patentability dated Sep. 4, 2018.
International Application No. PCT/IL2017/050256 International Search Report and Written Opinion dated May 30, 2017.
Stanietsky et al.: The interaction of TIGIT with PVR and PVRL2 inhibits human NK cell cytotoxicity. Proceedings of the National Academy of Sciences. 106(42):17858-17863 (2009).
European Patent Application No. 17713469.9 Examination Report dated Oct. 11, 2019.
Podsypanina et al.: Oncogene cooperation in tumor maintenance and tumor recurrence in mouse mammary tumors induced by Myc and mutant Kras. PNAS. 105(13):5242-5247 (2008).
Refaeli et al.: The B cell antigen receptor and overexpression of MYC can cooperate in the genesis of B cell lymphomas. PLoS Biology. 6(6):1208-1225 (2008).
Refaeli et al.: The protooncogene Myc can break B cell tolerance. PNAS. 102(11):4097-4102 (2005).
Roh et al.: Transgenic Mice for Cre-Inducible Overexpression of the Oncogenes c-MYC and PIM-1 in Multiple Tissues. Genesis. vol. 44:447-453 (2006).
Schmidt et al.: Transgenic mice bearing the human c-myc gene activated by an immunoglobulin enhancer: A pre-B-cell lymphoma model. PNAS. vol. 85:6047-6051 (1988).
Porter (1959) The hydrolysis of rabbit y-globulin and antibodies with crystalline papain. Biochem J 73(1): 119-126.
Presta (1992) Antibody engineering. Current Opinion in Structural Biology 2(4): 593-596. Abstract.
Richardson and Marasco (1995) Intracellular antibodies: development and therapeutic potential. Trends Biotechnol 13(8): 306-310.
Richardson et al., (1995) Phenotypic knockout of the high-affinity human interleukin 2 receptor by intracellular single-chain antibodies against the alpha subunit of the receptor. Proc Natl Acad Sci U S A 92(8): 3137-3141.
Riechmann et al., (1988) Reshaping human antibodies for therapy. Nature 332(6162): 323-327.
Rudikoff et al., (1982) Single amino acid substitution altering antigen-binding specificity. Proc Natl Acad Sci U S A 79(6): 1979-1983.
Sakahara et al., (1985) Effect of DTPA conjugation on the antigen binding activity and biodistribution of monoclonal antibodies against alpha-fetoprotein. J Nucl Med 26(7): 750-755.
Scarano et al., (2010) Surface plasmon resonance imaging for affinity-based biosensors. Biosens Bioelectron 25(5): 957-966.

(56) References Cited

OTHER PUBLICATIONS

Shaheen et al., (1996) Targeting human immunodeficiency virus type 1 reverse transcriptase by intracellular expression of single-chain variable fragments to inhibit early stages of the viral life cycle J Virol 70(6): 3392-3400.
Solecki et al., (2002) Expression of the human poliovirus receptor/CD155 gene is activated by sonic hedgehog. J Biol Chem 277(28): 25697-25702.
Stanietsky et al., (2013) Mouse TIGIT inhibits NK-cell cytotoxicity upon interaction with PVR. Eur J Immunol 43(8): 2138-2150.
Topalian et al., (2015) Immunotherapy: The path to win the war on cancer?. Cell 161(2): 185-186.
Verhoeyen et al., (1988) Reshaping human antibodies: grafting an antilysozyme activity. Science 239(4847): 1534-1536.
Ward et al., (1989) Binding activities of a repertoire of single immunoglobulin variable domains secreted from *Escherichia coli*. Nature 341(6242): 544-546.
Werge et al., (1990) Intracellular immunization. Cloning and intracellular expression of a monoclonal antibody to the p21ras protein. FEBS Lett 274(1-2): 193-198.
Whitlow and Filpula (1991) Single-chain Fv proteins and their fusion proteins. Methods 2(2): 97-105.
Wu and Kabat (1970) an analysis of the sequences of the variable regions of Bence Jones proteins and myeloma light chains and their implications for antibody complementarity. J Exp Med 132(2): 211-250.
Yang et al., (1986) A common pathway for T lymphocyte activation involving both the CD3-Ti complex and CD2 sheep erythrocyte receptor determinants. J Immunol 137(4): 1097-1100. Abstract.
Yu et al., (2009) The surface protein TIGIT suppresses T cell activation by promoting the generation of mature immunoregulatory dendritic cells. Nat Immunol 10(1): 48-57.
Zapata et al.! (1995) Engineering linear F(ab')2 fragments for efficient production in *Escherichia coli* and enhanced antiproliferative activity. Protein Eng 8(10): 1057-1062.
Zhu et al., (2016) Identification of CD112R as a novel checkpoint for human T cells. J Exp Med 213(2): 167-176.
Beerli et al., (1994) Intracellular expression of single chain antibodies reverts ErbB-2 transformation. J Biol Chem 269(39): 23931-23936.
Berman and Henson (2003) Classifying the precancers: a metadata approach. BMC Med Inform Decis Mak 3: 8; 9 pages.
Biocca et al., (1994) Intracellular immunization with cytosolic recombinant antibodies. Biotechnology (N Y) 12(4): 396-399.
Bird et al., (1988) Single-chain antigen-binding proteins. Science 242(4877): 423-426.
Boerner et al., (1991) Production of antigen-specific human monoclonal antibodies from in vitro-primed human splenocytes. J Immunol 147(1): 86-95.
Brennan et al., (1985) Preparation of bispecific antibodies by chemical recombination of monoclonal immunoglobulin G1 fragments. Science 229(4708): 81-83.
Carlson (1993) A new use for intracellular antibody expression: inactivation of human immunodeficiency virus type 1. Proc Natl Acad Sci U S A 90(16): 7427-7428.
Carter et al., (1992) High level *Escherichia coli* expression and production of a bivalent humanized antibody fragment. Biotechnology (N Y) 10(2): 163-167.
Chauvin et al., (2015) TIGIT and PD-1 impair tumor antigen-specific CD8+ T cells in melanoma patients. J Clin Invest 125(5): 2046-2058.
Chen et al., (1994) Combined intra- and extracellular immunization against human immunodeficiency virus type 1 infection with a human anti-gp120 antibody. Proc Natl Acad Sci U S A 91(13): 5932-5936.
Chen et al., (1994) Intracellular antibodies as a new class of therapeutic molecules for gene therapy. Hum Gene Ther 5(5): 595-601.
Chothia et al., (1989) Conformations of immunoglobulin hypervariable regions. Nature 342(6252): 877-883.

Clackson et al., (1991) Making antibody fragments using phage display libraries. Nature 352(6336): 624-628.
Colman (1994) Effects of amino acid sequence changes on antibody-antigen interactions. Res Immunol 145(1): 33-36.
Deshane et al., (1994) Intracellular single-chain antibody directed against erbB2 down-regulates cell surface erbB2 and exhibits a selective anti-proliferative effect in erbB2 overexpressing cancer cell lines. Gene Ther 1(5): 332-337. Abstract.
Duan et al., (1994) Potent inhibition of human immunodeficiency virus type 1 replication by an intracellular anti-Rev single-chain antibody. Proc Natl Acad Sci U S A 91(11): 5075-5079 with retraction and corrections.
Fields et al., (2013) Creation of recombinant antigen-binding molecules derived from hybridomas secreting specific antibodies. Nat Protoc 8(6): 1125-1148.
Fishwild et al., (1996) High-avidity human IgG kappa monoclonal antibodies from a novel strain of minilocus transgenic mice. Nat Biotechnol 14(7): 845-851.
Gupta et al., (2015) PEITC treatment suppresses myeloid derived tumor suppressor cells to inhibit breast tumor growth. Oncoimmunology 4(2): e981449; 9 pages.
Holliger et al., (1993) "Diabodies": small bivalent and bispecific antibody fragments. Proc Natl Acad Sci U S A 90(14): 6444-6448.
Hoogenboom and Winter (1992) By-passing immunisation. Human antibodies from synthetic repertoires of germline VH gene segments rearranged in vitro. J Mol Biol 227(2): 381-388.
Huntress Rick; Patient-derived tumor xenografts in humanized NSGTM mice: a model to study immune responses in cancer therapy. The Jackson Laboratory. Retrieved from: http://immune-checkpoint.com/wp-content/uploads/sites/24/2015/01/Day-1-15A5-Rick-Huntress.pdf, on Feb. 27, 2017. 34 pages.
Huston et al., (1988) Protein engineering of antibody binding sites: recovery of specific activity in an anti-digoxin single-chain Fv analogue produced in *Escherichia coli*. Proc Natl Aced Sci U S A 85(16): 5879-5883.
Inbar et al., (1972) Localization of antibody-combining sites within the variable portions of heavy and light chains. Proc Natl Acad Sci U S A 69(9): 2659-2662.
Inozume et al., (2013) Development of a novel immunotherapy for melanoma which inhibits interaction between CD155 on melanoma cells and TIGIT on activated CTL. Journal of Investigative Dermatology 133(suppl 1): S3. Abstract No. 018.
Johnston et al., (2014) The immunoreceptor TIGIT regulates antitumor and antiviral CD8(+) T cell effector function. Cancer Cell 26(6): 923-937.
Jones et al., (1986) Replacing the complementarity-determining regions in a human antibody with those from a mouse. Nature 321(6069): 522-525.
Kakunaga et al., (2004) Enhancement of serum- and platelet-derived growth factor-induced cell proliferation by Necl-5/Tage4/poliovirus receptor/CD155 through the Ras-Raf-MEK-ERK signaling. J Biol Chem 279(35): 36419-36425.
Kinugasa et al., (2012) Necl-5/poliovirus receptor interacts with VEGFR2 and regulates VEGF-induced angiogenesis. Circ Res 110(5): 716-726.
Kohler and Milstein (1975) Continuous cultures of fused cells secreting antibody of predefined specificity. Nature 256(5517): 495-497.
Larrick and Fry (1991) PCR amplification of antibody genes. Methods 2(2): 106-110.
Lee et al., (2014) Inhibition of breast cancer growth and metastasis by a biomimetic peptide. Sci Rep 4: 7139; 12 pages.
Lefranc et al., (2003) IMGT unique numbering for immunoglobulin and T cell receptor variable domains and Ig superfamily V-like domains. Dev Comp Immunol 27(1): 55-77.
Lonberg and Huszar (1995) Human antibodies from transgenic mice. Int Rev Immunol 13(1): 65-93.
Lonberg et al., (1994) Antigen-specific human antibodies from mice comprising four distinct genetic modifications. Nature 368(6474): 856-859.
MacCallum et al., (1996) Antibody-antigen interactions: contact analysis and binding site topography. J Mol Biol 262(5): 732-745.

(56) References Cited

OTHER PUBLICATIONS

Makabe et al., (2008) Thermodynamic consequences of mutations in vernier zone residues of a humanized anti-human epidermal growth factor receptor murine antibody, 528. J Biol Chem 283(2): 1156-1166.

Marasco et al., (1998) Intracellular antibodies against HIV-1 envelope protein for AIDS gene therapy. Hum Gene Ther 9(11): 1627-1642.

Marks et al., (1991) By-passing immunization. Human antibodies from V-gene libraries displayed on phage. J Mol Biol 222(3): 581-597.

Marks et al., (1992) By-passing immunization: building high affinity human antibodies by chain shuffling. Biotechnology (N Y) 10(7): 779-783.

Martin et al., (1989) Modeling antibody hypervariable loops: a combined algorithm. Proc Natl Acad Sci U S A 86(23): 9268-9272.

Meuer et al., (1984) An alternative pathway of T-cell activation: a functional role for the 50 kd T11 sheep erythrocyte receptor protein. Cell 36(4): 897-906.

Mhashilkar et al., (1995) Inhibition of HIV-1 Tat-mediated LTR transactivation and HIV-1 infection by anti-Tat single chain intrabodies. EMBO J 14(7): 1542-1551.

Morimoto and Inouye (1992) Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24(1-2): 107-117.

Morimoto et al., (2008) Interaction of cancer cells with platelets mediated by Necl-5/poliovirus receptor enhances cancer cell metastasis to the lungs. Oncogene 27(3): 264-273.

Morrison (1994) Immunology. Success in specification. Nature 368(6474): 812-813.

Morrison et al., (1984) Chimeric human antibody molecules: mouse antigen-binding domains with human constant region domains. Proc Natl Acad Sci U S A 81(21): 6851-6855.

Neuberger (1996) Generating high-avidity human Mabs in mice. Nat Biotechnol 14(7): 826.

Nishiwada et al., (2015) Clinical significance of CD155 expression in human pancreatic cancer Anticancer Res 35(4): 2287-2297 with correction.

Pack et al., (1993) Improved bivalent miniantibodies, with identical avidity as whole antibodies, produced by high cell density fermentation of *Escherichia coli*. Biotechnology (N Y) 11(11): 1271-1277.

\* cited by examiner

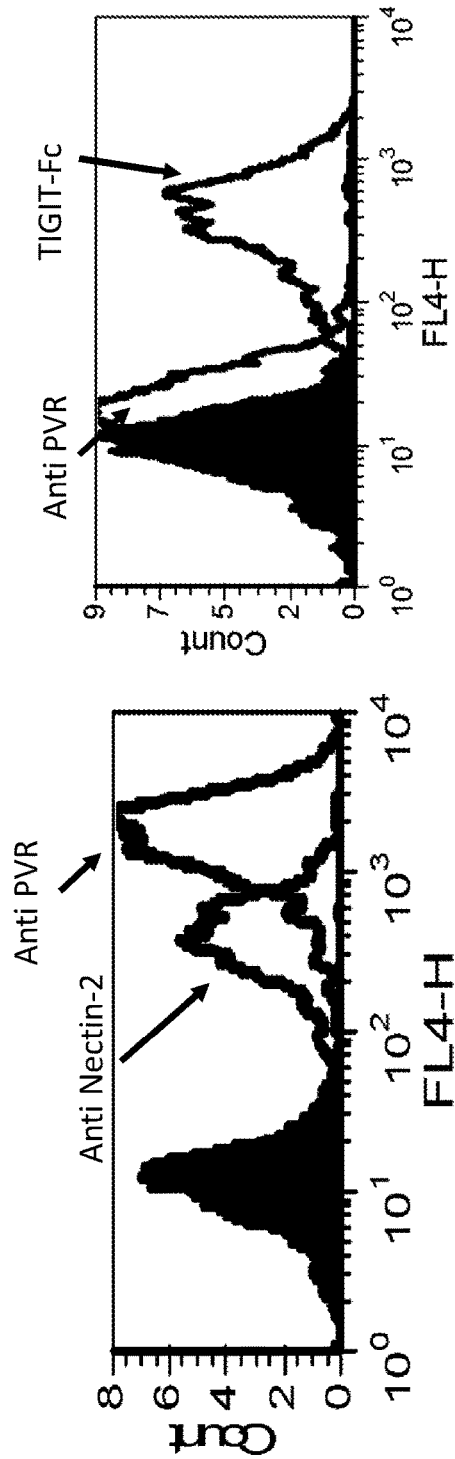
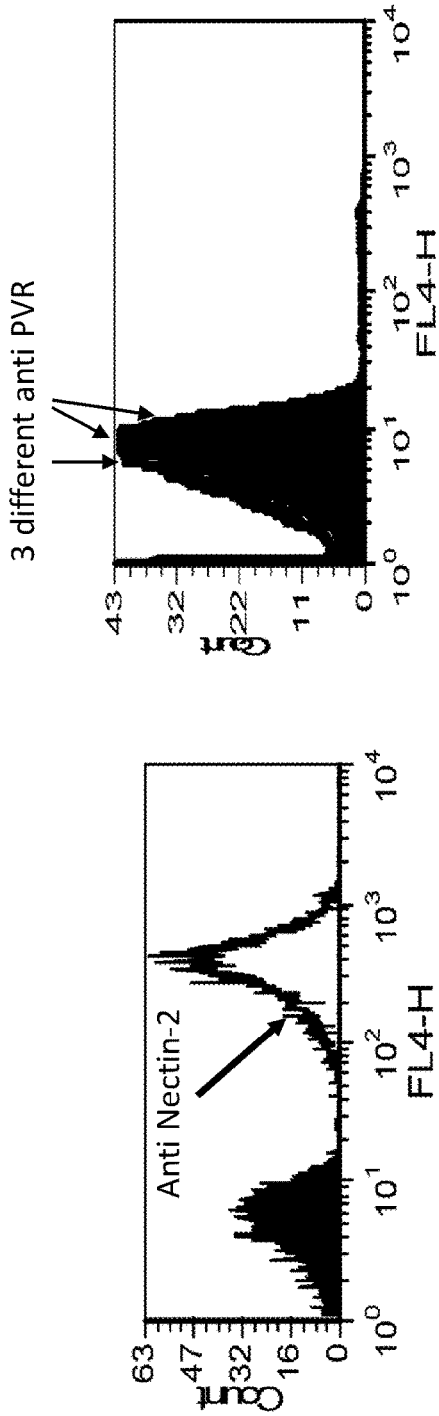
FIGURE 7A
FIGURE 7B
FIGURE 7C
FIGURE 7D

SEQUENCE LISTING

<160> NUMBER OF SEQ ID NOS: 86

<210> SEQ ID NO 1
<211> LENGTH: 390
<212> TYPE: DNA
<213> ORGANISM: Mus musculus

<400> SEQUENCE: 1

```
gaggtgaagc tgcaggagtc tggaggtggc ctggtgcagc ctggaggatc cctgaaactc      60
tcctgtgcag cctcaggatt cgattttagt agatactgga tgacttgggt ccggcaggct     120
ccagggaaag ggctagaatg gattggagaa attcatccag atagcagtaa gataaactat     180
acgccatctc aaaaggataa attcatcatc tccagagaca cgccaaaaa tacgctgttc      240 ctgcaaatga gcaaagtgag atttgaggac acagcccttt atttctgtgc aagacctgat     300
ggtaactaca atgctctgga ctactggggt caaggaacct cagtcaccgt ctcctcagcc     360
aaaacgacac ccccatctgt ctatgtcgac                                      390
```

<210> SEQ ID NO 2
<211> LENGTH: 130
<212> TYPE: PRT
<213> ORGANISM: Mus musculus

<400> SEQUENCE: 2

```
Glu Val Lys Leu Gln Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Thr Trp Val Arg Gln Ala Pro Gly Lys Gly Leu Glu Trp Ile
        35                  40                  45
```

```
Gly Glu Ile His Pro Asp Ser Ser Lys Ile Asn Tyr Thr Pro Ser Gln
        50                  55                  60

Lys Asp Lys Phe Ile Ile Ser Arg Asp Asn Ala Lys Asn Thr Leu Phe
 65                  70                  75                  80

Leu Gln Met Ser Lys Val Arg Phe Glu Asp Thr Ala Leu Tyr Phe Cys
                 85                  90                  95

Ala Arg Pro Asp Gly Asn Tyr Asn Ala Leu Asp Tyr Trp Gly Gln Gly
            100                 105                 110

Thr Ser Val Thr Val Ser Ser Ala Lys Thr Thr Pro Pro Ser Val Tyr
        115                 120                 125

Val Asp
    130

<210> SEQ ID NO 3
<211> LENGTH: 24
<212> TYPE: DNA
<213> ORGANISM: Mus musculus

<400> SEQUENCE: 3
ggattcgatt ttagtagata ctgg                                          24

<210> SEQ ID NO 4
<211> LENGTH: 8
<212> TYPE: PRT
<213> ORGANISM: Mus musculus

<400> SEQUENCE: 4

Gly Phe Asp Phe Ser Arg Tyr Trp
1               5

<210> SEQ ID NO 5
<211> LENGTH: 45
<212> TYPE: DNA
<213> ORGANISM: Mus musculus

<400> SEQUENCE: 5
gaaattcatc cagatagcag taagataaac tatacgccat ctcaa                   45

<210> SEQ ID NO 6
<211> LENGTH: 15
<212> TYPE: PRT
<213> ORGANISM: Mus musculus

<400> SEQUENCE: 6

Glu Ile His Pro Asp Ser Ser Lys Ile Asn Tyr Thr Pro Ser Gln
1               5                   10                  15

<210> SEQ ID NO 7
<211> LENGTH: 33
<212> TYPE: DNA
<213> ORGANISM: Mus musculus

<400> SEQUENCE: 7
cctgatggta actacaatgc tctggactac tgg                                33

<210> SEQ ID NO 8
<211> LENGTH: 11
<212> TYPE: PRT
<213> ORGANISM: Mus musculus

<400> SEQUENCE: 8
```

-continued

Pro Asp Gly Asn Tyr Asn Ala Leu Asp Tyr Trp
1               5                   10

<210> SEQ ID NO 9
<211> LENGTH: 374
<212> TYPE: DNA
<213> ORGANISM: Mus musculus

<400> SEQUENCE: 9
ctgcaaccgg tgtacattcc gacattgtga tgactcagtc tcacaaattc atgtccacat      60
cagtgggaga cagggtcagc atcacctgca aggccagtca ggatgtgggt actgctgtaa     120
cctggtatca acagaaacca ggacaatctc ctaaactact gatttactgg gcatccaccc     180
ggcacactgg agtccctgat cgcttcacag gcagtgaatc tgggacagat ttcactctca     240
ccattagtga tgtgcaatct gaagacttgg caaattattt ctgtcagcaa tatagcaggt     300
atccgtacac gttcggaggg gggaccaagc tggaaataaa acgggccgat gctgcaccaa     360
ctgtatccgt cgac                                                      374

<210> SEQ ID NO 10
<211> LENGTH: 124
<212> TYPE: PRT
<213> ORGANISM: Mus musculus

<400> SEQUENCE: 10

Ala Thr Gly Val His Ser Asp Ile Val Met Thr Gln Ser His Lys Phe
1               5                   10                  15

Met Ser Thr Ser Val Gly Asp Arg Val Ser Ile Thr Cys Lys Ala Ser
            20                  25                  30

Gln Asp Val Gly Thr Ala Val Thr Trp Tyr Gln Gln Lys Pro Gly Gln
        35                  40                  45

Ser Pro Lys Leu Leu Ile Tyr Trp Ala Ser Thr Arg His Thr Gly Val
    50                  55                  60

Pro Asp Arg Phe Thr Gly Ser Glu Ser Gly Thr Asp Phe Thr Leu Thr
65                  70                  75                  80

Ile Ser Asp Val Gln Ser Glu Asp Leu Ala Asn Tyr Phe Cys Gln Gln
                85                  90                  95

Tyr Ser Arg Tyr Pro Tyr Thr Phe Gly Gly Gly Thr Lys Leu Glu Ile
            100                 105                 110

Lys Arg Ala Asp Ala Ala Pro Thr Val Ser Val Asp
        115                 120

<210> SEQ ID NO 11
<211> LENGTH: 33
<212> TYPE: DNA
<213> ORGANISM: Mus musculus

<400> SEQUENCE: 11
aaggccagtc aggatgtggg tactgctgta acc                                  33

<210> SEQ ID NO 12
<211> LENGTH: 11
<212> TYPE: PRT
<213> ORGANISM: Mus musculus

<400> SEQUENCE: 12

Lys Ala Ser Gln Asp Val Gly Thr Ala Val Thr
1               5                   10

<210> SEQ ID NO 13
<211> LENGTH: 21
<212> TYPE: DNA
<213> ORGANISM: Mus musculus

<400> SEQUENCE: 13
tgggcatcca cccggcacac t                                             21

<210> SEQ ID NO 14
<211> LENGTH: 7
<212> TYPE: PRT
<213> ORGANISM: Mus musculus

<400> SEQUENCE: 14

Trp Ala Ser Thr Arg His Thr
1               5

<210> SEQ ID NO 15
<211> LENGTH: 27
<212> TYPE: DNA
<213> ORGANISM: Mus musculus

<400> SEQUENCE: 15
cagcaatata gcaggtatcc gtacacg                                       27

<210> SEQ ID NO 16
<211> LENGTH: 9
<212> TYPE: PRT
<213> ORGANISM: Mus musculus

<400> SEQUENCE: 16

Gln Gln Tyr Ser Arg Tyr Pro Tyr Thr
1               5

<210> SEQ ID NO 17
<211> LENGTH: 526
<212> TYPE: DNA
<213> ORGANISM: Mus musculus

<400> SEQUENCE: 17
gaattcgagg tgaagctgca ggagtctgga cctgagctgg tgaagcctgg ggcttcagtg    60
aagatttcct gcaagacttc tggatacact ttcactgaat acaccatgca ctgggtgagg   120
cagagccatg gagagagcct tgagtggatt ggaggtattg atcctaacaa tggtggtact   180
aactacaacc agaacttcaa gggcaaggcc acattgactg tagacaagtc ctccagcaca   240
gcctacatgg agctccgcag cctgacatct gaggattctg cggtctatta ctgtgcagga   300
gtgattcctc tggagtactg ggggcaagga acctcagtca ccgtctcctc agccaaaacg   360
acacccccat ctgtctatgt cgaccatatg ggagagctcc caacgcgttg gatgcatagc   420
ttgagtattc tatagtgtca cctaaatagc ttggcgtaat catggtcata gctgtttcct   480
gtgtgaaatt gttatccgct cacaattcca cacaacatac gagccg                  526

<210> SEQ ID NO 18
<211> LENGTH: 144
<212> TYPE: PRT
<213> ORGANISM: Mus musculus

<400> SEQUENCE: 18

Glu Phe Glu Val Lys Leu Gln Glu Ser Gly Pro Glu Leu Val Lys Pro
1               5                   10                  15

Gly Ala Ser Val Lys Ile Ser Cys Lys Thr Ser Gly Tyr Thr Phe Thr

```
            20                  25                  30
Glu Tyr Thr Met His Trp Val Arg Gln Ser His Gly Glu Ser Leu Glu
         35                  40                  45

Trp Ile Gly Gly Ile Asp Pro Asn Asn Gly Gly Thr Asn Tyr Asn Gln
     50                  55                  60

Asn Phe Lys Gly Lys Ala Thr Leu Thr Val Asp Lys Ser Ser Ser Thr
 65                  70                  75                  80

Ala Tyr Met Glu Leu Arg Ser Leu Thr Ser Glu Asp Ser Ala Val Tyr
                 85                  90                  95

Tyr Cys Ala Gly Val Ile Pro Leu Glu Tyr Trp Gly Gln Gly Thr Ser
             100                 105                 110

Val Thr Val Ser Ser Ala Lys Thr Thr Pro Pro Ser Val Tyr Val Asp
         115                 120                 125

His Met Gly Glu Leu Pro Thr Arg Trp Met His Ser Leu Ser Ile Leu
     130                 135                 140
```

<210> SEQ ID NO 19
<211> LENGTH: 30
<212> TYPE: DNA
<213> ORGANISM: Mus musculus

<400> SEQUENCE: 19
ggatacactt tcactgaata caccatgcac                                    30

<210> SEQ ID NO 20
<211> LENGTH: 10
<212> TYPE: PRT
<213> ORGANISM: Mus musculus

<400> SEQUENCE: 20

```
Gly Tyr Thr Phe Thr Glu Tyr Thr Met His
1               5                   10
```

<210> SEQ ID NO 21
<211> LENGTH: 51
<212> TYPE: DNA
<213> ORGANISM: Mus musculus

<400> SEQUENCE: 21
ggtattgatc ctaacaatgg tggtactaac tacaaccaga acttcaaggg c              51

<210> SEQ ID NO 22
<211> LENGTH: 16
<212> TYPE: PRT
<213> ORGANISM: Mus musculus

<400> SEQUENCE: 22

```
Gly Ile Asp Pro Asn Asn Gly Gly Thr Asn Tyr Asn Gln Asn Phe Lys
1               5                   10                  15
```

<210> SEQ ID NO 23
<211> LENGTH: 18
<212> TYPE: DNA
<213> ORGANISM: Mus musculus

<400> SEQUENCE: 23
gtgattcctc tggagtac                                                 18

<210> SEQ ID NO 24
<211> LENGTH: 6
<212> TYPE: PRT

<213> ORGANISM: Mus musculus

<400> SEQUENCE: 24

Val Ile Pro Leu Glu Tyr
1               5

<210> SEQ ID NO 25
<211> LENGTH: 321
<212> TYPE: DNA
<213> ORGANISM: Mus musculus

<400> SEQUENCE: 25

```
gatattgtga tgacacagtc tcaaaaattc atgtccacat cagtaggaga cagagtcagc      60
gtcacctgca aggccagtca gaatgtgtat actaatgtag cctggtatca acagaaacca    120
gggcaatctc ctaaagcact gatttactcg gcatcctacc ggtacagggg agtccctgat    180
cgcttcacag gcagtggatc tgggacagat ttcactctca ccatcagcaa tgtgcagtct    240
gaagacttgg cagactattt ctgtcagcaa tataacagct atcctctcgc gttcggctcg    300
gggaccaagc tggagctgaa a                                              321
```

<210> SEQ ID NO 26
<211> LENGTH: 118
<212> TYPE: PRT
<213> ORGANISM: Mus musculus

<400> SEQUENCE: 26

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Tyr Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Arg Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Leu
                85                  90                  95

Ala Phe Gly Ser Gly Thr Lys Leu Glu Ile Lys Arg Ala Asp Ala Ala
            100                 105                 110

Pro Thr Val Ser Val Asp
        115

<210> SEQ ID NO 27
<211> LENGTH: 33
<212> TYPE: DNA
<213> ORGANISM: Mus musculus

<400> SEQUENCE: 27

```
aaggccagtc agaatgtgta tactaatgta gcc                                  33
```

<210> SEQ ID NO 28
<211> LENGTH: 11
<212> TYPE: PRT
<213> ORGANISM: Mus musculus

<400> SEQUENCE: 28

Lys Ala Ser Gln Asn Val Tyr Thr Asn Val Ala
1               5                   10

<210> SEQ ID NO 29
<211> LENGTH: 21
<212> TYPE: DNA
<213> ORGANISM: Mus musculus

<400> SEQUENCE: 29
tcggcatcct accggtacag g         21

<210> SEQ ID NO 30
<211> LENGTH: 7
<212> TYPE: PRT
<213> ORGANISM: Mus musculus

<400> SEQUENCE: 30

Ser Ala Ser Tyr Arg Tyr Arg
1               5

<210> SEQ ID NO 31
<211> LENGTH: 27
<212> TYPE: DNA
<213> ORGANISM: Mus musculus

<400> SEQUENCE: 31
cagcaatata acagctatcc tctcgcg         27

<210> SEQ ID NO 32
<211> LENGTH: 9
<212> TYPE: PRT
<213> ORGANISM: Mus musculus

<400> SEQUENCE: 32

Gln Gln Tyr Asn Ser Tyr Pro Leu Ala
1               5

<210> SEQ ID NO 33
<211> LENGTH: 345
<212> TYPE: DNA
<213> ORGANISM: Mus musculus

<400> SEQUENCE: 33
caactgcagc agtctggagc tgagctgatg aagcctgggg cctcagtgaa gatttcctgc         60
aaggctactg gctacacatt cagtaactac tggattgagt ggataaaaca gaggcctgga        120
catggccttg agtggattgg agagattttt cctggaagtg gtcgtattaa cttcaatgag        180
aagttcaagg gcaaggccac attcactgca gacacatcct ccgacacaac ctacatgcaa        240
ctcagcagcc tgacatctgc ggactctgcc gtctattact gtgcaagaac gaagatctat        300
ggtaactcct tgactactg gggccaaggc accactctca cagtc                        345

<210> SEQ ID NO 34
<211> LENGTH: 115
<212> TYPE: PRT
<213> ORGANISM: Mus musculus

<400> SEQUENCE: 34

Gln Leu Gln Gln Ser Gly Ala Glu Leu Met Lys Pro Gly Ala Ser Val
1               5                   10                  15

Lys Ile Ser Cys Lys Ala Thr Gly Tyr Thr Phe Ser Asn Tyr Trp Ile
            20                  25                  30

Glu Trp Ile Lys Gln Arg Pro Gly His Gly Leu Glu Trp Ile Gly Glu
        35                  40                  45

```
Ile Phe Pro Gly Ser Gly Arg Ile Asn Phe Asn Glu Lys Phe Lys Gly
        50                  55                  60
Lys Ala Thr Phe Thr Ala Asp Thr Ser Ser Asp Thr Thr Tyr Met Gln
65                  70                  75                  80
Leu Ser Ser Leu Thr Ser Ala Asp Ser Ala Val Tyr Tyr Cys Ala Arg
                85                  90                  95
Thr Lys Ile Tyr Gly Asn Ser Phe Asp Tyr Trp Gly Gln Gly Thr Thr
            100                 105                 110
Leu Thr Val
        115

<210> SEQ ID NO 35
<211> LENGTH: 30
<212> TYPE: DNA
<213> ORGANISM: Mus musculus

<400> SEQUENCE: 35
ggctacacat tcagtaacta ctggattgag                                      30

<210> SEQ ID NO 36
<211> LENGTH: 10
<212> TYPE: PRT
<213> ORGANISM: Mus musculus

<400> SEQUENCE: 36

Gly Tyr Thr Phe Ser Asn Tyr Trp Ile Glu
1               5                   10

<210> SEQ ID NO 37
<211> LENGTH: 51
<212> TYPE: DNA
<213> ORGANISM: Mus musculus

<400> SEQUENCE: 37 gagattttc ctggaagtgg tcgtattaac ttcaatgaga agttcaaggg c               51

<210> SEQ ID NO 38
<211> LENGTH: 16
<212> TYPE: PRT
<213> ORGANISM: Mus musculus

<400> SEQUENCE: 38

Glu Ile Phe Pro Gly Ser Gly Arg Ile Asn Phe Asn Glu Lys Phe Lys
1               5                   10                  15

<210> SEQ ID NO 39
<211> LENGTH: 30
<212> TYPE: DNA
<213> ORGANISM: Mus musculus

<400> SEQUENCE: 39
acgaagatct atggtaactc ctttgactac                                      30

<210> SEQ ID NO 40
<211> LENGTH: 10
<212> TYPE: PRT
<213> ORGANISM: Mus musculus

<400> SEQUENCE: 40

Thr Lys Ile Tyr Gly Asn Ser Phe Asp Tyr
1               5                   10
```

<210> SEQ ID NO 41
<211> LENGTH: 324
<212> TYPE: DNA
<213> ORGANISM: Mus musculus

<400> SEQUENCE: 41

```
gacatcgtga tgactcagtc tcacaaattc atgtccacat cagtaggaga cagggtcaac      60
atcacctgca aggccagtca ggatgtgggt actgctgtgg tctggtatca acagaaacca     120
ggacaatctc ctaaattatt gatttactgg gcatccagtc ggcacaatgg agtccctgat     180
cgcttcacag gcagtggatc tgggacagat ttcactctca cgattagtaa tgtgcagtct     240
gaagacttgt cagattattt ctgtcagcaa tatagcaggt atccactcac attcggggct     300
gggaccaagc tggagctgaa acgt                                             324
```

<210> SEQ ID NO 42
<211> LENGTH: 108
<212> TYPE: PRT
<213> ORGANISM: Mus musculus

<400> SEQUENCE: 42

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
            20                  25                  30

Val Val Trp Tyr Gln Gln Lys Pro Gly Gln Ser Pro Lys Leu Leu Ile
        35                  40                  45

Tyr Trp Ala Ser Ser Arg His Asn Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Arg Tyr Pro Leu
                85                  90                  95

Thr Phe Gly Ala Gly Thr Lys Leu Glu Leu Lys Arg
            100                 105

<210> SEQ ID NO 43
<211> LENGTH: 33
<212> TYPE: DNA
<213> ORGANISM: Mus musculus

<400> SEQUENCE: 43

```
aaggccagtc aggatgtggg tactgctgtg gtc                                    33
```

<210> SEQ ID NO 44
<211> LENGTH: 11
<212> TYPE: PRT
<213> ORGANISM: Mus musculus

<400> SEQUENCE: 44

Lys Ala Ser Gln Asp Val Gly Thr Ala Val Val
1               5                   10

<210> SEQ ID NO 45
<211> LENGTH: 21
<212> TYPE: DNA
<213> ORGANISM: Mus musculus

<400> SEQUENCE: 45

```
tgggcatcca gtcggcacaa t                                                 21
```

<210> SEQ ID NO 46
<211> LENGTH: 7
<212> TYPE: PRT
<213> ORGANISM: Mus musculus

<400> SEQUENCE: 46

Trp Ala Ser Ser Arg His Asn
1               5

<210> SEQ ID NO 47
<211> LENGTH: 27
<212> TYPE: DNA
<213> ORGANISM: Mus musculus

<400> SEQUENCE: 47
cagcaatata gcaggtatcc actcaca                                        27

<210> SEQ ID NO 48
<211> LENGTH: 9
<212> TYPE: PRT
<213> ORGANISM: Mus musculus

<400> SEQUENCE: 48

Gln Gln Tyr Ser Arg Tyr Pro Leu Thr
1               5

<210> SEQ ID NO 49
<211> LENGTH: 107
<212> TYPE: PRT
<213> ORGANISM: Artificial Sequence
<220> FEATURE:
<223> OTHER INFORMATION: Mutated chain

<400> SEQUENCE: 49

Asp Ile Met Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
                20                  25                  30

Val Val Trp Tyr Gln Gln Lys Pro Gly Gln Ser Pro Lys Leu Leu Ile
            35                  40                  45

Tyr Trp Ala Ser Ser Arg His Ala Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Arg Tyr Pro Leu
                85                  90                  95

Thr Phe Gly Ala Gly Thr Lys Leu Glu Leu Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: Mutated chain

<400> SEQUENCE: 50

Asp Ile Met Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
                20                  25                  30

Val Val Trp Tyr Gln Gln Lys Pro Gly Gln Ser Pro Lys Leu Leu Ile
            35                  40                  45

Tyr Trp Ala Ser Ser Arg His Arg Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Arg Tyr Pro Leu
                85                  90                  95

Thr Phe Gly Ala Gly Thr Lys Leu Glu Leu Lys
            100                 105

<210> SEQ ID NO 51
<211> LENGTH: 107
<212> TYPE: PRT
<213> ORGANISM: Artificial Sequence
<220> FEATURE:
<223> OTHER INFORMATION: Mutated chain

<400> SEQUENCE: 51

Asp Ile Met Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
            20                  25                  30

Val Val Trp Tyr Gln Gln Lys Pro Gly Gln Ser Pro Lys Leu Leu Ile
            35                  40                  45

Tyr Trp Ala Ser Ser Arg His Asp Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Arg Tyr Pro Leu
                85                  90                  95

Thr Phe Gly Ala Gly Thr Lys Leu Glu Leu Lys
            100                 105

<210> SEQ ID NO 52
<211> LENGTH: 107
<212> TYPE: PRT
<213> ORGANISM: Artificial Sequence
<220> FEATURE:
<223> OTHER INFORMATION: Mutated chain

<400> SEQUENCE: 52

Asp Ile Met Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
            20                  25                  30

Val Val Trp Tyr Gln Gln Lys Pro Gly Gln Ser Pro Lys Leu Leu Ile
            35                  40                  45

Tyr Trp Ala Ser Ser Arg His Glu Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Arg Tyr Pro Leu
                85                  90                  95

Thr Phe Gly Ala Gly Thr Lys Leu Glu Leu Lys
            100                 105

```
<210> SEQ ID NO 53
<211> LENGTH: 107
<212> TYPE: PRT
<213> ORGANISM: Artificial sequence
<220> FEATURE:
<223> OTHER INFORMATION: Mutated chain

<400> SEQUENCE: 53

Asp Ile Met Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
            20                  25                  30

Val Val Trp Tyr Gln Gln Lys Pro Gly Gln Ser Pro Lys Leu Leu Ile
        35                  40                  45

Tyr Trp Ala Ser Ser Arg His Pro Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Arg Tyr Pro Leu
                85                  90                  95

Thr Phe Gly Ala Gly Thr Lys Leu Glu Leu Lys
            100                 105

<210> SEQ ID NO 54
<211> LENGTH: 107
<212> TYPE: PRT
<213> ORGANISM: Artificial sequence
<220> FEATURE:
<223> OTHER INFORMATION: Mutated chain

<400> SEQUENCE: 54

Asp Ile Met Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
            20                  25                  30

Val Val Trp Tyr Gln Gln Lys Pro Gly Gln Ser Pro Lys Leu Leu Ile
        35                  40                  45

Tyr Trp Ala Ser Ser Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Arg Tyr Pro Leu
                85                  90                  95

Thr Phe Gly Ala Gly Thr Lys Leu Glu Leu Lys
            100                 105

<210> SEQ ID NO 55
<211> LENGTH: 7
<212> TYPE: PRT
<213> ORGANISM: Artificial sequence
<220> FEATURE:
<223> OTHER INFORMATION: Mutated CDR
<220> FEATURE:
<221> NAME/KEY: MISC_FEATURE
<222> LOCATION: (7)..(7)
<223> OTHER INFORMATION: Xaa is an amino acid residue selected from:
      Ala, Arg, Asp, Glu, Pro and Thr

<400> SEQUENCE: 55

Trp Ala Ser Ser Arg His Xaa
1               5
```

```
<210> SEQ ID NO 56
<211> LENGTH: 7
<212> TYPE: PRT
<213> ORGANISM: Artificial sequence
<220> FEATURE:
<223> OTHER INFORMATION: Mutated CDR

<400> SEQUENCE: 56

Trp Ala Ser Ser Arg His Ala
1               5

<210> SEQ ID NO 57
<211> LENGTH: 7
<212> TYPE: PRT
<213> ORGANISM: Artificial sequence
<220> FEATURE:
<223> OTHER INFORMATION: Mutated CDR

<400> SEQUENCE: 57

Trp Ala Ser Ser Arg His Arg
1               5

<210> SEQ ID NO 58
<211> LENGTH: 7
<212> TYPE: PRT
<213> ORGANISM: Artificial sequence
<220> FEATURE:
<223> OTHER INFORMATION: Mutated CDR

<400> SEQUENCE: 58

Trp Ala Ser Ser Arg His Asp
1               5

<210> SEQ ID NO 59
<211> LENGTH: 7
<212> TYPE: PRT
<213> ORGANISM: Artificial sequence
<220> FEATURE:
<223> OTHER INFORMATION: Mutated CDR

<400> SEQUENCE: 59

Trp Ala Ser Ser Arg His Glu
1               5

<210> SEQ ID NO 60
<211> LENGTH: 7
<212> TYPE: PRT
<213> ORGANISM: Artificial sequence
<220> FEATURE:
<223> OTHER INFORMATION: Mutated CDR

<400> SEQUENCE: 60

Trp Ala Ser Ser Arg His Pro
1               5

<210> SEQ ID NO 61
<211> LENGTH: 7
<212> TYPE: PRT
<213> ORGANISM: Artificial sequence
<220> FEATURE:
<223> OTHER INFORMATION: Mutated CDR

<400> SEQUENCE: 61

Trp Ala Ser Ser Arg His Thr
1               5
```

```
<210> SEQ ID NO 62
<211> LENGTH: 321
<212> TYPE: DNA
<213> ORGANISM: Artificial sequence
<220> FEATURE:
<223> OTHER INFORMATION: Mutated polynucleotide

<400> SEQUENCE: 62
gacatcatga tgacccagtc tcacaaattc atgtctacat ctgtaggaga cagagtcaac    60
atcacttgca aggcgagtca ggatgtgggt actgctgtgg tctggtatca gcagaaacca   120
gggcaatctc ctaagttgct gatctattgg gcatccagtc ggcacgctgg ggtcccagat   180
aggttcacag gcagtggatc tgggacagat ttcactctca ccatcagcaa tgtgcagtct   240
gaagatttgt cagattattt ctgccaacag tatagcagat accctctcac attcggggct   300
gggaccaagc tggagctcaa a                                             321

<210> SEQ ID NO 63
<211> LENGTH: 321
<212> TYPE: DNA
<213> ORGANISM: Artificial sequence
<220> FEATURE:
<223> OTHER INFORMATION: Mutated polynucleotide

<400> SEQUENCE: 63
gacatcatga tgacccagtc tcacaaattc atgtctacat ctgtaggaga cagagtcaac    60
atcacttgca aggcgagtca ggatgtgggt actgctgtgg tctggtatca gcagaaacca   120
gggcaatctc ctaagttgct gatctattgg gcatccagtc ggcacagagg ggtcccagat   180
aggttcacag gcagtggatc tgggacagat ttcactctca ccatcagcaa tgtgcagtct   240
gaagatttgt cagattattt ctgccaacag tatagcagat accctctcac attcggggct   300
gggaccaagc tggagctcaa a                                             321

<210> SEQ ID NO 64
<211> LENGTH: 321
<212> TYPE: DNA
<213> ORGANISM: Artificial sequence
<220> FEATURE:
<223> OTHER INFORMATION: Mutated polynucleotide

<400> SEQUENCE: 64
gacatcatga tgacccagtc tcacaaattc atgtctacat ctgtaggaga cagagtcaac    60
atcacttgca aggcgagtca ggatgtgggt actgctgtgg tctggtatca gcagaaacca   120
gggcaatctc ctaagttgct gatctattgg gcatccagtc ggcacgatgg ggtcccagat   180
aggttcacag gcagtggatc tgggacagat ttcactctca ccatcagcaa tgtgcagtct   240
gaagatttgt cagattattt ctgccaacag tatagcagat accctctcac attcggggct   300
gggaccaagc tggagctcaa a                                             321

<210> SEQ ID NO 65
<211> LENGTH: 321
<212> TYPE: DNA
<213> ORGANISM: Artificial sequence
<220> FEATURE:
<223> OTHER INFORMATION: Mutated polynucleotide

<400> SEQUENCE: 65
gacatcatga tgacccagtc tcacaaattc atgtctacat ctgtaggaga cagagtcaac    60
atcacttgca aggcgagtca ggatgtgggt actgctgtgg tctggtatca gcagaaacca   120
```

```
gggcaatctc ctaagttgct gatctattgg gcatccagtc ggcacgaggg ggtcccagat    180
aggttcacag gcagtggatc tgggacagat ttcactctca ccatcagcaa tgtgcagtct    240
gaagatttgt cagattattt ctgccaacag tatagcagat accctctcac attcggggct    300
gggaccaagc tggagctcaa a                                              321

<210> SEQ ID NO 66
<211> LENGTH: 321
<212> TYPE: DNA
<213> ORGANISM: Artificial sequence
<220> FEATURE:
<223> OTHER INFORMATION: Mutated polynucleotide

<400> SEQUENCE: 66
gacatcatga tgacccagtc tcacaaattc atgtctacat ctgtaggaga cagagtcaac     60
atcacttgca aggcgagtca ggatgtgggt actgctgtgg tctggtatca gcagaaacca    120
gggcaatctc ctaagttgct gatctattgg gcatccagtc ggcaccctgg ggtcccagat    180
aggttcacag gcagtggatc tgggacagat ttcactctca ccatcagcaa tgtgcagtct    240
gaagatttgt cagattattt ctgccaacag tatagcagat accctctcac attcggggct    300
gggaccaagc tggagctcaa a                                              321

<210> SEQ ID NO 67
<211> LENGTH: 321
<212> TYPE: DNA
<213> ORGANISM: Artificial sequence
<220> FEATURE:
<223> OTHER INFORMATION: Mutated polynucleotide

<400> SEQUENCE: 67
gacatcatga tgacccagtc tcacaaattc atgtctacat ctgtaggaga cagagtcaac     60
atcacttgca aggcgagtca ggatgtgggt actgctgtgg tctggtatca gcagaaacca    120
gggcaatctc ctaagttgct gatctattgg gcatccagtc ggcacactgg ggtcccagat    180
aggttcacag gcagtggatc tgggacagat ttcactctca ccatcagcaa tgtgcagtct    240
gaagatttgt cagattattt ctgccaacag tatagcagat accctctcac attcggggct    300
gggaccaagc tggagctcaa a                                              321

<210> SEQ ID NO 68
<211> LENGTH: 356
<212> TYPE: DNA
<213> ORGANISM: Mus musculus

<400> SEQUENCE: 68
gaggtgaagc ttctcgagtc tggaggtggc ctggtgcagc ctggaggatc cctgaaactc     60
tcctgtgcag cctcaggatt cgattttagt agatactgga tgacttgggt ccggcaggct    120
ccagggaaag gctagaatg gattggagaa attcatccag atagcagtaa gataaactat    180
acgccatctc aaaaggataa attcatcatc tccagagaca cgccaaaaa tacgctgttc    240 ctgcaaatga gcaaagtgag atttgaggac acagcccttt atttctgtgc aagacctgat    300
ggtaactaca atgctctgga ctactggggt caaggaacct cagtcaccgt ctcctc        356

<210> SEQ ID NO 69
<211> LENGTH: 119
<212> TYPE: PRT
<213> ORGANISM: Mus musculus

<400> SEQUENCE: 69
```

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Thr Trp Val Arg Gln Ala Pro Gly Lys Gly Leu Glu Trp Ile
        35                  40                  45

Gly Glu Ile His Pro Asp Ser Ser Lys Ile Asn Tyr Thr Pro Ser Gln
    50                  55                  60

Lys Asp Lys Phe Ile Ile Ser Arg Asp Asn Ala Lys Asn Thr Leu Phe
65                  70                  75                  80

Leu Gln Met Ser Lys Val Arg Phe Glu Asp Thr Ala Leu Tyr Phe Cys
                85                  90                  95

Ala Arg Pro Asp Gly Asn Tyr Asn Ala Leu Asp Tyr Trp Gly Gln Gly
            100                 105                 110

Thr Ser Val Thr Val Ser Ser
        115
```

<210> SEQ ID NO 70
<211> LENGTH: 321
<212> TYPE: DNA
<213> ORGANISM: Mus musculus

<400> SEQUENCE: 70

```
gacattgtga tgacccagtc tcacaaattc atgtccacat cagtgggaga cagggtcagc      60
atcacctgca aggccagtca ggatgtgggt actgctgtaa cctggtatca acagaaacca     120
ggacaatctc ctaaactact gatttactgg gcatccaccc ggcacactgg agtccctgat     180
cgcttcacag gcagtgaatc tgggacagat ttcactctca ccattagtga tgtgcaatct     240
gaagacttgg caaattattt ctgtcagcaa tatagcaggt atccgtacac gttcggaggg     300
gggaccaagc tggaaataaa a                                               321
```

<210> SEQ ID NO 71
<211> LENGTH: 107
<212> TYPE: PRT
<213> ORGANISM: Mus musculus

<400> SEQUENCE: 71

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Thr Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Glu Ser Gly Thr Asp Phe Thr Leu Thr Ile Ser Asp Val Gln Ser
65                  70                  75                  80

Glu Asp Leu Ala Asn Tyr Phe Cys Gln Gln Tyr Ser Arg Tyr Pro Tyr
                85                  90                  95

Thr Phe Gly Gly Gly Thr Lys Leu Glu Ile Lys
            100                 105
```

<210> SEQ ID NO 72
<211> LENGTH: 345
<212> TYPE: DNA
<213> ORGANISM: Mus musculus

<400> SEQUENCE: 72

```
gaggtccagc tgcaacagtc tggacctgag ctggtgaagc ctggggcttc agtgaagatt      60
tcctgcaaga cttctggata cactttcact gaatacacca tgcactgggt gaagcagagc     120
catggagaga gccttgagtg gattggaggt attgatccta acaatggtgg tactaactac     180
aaccagaact tcaagggcaa ggccacattg actgtagaca gtcctccag cacagcctac      240
atggagctcc gcagcctgac atctgaggat tctgcggtct attactgtgc aggagtgatt     300
cctctggagt actgggggca aggaacctca gtcaccgtct cctca                     345
```

<210> SEQ ID NO 73
<211> LENGTH: 115
<212> TYPE: PRT
<213> ORGANISM: Mus musculus

<400> SEQUENCE: 73

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Glu Ser Leu Glu Trp Ile
        35                  40                  45

Gly Gly Ile Asp Pro Asn Asn Gly Gly Thr Asn Tyr Asn Gln Asn Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Val Ile Pro Leu Glu Tyr Trp Gly Gln Gly Thr Ser Val Thr
            100                 105                 110

Val Ser Ser
        115
```

<210> SEQ ID NO 74
<211> LENGTH: 321
<212> TYPE: DNA
<213> ORGANISM: Mus musculus

<400> SEQUENCE: 74

```
gacattgtga tgacccagtc tcaaaaattc atgtccacat cagtaggaga cagagtcagc      60
gtcacctgca aggccagtca gaatgtgtat actaatgtag cctggtatca acagaaacca     120
gggcaatctc ctaaagcact gatttactcg gcatcctacc ggtacagggg agtccctgat     180
cgcttcacag gcagtggatc tgggacagat ttcactctca ccatcagcaa tgtgcagtct     240
gaagacttgg cagactattt ctgtcagcaa tataacagct atcctctcgc gttcggctcg     300
gggacaaagt tggaaataaa a                                                321
```

<210> SEQ ID NO 75
<211> LENGTH: 107
<212> TYPE: PRT
<213> ORGANISM: Mus musculus

<400> SEQUENCE: 75

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Tyr Thr Asn
```

```
            20                  25                  30
Val Ala Trp Tyr Gln Gln Lys Pro Gly Gln Ser Pro Lys Ala Leu Ile
         35                  40                  45

Tyr Ser Ala Ser Tyr Arg Tyr Arg Gly Val Pro Asp Arg Phe Thr Gly
     50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Leu
                 85                  90                  95

Ala Phe Gly Ser Gly Thr Lys Leu Glu Ile Lys
            100                 105
```

<210> SEQ ID NO 76
<211> LENGTH: 357
<212> TYPE: DNA
<213> ORGANISM: Mus musculus

<400> SEQUENCE: 76

```
caggttcagt tgcagcagtc tggagctgag ctgatgaagc ctggggcctc agtgaagatt      60
tcctgcaagg ctactggcta cacattcagt aactactgga ttgagtggat aaaacagagg     120
cctggacatg gccttgagtg gattggagag atttttcctg gaagtggtcg tattaacttc     180
aatgagaagt tcaagggcaa ggccacattc actgcagaca catcctccga cacaacctac     240
atgcaactca gcagcctgac atctgcggac tctgccgtct attactgtgc aagaacgaag     300
atctatggta actcctttga ctactggggc caaggcacca ctctcacagt ctcccca       357
```

<210> SEQ ID NO 77
<211> LENGTH: 119
<212> TYPE: PRT
<213> ORGANISM: Mus musculus

<400> SEQUENCE: 77

```
Gln Val Gln Leu Gln Gln Ser Gly Ala Glu Leu Met Lys Pro Gly Ala
1               5                  10                  15

Ser Val Lys Ile Ser Cys Lys Ala Thr Gly Tyr Thr Phe Ser Asn Tyr
            20                  25                  30

Trp Ile Glu Trp Ile Lys Gln Arg Pro Gly His Gly Leu Glu Trp Ile
         35                  40                  45

Gly Glu Ile Phe Pro Gly Ser Gly Arg Ile Asn Phe Asn Glu Lys Phe
     50                  55                  60

Lys Gly Lys Ala Thr Phe Thr Ala Asp Thr Ser Ser Asp Thr Thr Tyr
65                  70                  75                  80

Met Gln Leu Ser Ser Leu Thr Ser Ala Asp Ser Ala Val Tyr Tyr Cys
                 85                  90                  95

Ala Arg Thr Lys Ile Tyr Gly Asn Ser Phe Asp Tyr Trp Gly Gln Gly
            100                 105                 110

Thr Thr Leu Thr Val Ser Pro
        115
```

<210> SEQ ID NO 78
<211> LENGTH: 321
<212> TYPE: DNA
<213> ORGANISM: Mus musculus

<400> SEQUENCE: 78

```
gacattatga tgacccagtc tcacaaattc atgtccacat cagtaggaga cagggtcaac      60
```

```
atcacctgca aggccagtca ggatgtgggt actgctgtgg tctggtatca acagaaacca    120
ggacaatctc ctaaattatt gatttactgg gcatccagtc ggcacaatgg agtccctgat    180
cgcttcacag gcagtggatc tgggacagat ttcactctca cgattagtaa tgtgcagtct    240
gaagacttgt cagattattt ctgtcagcaa tatagcaggt atccactcac attcggggct    300
gggaccaagc tggagctgaa a                                              321
```

<210> SEQ ID NO 79
<211> LENGTH: 107
<212> TYPE: PRT
<213> ORGANISM: Mus musculus

<400> SEQUENCE: 79

```
Asp Ile Met Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
            20                  25                  30

Val Val Trp Tyr Gln Gln Lys Pro Gly Gln Ser Pro Lys Leu Leu Ile
        35                  40                  45

Tyr Trp Ala Ser Ser Arg His Asn Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Arg Tyr Pro Leu
                85                  90                  95

Thr Phe Gly Ala Gly Thr Lys Leu Glu Leu Lys
            100                 105
```

<210> SEQ ID NO 80
<211> LENGTH: 5
<212> TYPE: PRT
<213> ORGANISM: Mus musculus

<400> SEQUENCE: 80

```
Arg Tyr Trp Met Thr
1               5
```

<210> SEQ ID NO 81
<211> LENGTH: 17
<212> TYPE: PRT
<213> ORGANISM: Mus musculus

<400> SEQUENCE: 81

```
Glu Ile His Pro Asp Ser Ser Lys Ile Asn Tyr Thr Pro Ser Gln Lys
1               5                   10                  15

Asp
```

<210> SEQ ID NO 82
<211> LENGTH: 10
<212> TYPE: PRT
<213> ORGANISM: Mus musculus

<400> SEQUENCE: 82

```
Pro Asp Gly Asn Tyr Asn Ala Leu Asp Tyr
1               5                   10
```

<210> SEQ ID NO 83
<211> LENGTH: 5
<212> TYPE: PRT
<213> ORGANISM: Mus musculus

<400> SEQUENCE: 83

Glu Tyr Thr Met His
1               5

<210> SEQ ID NO 84
<211> LENGTH: 6
<212> TYPE: PRT
<213> ORGANISM: Mus musculus

<400> SEQUENCE: 84

Ser Asn Tyr Trp Ile Glu
1               5

<210> SEQ ID NO 85
<211> LENGTH: 10
<212> TYPE: PRT
<213> ORGANISM: Mus musculus

<400> SEQUENCE: 85

Lys Ala Ser Gln Asp Val Gly Thr Ala Val
1               5                   10

<210> SEQ ID NO 86
<211> LENGTH: 329
<212> TYPE: PRT
<213> ORGANISM: Homo sapiens

<400> SEQUENCE: 86

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met

```
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
                260                 265                 270
Tyr Lys Thr Thr Pro Pro Val Leu Asp Ser Asp Gly Ser Phe Phe Leu
        275                 280                 285
Tyr Ser Lys Leu Thr Val Asp Lys Ser Arg Trp Gln Gln Gly Asn Val
        290                 295                 300
Phe Ser Cys Ser Val Met His Glu Ala Leu His Asn His Tyr Thr Gln
305                 310                 315                 320
Lys Ser Leu Ser Leu Ser Pro Gly Lys
                325
```

ANTIBODIES SPECIFIC TO HUMAN POLIOVIRUS RECEPTOR (PVR)

FIELD OF THE INVENTION

The invention is in the field of immunotherapy and relates to antibodies and fragments thereof which bind to the protein poliovirus receptor, to polynucleotide sequences encoding these antibodies and to hybridoma cells producing these antibodies. The invention further relates to therapeutic and diagnostic compositions comprising these antibodies and to methods of treating and diagnosing diseases, particularly cancer, using these monoclonal antibodies.

BACKGROUND OF THE INVENTION

Cancer immunotherapy is utilized for generating and augmenting an anti-tumor immune response, e.g., by treatment with antibodies specific to antigens on tumor cells, with fusions of antigen presenting cells with tumor cells, or by specific activation of anti-tumor T cells. The ability of recruiting immune cells (e.g. T cells) against tumor cells in a patient provides a therapeutic modality of fighting cancer types and metastasis that so far were considered incurable.

T cell mediated immune response includes multiple sequential steps regulated by a balance between co-stimulatory and co-inhibitory signals that control the magnitude of the immune response. The inhibitory signals, referred to as immune checkpoints, are crucial for the maintenance of self-tolerance and also for the limitation of immune-mediated collateral tissue damage. These signals change as an infection or immune provocation is cleared, worsens, or persists, and these changes affect the response of T cells and re-shape the immune response.

The expression of immune checkpoint proteins can be regulated by tumors. For example, upregulation of programmed death-1 ligand (PD-L1) on the cancer cell surface allows them to evade the host immune system by inhibiting T cells via binding to PD-1 that might otherwise attack these tumor cells. Thus, immune checkpoints represent significant barriers to activation of functional cellular immunity against cancer. Accordingly, antagonistic antibodies specific for inhibitory ligands on immune cells are considered viable anti-cancer agents and they are being evaluated in the clinics (e.g. Nivolumab and Pembrolizumab). Another example for immune checkpoint molecule is T cell immunoreceptor with Ig and ITIM domains (TIGIT). TIGIT is a co-inhibitory molecule expressed on various immune cells including T cells and Natural Killer cells (NK cells). TIGIT binds with high affinity to polio virus receptor (PVR).

Poliovirus receptor (PVR), also termed CD155, is a transmembrane glycoprotein involved in mediating cell adhesion to extracellular matrix molecules. It was previously described as a tumor antigen and as a potential target for therapeutic intervention as its expression is up-regulated in neuroectodermal cancers, including glioblastoma multiforme, medulloblastoma, and colorectal carcinoma (Solecki et al., J. Biol. Chem. 2002, 277: 25697-700) as well as in pancreatic cancer (Nishiwada et al., Anticancer Res. 2015, 35(4): 2287-97).

PVR is also known to enhance the serum-induced activation of the Ras-Raf-MEK-ERK signaling, up-regulating cyclins D2 and E, and down-regulated p27Kip1, eventually shortening the period of the G0/G1 phase of the cell cycle (Kakunaga 2004, J. Biological Chemistry, 279, 36419-36425) for that reason blocking of PVR on tumor cells is anticipated to reduce viability of tumor cells. PVR has also a critical role in angiogenesis and is suggested to regulate the VEGF-induced angiogenesis by controlling the interaction of VEGFR2 with integrin α(v)β(3), and the VEGFR2-mediated Rap1-Akt signaling pathway (Kinugasa et al., 2012, Circ Res. 2012, 110(5), 716-26). Additionally, PVR is complexing with IGF1R and participating in Met signaling and blocking the complex formation reduced cell viability and angiogenesis (Lee et al., Scientific Reports 2014, 20, 4, 7139).

PVR involvement in metastasis was demonstrated by injecting cancer cells to the tail of mice and measuring metastasis to the lungs. It has been shown that the upregulated PVR in cancer cells transinteracts with its counter-receptor in platelets, and that this trans-interaction enhances the metastasis of the cancer cells to the lungs (Morimoto et al., Oncogene (2008) 27, 264-273).

U.S. Patent Application No. 20070041985 discloses molecules specifically binding to at least one intra- or extracellular domain of the PVR or any derivative thereof, wherein the molecule has the ability to modulate a receptor mediated adhesion, trafficking and/or invasion behavior of a cell expressing the PVR or any derivative thereof.

U.S. Patent Application No. 20090215175 provides molecules (e.g. small chemical compounds, oligonucleotides, polypeptides, antibodies, and antibody fragments) which modulate the PVR functions necessary for adhesion, trafficking, invasion and/or metastatic potential of cells. The molecules can be used for the treatment of cells having a metastatic potential, metastasis and cancer.

PCT Application Publication No. WO 2006/124667 discloses modulation of the protein zB7R1 (TIGIT) by monoclonal antibodies that block TIGIT binding to its ligand PVR.

There is an unmet need to provide additional and more effective, specific, safe and/or stable agents that alone or in combination with other agents, potentiate cells of the immune system to attack tumor or virus infected cells by inhibiting PVR binding to TIGIT.

SUMMARY OF THE INVENTION

The present invention provides antibodies and fragments thereof that recognize the poliovirus receptor (PVR), prevent its binding to T cell immunoreceptor with Ig and ITIM domains (TIGIT) and inhibit suppressive activity on lymphocytes such as natural killer (NK) cells and T-cells. The anti-PVR antibodies disclosed herein are capable of binding to PVR present on cancer cells. These antibodies and fragment thereof are characterized by having unique sets of complementarity-determining regions (CDR) sequences, high affinity and high specificity to PVR and are useful in cancer immunotherapy for combating tumor immune evasion, as stand-alone therapy and in combination with other anti-cancer agents. The antibodies are also useful in treating viral infections.

It is now disclosed that the high affinity anti-PVR antibodies disclosed herein block TIGIT-PVR interaction and restore T and NK cells activity. The antibodies showed high specificity to human PVR. These properties make the monoclonal antibodies (mAbs) of the present invention valuable candidates for use in cancer immune-therapy, enabling administration of lower doses with fewer side effects.

Advantageously, the anti-PVR mAbs according to the invention can induce T cells proliferation better than anti PD-1 and CTLA-4 mAbs in a PD-L1 in-vitro model (A549). The induction effect was shown for peripheral mononuclear blood cells (PMBCs) and purified CD4 and CD8 T cells. In addition, PVR mAbs were able to induce NK cell activation in most target cells tested. Moreover, some of the anti-PVR antibodies described herein have comparable anti-cancer activity in-vitro to those of a known agent, Erbitux® currently used in therapy. Furthermore, some of the anti-PVR antibodies described herein showed synergistic effect when combined with additional anti-cancer agents, such as anti PD-1 and CTLA-1 antibodies and epidermal growth factor receptor (EGFR). In addition, some of the anti-PVR antibodies were found to induce antibody-dependent cell-mediated cytotoxicity (ADCC). It is further disclosed that some anti-PVR antibodies according to the invention had no blocking effect on the co-stimulatory signaling of DNAM1, therefore they have no deleterious effect on other immune induction signals.

Interestingly, despite high sequence similarity between human and rodent PVR sequences, the antibodies of the present invention are highly specific to human PVR.

It is further disclosed that unexpectedly some chimeric monoclonal antibodies, comprising human constant chain, showed enhanced effect on immune cell activation in comparison to their equivalent murine monoclonal antibodies.

Some of the anti PVR mAbs described herein were able to reduce tumor cells viability in an immune independent manner by blocking of PVR on tumor cells. Without wishing to be bound to any mechanism of action, it is suggested that this activity results from the ability of PVR to shortening the period of the G0/G1 phase of the cell cycle.

According to one aspect, the present invention provides an isolated monoclonal antibody which binds to poliovirus receptor (PVR), or an antibody fragment thereof comprising at least the antigen binding portion, wherein the isolated antibody or antibody fragment is selected from the group consisting of:
  i. three CDRs of a heavy-chain (HC) variable region comprising SEQ ID NO: 77 and three CDRs of a light-chain (LC) variable comprising SEQ ID NO: 79, or an analog or derivative thereof having at least 90% sequence identity with said antibody or fragment sequence;
  ii. three complementarity determining regions (CDRs) of a heavy-chain variable region comprising SEQ ID NO: 69 and three CDRs of a light-chain variable region comprising SEQ ID NO: 71, or an analog or derivative thereof having at least 90% sequence identity with said antibody or fragment sequence; and
  iii. three CDRs of a heavy-chain variable region comprising SEQ ID NO: 73 and three CDRs of a light-chain variable region comprising SEQ ID NO: 75, or an analog or derivative thereof having at least 90% sequence identity with said antibody or fragment sequence.

Antibodies comprising CDR sequences contained in heavy and light chains homologues to SEQ ID Nos: 2, 10, 18, 26, 34 or 42 are also included within the scope of the present invention. According to some embodiments, SEQ ID NO: 2 is interchangeable with SEQ ID NO: 69. According to some embodiments, SEQ ID NO: 10 is interchangeable with SEQ ID NO: 71. According to some embodiments, SEQ ID NO: 18 is interchangeable with SEQ ID NO: 73. According to some embodiments, SEQ ID NO: 26 is interchangeable with SEQ ID NO: 75. According to some embodiments, SEQ ID NO: 34 is interchangeable with SEQ ID NO: 77. According to some embodiments, SEQ ID NO: 42 is interchangeable with SEQ ID NO: 79.

There are several methods known in the art for determining the CDR sequences of a given antibody molecule, but there is no standard unequivocal method. Determination of CDR sequences from antibody heavy and light chain variable regions can be made according to any method known in the art, including but not limited to the methods known as KABAT, Chothia and IMGT. A selected set of CDRs may include sequences identified by more than one method, namely, some CDR sequences may be determined using KABAT and some using IMGT, for example.

According to some embodiments, the isolated monoclonal antibody or fragment comprises the CDR sequences of a monoclonal antibody denoted Anti-PVR 4E5 (or hPVR.07), namely, the three CDR sequences contained in heavy chain variable region set forth in SEQ ID NO: 69 and the three CDR sequences contained in light chain variable region set forth in SEQ ID NO: 71.

According to some embodiments, the isolated monoclonal antibody or the antibody fragment comprises heavy-chain CDR1 comprising the sequence GFDFSRYW (SEQ ID NO: 4). According to some embodiments, the isolated monoclonal antibody or the antibody fragment comprises heavy-chain CDR2 comprising the sequence EIHPDSSKINYTPSQ (SEQ ID NO: 6). According to some embodiments, the isolated monoclonal antibody or the antibody fragment comprises heavy-chain CDR3 comprising the sequence PDGNYNALDYW (SEQ ID NO: 8).

According to some embodiments, the isolated monoclonal antibody or antibody fragment comprises heavy-chain CDR1 comprising the sequence RYW. According to some embodiments, the isolated monoclonal antibody or the antibody fragment comprises heavy-chain CDR1 comprising the sequence RYWMT (SEQ ID NO: 80). According to some embodiments, the isolated monoclonal antibody or the antibody fragment comprises heavy-chain CDR3 comprising the sequence PDGNYNALDY (SEQ ID NO: 82).

According to certain embodiments, the isolated monoclonal antibody or the antibody fragment comprises: (i) HC CDR1 comprising the sequence GFDFSRYW (SEQ ID NO: 4); (ii) HC CDR2 comprising the sequence: EIHPDSSKINYTPSQ (SEQ ID NO: 6); and (iii) HC CDR3 comprising the sequence: PDGNYNALDYW (SEQ ID NO: 8).

According to certain embodiments, the isolated monoclonal antibody or the antibody fragment comprises: (i) HC CDR1 comprising the sequence RYW; (ii) HC CDR2 comprising the sequence: EIHPDSSKINYTPSQ (SEQ ID NO: 6); and (iii) HC CDR3 comprising the sequence: PDGNYNALDY (SEQ ID NO: 82).

According to some embodiments, the isolated monoclonal antibody or the antibody fragment comprises light-chain CDR1 comprising the sequence KASQDVGTAVT (SEQ ID NO: 12). According to some embodiments, the isolated monoclonal antibody or the antibody fragment comprises light-chain CDR2 comprising the sequence WASTRHT (SEQ ID NO: 14). According to some embodiments, the isolated monoclonal antibody or the antibody fragment comprises light-chain CDR3 comprising the sequence QQYSRYPYT (SEQ ID NO: 16). According to certain embodiments, the isolated monoclonal antibody or the antibody fragment comprises: (i) LC CDR1 comprises the sequence KASQDVGTAVT (SEQ ID NO: 12); (ii) LC CDR2 comprises the sequence: WASTRHT (SEQ ID NO: 14); and (iii) HC CDR3 comprises the sequence: QQYSRYPYT (SEQ ID NO: 16).

According to some specific embodiments the isolated monoclonal antibody or fragment comprises heavy chain CDR1 sequence comprising the sequence: GFDFSRYW (SEQ ID NO: 4), heavy chain CDR2 comprising the sequence: EIHPDSSKINYTPSQ (SEQ ID NO: 6), heavy chain CDR3 comprising the sequence: PDGNYNALDYW (SEQ ID NO: 8), light chain CDR1 comprising the sequence: KASQDVGTAVT (SEQ ID NO: 12), light chain CDR2 comprising the sequence: WASTRHT (SEQ ID NO: 14), and light chain CDR3 comprising the sequence: QQYSRYPYT (SEQ ID NO: 16), or analogs thereof comprising no more than 5% amino acid substitution, deletion and/or insertion in the hypervariable region (HVR) sequence.

According to some specific embodiments the isolated monoclonal antibody or fragment comprises a set of six CDR sequences consisting of:
i. heavy chain CDR1 having a sequence selected from the group consisting of SEQ ID NO: 4 and SEQ ID NO: 80,
ii. heavy chain CDR2 having a sequence selected from the group consisting of SEQ ID NO: 6 and SEQ ID NO: 81,
iii. heavy chain CDR3 having a sequence selected from the group consisting of SEQ ID NO: 8 and SEQ ID NO: 82,
iv. light chain CDR1 having a sequence set forth in SEQ ID NO: 12,
v. light chain CDR2 having a sequence set forth in SEQ ID NO: 14, and
vi. light chain CDR3 having a sequence set forth in SEQ ID NO: 16.

According to some specific embodiments the isolated monoclonal antibody or fragment comprises a set of six CDR sequences consisting of: SEQ ID NO: 4, SEQ ID NO: 6, SEQ ID NO: 8, SEQ ID NO: 12, SEQ ID NO: 14, and SEQ ID NO: 16.

According to other specific embodiments the isolated monoclonal antibody or fragment comprises a set of six CDR sequences consisting of: SEQ ID NO: 80, SEQ ID NO: 81, SEQ ID NO: 82, SEQ ID NO: 12, SEQ ID NO: 14, and SEQ ID NO: 16.

According to some embodiments, the isolated monoclonal antibody or fragment thereof comprises heavy chain variable region set forth in SEQ ID NO: 69), or an analog or derivative thereof having at least 90% sequence identity with the heavy chain variable region sequence.

According to some embodiments, the analog of SEQ ID NO: 2 is heavy chain variable region having a sequence set forth in SEQ ID NO: 69.

According to some embodiments, the isolated monoclonal antibody or fragment thereof comprises light chain variable region set forth in SEQ ID NO: 71), or an analog thereof having at least 90% sequence identity with the light chain variable region sequence.

According to some embodiments, the analog of SEQ ID NO: 10 is light chain variable region having a sequence set forth in SEQ ID NO: 71.

According to a specific embodiment, the isolated monoclonal antibody or fragment thereof comprises a heavy chain variable region having a sequence set forth in SEQ ID NO: 2 or SEQ ID NO: 69, and a light chain variable region having a sequence set forth in SEQ ID NO: 10 or SEQ ID NO: 71, or an analog thereof having at least 90% sequence identity with the light and/or heavy chain sequence.

The invention also encompasses antibody or antibody fragment capable of binding with high affinity to an epitope within the human PVR protein to which monoclonal antibody (mAb) 4E5 binds.

According to other embodiments, the isolated monoclonal antibody comprises the CDR sequences of a monoclonal antibody denoted 7D4 (or hPVR.01), namely, the three CDR sequences contained in heavy chain variable region set forth in SEQ ID NO: 73 and the three CDR sequences contained in light chain variable region set forth in SEQ ID NO: 75.

According to some embodiments, the isolated monoclonal antibody or the antibody fragment comprises heavy-chain CDR1 comprising the sequence GYTFTEYTMH (SEQ ID NO: 20). According to some embodiments, the isolated monoclonal antibody or the antibody fragment comprises heavy-chain CDR2 comprising the sequence GIDPNNGGTNYNQNFKG (SEQ ID NO: 22). According to some embodiments, the isolated monoclonal antibody or the antibody fragment comprises heavy-chain CDR3 comprising the sequence VIPLEY (SEQ ID NO: 24). According to certain embodiments, the isolated monoclonal antibody or the antibody fragment comprises: (i) HC CDR1 comprises the sequence GYTFTEYTMH (SEQ ID NO: 20); (ii) HC CDR2 comprises the sequence: GIDPNNGGTNYNQNFKG (SEQ ID NO: 22); and (iii) HC CDR3 comprises the sequence: VIPLEY (SEQ ID NO: 24).

According to some embodiments, the isolated monoclonal antibody or the antibody fragment comprises heavy-chain CDR1 comprising the sequence EYTMH (SEQ ID NO: 83).

According to some embodiments, the isolated monoclonal antibody or the antibody fragment comprises light-chain CDR1 comprising the sequence KASQNVYTNVA (SEQ ID NO: 28). According to some embodiments, the isolated monoclonal antibody or the antibody fragment comprises light-chain CDR2 comprising the sequence SASYRYR (SEQ ID NO: 30). According to some embodiments, the isolated monoclonal antibody or the antibody fragment comprises light-chain CDR3 comprising the sequence QQYNSYPLA (SEQ ID NO: 32). According to certain embodiments, the isolated monoclonal antibody or the antibody fragment comprises: (i) LC CDR1 comprises the sequence KASQNVYTNVA (SEQ ID NO: 28); (ii) LC CDR2 comprises the sequence: SASYRYR (SEQ ID NO: 30); and (iii) HC CDR3 comprises the sequence: QQYNSYPLA (SEQ ID NO: 32).

According to some specific embodiments the isolated monoclonal antibody comprises heavy chain CDR1 comprising the sequence GYTFTEYTMH (SEQ ID NO: 20), heavy chain CDR2 comprising the sequence: GIDPNNGGTNYNQNFKG (SEQ ID NO: 22), heavy chain CDR3 comprising the sequence: VIPLEY (SEQ ID NO: 24), light chain CDR1 comprising the sequence: KASQNVYTNVA (SEQ ID NO: 28), light chain CDR2 comprising the sequence: SASYRYR (SEQ ID NO: 30), and light chain CDR3 comprising the sequence: QQYNSYPLA (SEQ ID NO: 32), or analogs thereof comprising no more than 5% amino acid substitution, deletion and/or insertion in the HVR sequence.

According to some specific embodiments the isolated monoclonal antibody or fragment comprises a set of six CDR sequences consisting of: heavy chain CDR1 having a sequence selected from the group consisting of SEQ ID NO: 20 and SEQ ID NO: 83, heavy chain CDR2 having a sequence set forth in SEQ ID NO: 22, heavy chain CDR3 having a sequence set forth in SEQ ID NO: 24, light chain CDR1 having a sequence set forth in SEQ ID NO: 28, light chain CDR2 having a sequence set forth in SEQ ID NO: 30, and light chain CDR3 having a sequence set forth in SEQ ID NO: 32.

According to some specific embodiments the isolated monoclonal antibody or fragment comprises a set of six CDR sequences consisting of: SEQ ID NO: 20, SEQ ID NO: 22, SEQ ID NO: 24, SEQ ID NO: 28, SEQ ID NO: 30, and SEQ ID NO: 32.

According to other specific embodiments the isolated monoclonal antibody or fragment comprises a set of six CDR sequences consisting of: SEQ ID NO: 83, SEQ ID NO: 22, SEQ ID NO: 24, SEQ ID NO: 28, SEQ ID NO: 30, and SEQ ID NO: 32.

According to some embodiments, the isolated monoclonal antibody or fragment thereof comprises heavy chain variable region set forth in SEQ ID NO: 73, or an analog or derivative thereof having at least 90% sequence identity with the heavy chain variable region sequence.

According to some embodiments, the analog of SEQ ID NO: 18 is heavy chain variable region having a sequence set forth in SEQ ID NO: 73.

According to some embodiments, the isolated monoclonal antibody or fragment thereof comprises light chain variable region set forth in SEQ ID NO: 75, or an analog thereof having at least 90% sequence identity with the light chain variable region sequence.

According to some embodiments, the analog of SEQ ID NO: 26 is light chain variable region having a sequence set forth in SEQ ID NO: 75.

According to a specific embodiment, the isolated monoclonal antibody or fragment thereof comprises a heavy chain variable region having a sequence set forth in SEQ ID NO: 18 or SEQ ID NO: 73, and a light chain variable region having a sequence set forth in SEQ ID NO: 26 or SEQ ID NO: 75, or an analog thereof having at least 90% sequence identity with the light and/or heavy chain sequence.

The invention also encompasses antibody or antibody fragment capable of binding with high affinity to an epitope within the human PVR protein to which mAb 7D4 binds.

According to other embodiments, the isolated monoclonal antibody comprises the CDR sequences of a monoclonal antibody denoted 5B9 (or hPVR.09), namely, the three CDR sequences contained in heavy chain variable region set forth in SEQ ID NO: 77 and the three CDR sequences contained in light chain variable region set forth in SEQ ID NO: 79.

According to some embodiments, the isolated monoclonal antibody comprises the complementarity determining region (CDR) sequences contained in heavy chain variable region set forth in SEQ ID NO: 34 and the three CDR sequences contained in light chain variable region sequence selected from the group consisting of SEQ ID NO: 42, SEQ ID NO: 49, SEQ ID NO: 50, SEQ ID NO: 51, SEQ ID NO: 52, SEQ ID NO: 53, and SEQ ID NO: 54. Each possibility represents a separate embodiment of the invention.

According to some embodiments, the isolated monoclonal antibody or the antibody fragment comprises heavy-chain CDR1 comprising the sequence GYTFSNYWIE (SEQ ID NO: 36). According to some embodiments, the isolated monoclonal antibody or the antibody fragment comprises heavy-chain CDR2 comprising the sequence EIFPGSGRINFNEKFKG (SEQ ID NO: 38). According to some embodiments, the isolated monoclonal antibody or the antibody fragment comprises heavy-chain CDR3 comprising the sequence TKIYGNSFDY (SEQ ID NO: 40). According to some embodiments, the isolated monoclonal antibody or the antibody fragment comprises heavy-chain CDR1 comprising the sequence SNYWIE (SEQ ID NO: 84).

According to certain embodiments, the isolated monoclonal antibody or the antibody fragment comprises: (i) HC CDR1 comprises the sequence SNYWIE (SEQ ID NO: 84); (ii) HC CDR2 comprises the sequence: EIFPGSGRINFNEKFKG (SEQ ID NO: 38); and (iii) HC CDR3 comprises the sequence: TKIYGNSFDY (SEQ ID NO: 40).

According to some embodiments, the isolated monoclonal antibody or the antibody fragment comprises light-chain CDR1 comprising the sequence KASQDVGTAVV (SEQ ID NO: 44). According to some embodiments, the isolated monoclonal antibody or the antibody fragment comprises light-chain CDR2 comprising the sequence WASSRHN (SEQ ID NO: 46). According to some embodiments, the isolated monoclonal antibody or the antibody fragment comprises light-chain CDR3 comprising the sequence QQYSRYPLT (SEQ ID NO: 48).

According to some embodiments, the isolated monoclonal antibody or the antibody fragment comprises light-chain CDR1 comprising the sequence KASQDVGTAV (SEQ ID NO: 85).

According to certain embodiments, the isolated monoclonal antibody or the antibody fragment comprises: (i) LC CDR1 comprises the sequence KASQDVGTAV (SEQ ID NO: 85); (ii) LC CDR2 comprises the sequence: WASSRHN (SEQ ID NO: 46); and (iii) HC CDR3 comprises the sequence: QQYSRYPLT (SEQ ID NO: 48).

According to additional embodiments, LC CDR2 comprises the sequence set forth in SEQ ID Nos: 46, 56, 57, 58, 59, 60, or 61. Each possibility represents a separate embodiment of the invention.

According to some specific embodiments the isolated monoclonal antibody or fragment comprises heavy chain CDR1 sequence comprising the sequence: GYTFSNYWIE (SEQ ID NO: 36), heavy chain CDR2 comprising the sequence: EIFPGSGRINFNEKFKG (SEQ ID NO: 38), heavy chain CDR3 comprising the sequence: TKIYGNSFDY (SEQ ID NO: 40), light chain CDR1 comprising the sequence: KASQDVGTAVV (SEQ ID NO: 44), light chain CDR2 comprising the sequence: WASSRHN (SEQ ID NO: 46), and light chain CDR3 comprising the sequence: QQYSRYPLT (SEQ ID NO: 48), or analogs thereof comprising no more than 5% amino acid substitution, deletion and/or insertion in the HVR sequence.

According to some specific embodiments the isolated monoclonal antibody or fragment consisting of: heavy chain CDR1 having a sequence selected from the group consisting of SEQ ID NO: 36 and SEQ ID NO: 84, heavy chain CDR2 having a sequence set forth in SEQ ID NO: 38, heavy chain CDR3 having a sequence set forth in SEQ ID NO: 40, light chain CDR1 having a sequence selected from the group consisting of SEQ ID NO: 44 and SEQ ID NO: 85, light chain CDR2 having a sequence set forth in SEQ ID NO: 46, and light chain CDR3 having a sequence set forth in SEQ ID NO: 48.

According to some specific embodiments the isolated monoclonal antibody or fragment consisting of: heavy chain CDR1 having a sequence set forth in SEQ ID NO: 36 or SEQ ID NO: 84, heavy chain CDR2 having a sequence set forth in SEQ ID NO: 38, heavy chain CDR3 having a sequence set forth in SEQ ID NO: 40, light chain CDR1 having a sequence set forth in SEQ ID NO: 44 or SEQ ID NO: 85, light chain CDR2 having a sequence selected from the group consisting of: SEQ ID NO: 46, SEQ ID NO: 56, SEQ ID NO: 57, SEQ ID NO: 58, SEQ ID NO: 59, SEQ ID NO: 60, and SEQ ID NO: 61; and light chain CDR3 having a sequence set forth in SEQ ID NO: 48. Each possibility represents a separate embodiment of the invention.

According to some embodiments, the isolated monoclonal antibody or fragment thereof comprises heavy chain variable region set forth in SEQ ID NO: 77, or an analog or derivative thereof having at least 90% sequence identity with the heavy chain variable region sequence According to some embodiments, the analog of SEQ ID NO: 34 is heavy chain variable region having a sequence set forth in SEQ ID NO: 77.

According to some embodiments, the isolated monoclonal antibody or fragment thereof comprises light chain variable region set forth in SEQ ID NO: 79, or an analog thereof having at least 90% sequence identity with the light chain variable region sequence.

According to some embodiments, the analog of SEQ ID NO: 42 is light chain variable region having a sequence set forth in SEQ ID NO: 79.

According to a specific embodiment, the isolated monoclonal antibody or fragment thereof comprises a heavy chain variable region having a sequence selected from the group consisting of SEQ ID NO: 34 and SEQ ID NO: 77, and a light chain variable region having a sequence selected from the group consisting of SEQ ID NO: 42 and SEQ ID NO: 79, or an analog thereof having at least 90% sequence identity with the light and/or heavy chain sequence.

According to some embodiments, the isolated monoclonal antibody or fragment thereof comprises a heavy chain variable region having the sequence set forth in SEQ ID NO: 34, and a light chain variable region having the sequence set forth in SEQ ID NO: 42, SEQ ID NO: 49, SEQ ID NO: 50, SEQ ID NO: 51, SEQ ID NO: 52, SEQ ID NO: 53, or SEQ ID NO: 54; or an analog thereof having at least 90% sequence identity with the light and/or heavy chain sequence. Each possibility represents a separate embodiment of the invention The invention also encompasses antibody or antibody fragment capable of binding with high affinity to an epitope within the human PVR protein to which mAb 5B9 binds.

According to some embodiments, the isolated antibody or fragment thereof recognizes human PVR with an affinity of at least $10^{-8}$M. According to other embodiments, an antibody or antibody fragment binds with an affinity of $10^{-8}$ M, $5\times10^{-9}$M, $10^{-9}$M, $5\times10^{-10}$ M, $10^{-10}$ M, $5\times10^{-11}$M or even higher to human PVR. Each possibility represents a separate embodiment of the invention.

Analogs and derivatives of the isolated mAb antibodies, and the antibody fragments described above, are also within the scope of the invention. In some embodiments, particular analogs or isolated mAbs or fragment thereof comprising at least one variable region set forth in a sequence selected from the group consisting of: SEQ ID NOs: 2, 10, 18, 26, 34 and 42 are also within the scope of the present invention. Isolated mAbs or fragment thereof comprising at least one variable region set forth in a sequence selected from the group consisting of: SEQ ID NOs: 69, 71, 73, 75, 77 and 79 are also within the scope of the present invention.

According to some embodiments, the antibody or antibody fragment analog have at least 90% sequence identity with the hypervariable region of the reference antibody sequence.

According to certain embodiments, the analog or derivative of the isolated antibody or fragment thereof has at least 91, 92, 93, 94, 95, 96, 97, 98 or 99% sequence identity with a variable region of the reference antibody sequence. Each possibility represents a separate embodiment of the invention.

According to some embodiments, the antibody or antibody fragment according to the invention comprises a heavy chain variable region set forth in SEQ ID NO: 2 or SEQ ID NO: 69, or an analog having at least 95% sequence similarity with said sequence. According to other embodiments, the antibody or antibody fragment according to the invention comprises a heavy chain variable region set forth in SEQ ID NO: 18 or SEQ ID NO: 73, or an analog having at least 95% sequence similarity with said sequence. According to other embodiments, the antibody or antibody fragment according to the invention comprises a heavy chain variable region set forth in SEQ ID NO: 34 or SEQ ID NO: 77, or an analog having at least 95% sequence similarity with said sequence.

According to some embodiments, the antibody or antibody fragment comprises a light chain variable region set forth in SEQ ID NO: 10 or SEQ ID NO: 71, or an analog having at least 95% sequence similarity with said sequence. According to other embodiments, the antibody or antibody fragment comprises a light chain variable region set forth in SEQ ID NO: 26 or SEQ ID NO: 75, or an analog having at least 95% sequence similarity with said sequence. According to other embodiments, the antibody or antibody fragment comprises a light chain variable region set forth in SEQ ID NO: 42 or SEQ ID NO: 79, or an analog having at least 95% sequence similarity with said sequence.

According to some embodiments, the antibody or antibody fragment comprises a heavy chain and a light chain, wherein: (i) the heavy chain comprises SEQ ID NO: 2 and the light chain comprises SEQ ID NO: 10; (ii) the heavy chain comprises SEQ ID NO: 18 and the light chain comprises SEQ ID NO: 26; or (iii) the heavy chain comprises SEQ ID NO: 34 and the light chain comprises SEQ ID NO: 42. Analogs of the antibodies or fragments, having at least 95% sequence similarity with said heavy or light chains are also included.

According to other embodiments, the antibody or antibody fragment comprises a heavy chain and a light chain, wherein: (i) the heavy chain comprises SEQ ID NO: 69 and the light chain comprises SEQ ID NO: 71; (ii) the heavy chain comprises SEQ ID NO: 73 and the light chain comprises SEQ ID NO: 75; or (iii) the heavy chain comprises SEQ ID NO: 77 and the light chain comprises SEQ ID NO: 79. Analogs of the antibodies or fragments, having at least 95% sequence similarity with said heavy or light chains are also included.

According to some embodiments, the analog has at least 96, 97, 98 or 99% sequence identity with an antibody light or heavy chain variable regions described above. According to some embodiments, the analog comprises no more than one amino acid substitution, deletion or addition to one or more CDR sequences of the hypervariable region, namely, any one of the CDR sequences set forth in SEQ ID NOs: 4, 6, 8, 12, 14, 16, 20, 22, 24, 28, 30, 32, 36, 38, 40, 44, 46, 48, 80, 81, 82, 83, 84, and 85. Each possibility represents a separate embodiment of the present invention. According to some embodiments, the amino acid substitution is a conservative substitution.

According to some embodiments, the antibody or antibody fragment comprises a hypervariable region (HVR) having light and heavy chain regions defined above, in which 1, 2, 3, 4, or 5 amino acids were substituted, deleted and/or added. Each possibility represents a separate embodiment of the invention.

According to some embodiments, the antibody or antibody fragment comprises a HVR having light and heavy chain regions defined above, in which one amino acid was substituted. According to specific embodiments, the antibody or antibody fragment comprises a CDR as defined above, in which one amino acid was substituted. According to some specific embodiments, the antibody or antibody fragment comprises a light chain CDR2 as defined above, in which one amino acid was substituted.

According to some specific embodiments, the antibody or antibody fragment comprises a light chain CDR2 having a sequence set forth in SEQ ID NO: 55 (WASSRHX), wherein X is selected from the group consisting of A, R, D, E, P, and T. Each possibility represents a separate embodiment of the invention.

According to some embodiments, the antibody or antibody fragment comprises a light chain CDR2 having a sequence selected from the group consisting of SEQ ID NO: 56-61.

According to some embodiments, the isolated monoclonal antibody or the antibody fragment comprises a CDR set selected from the group consisting of:
  i. a CDR set of six CDRs wherein: HC CDR1 is selected from GYTFSNYWIE (SEQ ID NO: 36) and SNYWIE (SEQ ID NO: 84); HC CDR2 is EIFPGSGRINFNEKFKG (SEQ ID NO: 38); HC CDR3 is TKIYGNSFDY (SEQ ID NO: 40); LC CDR1 is selected from KASQDVGTAVV (SEQ ID NO: 44) and KASQDVGTAV (SEQ ID NO: 85); LC CDR2 is selected from the group consisting of: WASSRHN (SEQ ID NO: 46), WASSRHA (SEQ ID NO: 56), WASSRHR (SEQ ID NO: 57), WASSRHD (SEQ ID NO: 58), WASSRHE (SEQ ID NO: 59), WASSRHP (SEQ ID NO: 60), and WASSRHT (SEQ ID NO: 61); and LC CDR3 is QQYSRYPLT (SEQ ID NO: 48).
  ii. a CDR set of six CDRs wherein: HC CDR1 sequence is selected from GFDFSRYW (SEQ ID NO: 4) and RYWMT (SEQ ID NO: 80); HC CDR2 is selected from EIHPDSSKINYTPSQ (SEQ ID NO: 6) and EIHPDSSKINYTPSQKD (SEQ ID NO: 81); HC CDR3 is selected from PDGNYNALDYW (SEQ ID NO: 8) and PDGNYNALDY (SEQ ID NO: 82); LC CDR1 is KASQDVGTAVT (SEQ ID NO: 12); LC CDR2 is WASTRHT (SEQ ID NO: 14); and LC CDR3 is QQYSRYPYT (SEQ ID NO: 16).
  iii. a CDR set of six CDRs wherein: HC CDR1 sequence is selected from the GYTFTEYTMH (SEQ ID NO: 20) and EYTMH (SEQ ID NO: 83); HC CDR2 is GIDPNNGGTNYNQNFKG (SEQ ID NO: 22); HC CDR3 is VIPLEY (SEQ ID NO: 24); LC CDR1 is KASQNVYTNVA (SEQ ID NO: 28); LC CDR2 is SASYRYR (SEQ ID NO: 30); and LC CDR3 is QQYNSYPLA (SEQ ID NO: 32).

The present invention thus provides a monoclonal antibody that specifically binds the human protein PVR, or a binding fragment thereof, wherein said monoclonal antibody or fragment comprises a set of six CDR sequences wherein the set is selected from the group consisting of:
  i. SEQ ID NOs. 4, 6, 8, 12, 14 and 16;
  ii. SEQ ID NOs. 20, 22, 24, 28, 30 and 32;
  iii. SEQ ID NOs. 36, 38, 40, 44, 46 and 48;
  iv. SEQ ID NOs. 36, 38, 40, 44, 55 and 48;
  v. SEQ ID NOs. 80, 81, 82, 12, 14 and 16;
  vi. SEQ ID NOs. 83, 22, 24, 28, 30 and 32;
  vii. SEQ ID NOs. 84, 38, 40, 85, 46 and 48; and
  viii. SEQ ID NOs. 84, 38, 40, 85, 55 and 48.

The present invention also provides monoclonal antibodies and binding fragments thereof, comprising a heavy chain and a light chain, wherein said chains comprises a set of heavy chain variable region sequence and light chain variable region sequence, said set is selected from the group consisting of:
  i. SEQ ID NOs: 2 and 10;
  ii. SEQ ID NOs: 69 and 71;
  iii. SEQ ID NOs: 18 and 26;
  iv. SEQ ID NOs: 73 and 75;
  v. SEQ ID NOs: 34 and 42; and
  vi. SEQ ID NOs: 77 and 79.

According to some embodiments, the antibody or antibody fragment is capable of inhibiting human PVR binding to TIGIT expressed on T cells or NK cells.

According to a specific embodiment, the mAb is selected from the group consisting of: chimeric antibody, and an antibody fragment comprising at least the antigen-binding portion of an antibody. According to specific embodiments, the antibody is a chimeric antibody.

According to yet other embodiments, the chimeric antibody comprised human constant region. According to yet other embodiments, the chimeric monoclonal antibody comprises human IgG1 constant region. According to a specific embodiment, the antibody fragment is selected from the group consisting of: Fab, Fab', F(ab')$_2$, Fd, Fd', Fv, dAb, isolated CDR region, single chain antibody (scab), "diabodies", and "linear antibodies". Each possibility represents a separate embodiment of the present invention.

According to some embodiments, the antibody or antibody fragment comprises a framework sequence selected from the group consisting of: mouse IgG2a, mouse IgG2b, mouse IgG3, human IgG1, human IgG2, human IgG3, and human IgG4. Each possibility represents a separate embodiment of the present invention.

According to some embodiments, a conjugate comprising the antibody or fragment thereof as described above is provided.

According to some embodiments, the conjugate comprises a carrier protein.

Polynucleotide sequences encoding monoclonal antibodies, having high affinity and specificity for PVR, as well as vectors and host cells carrying these polynucleotide sequences, are provided according to another aspect of the present invention.

According to some embodiments, polynucleotide sequences encoding the amino acid sequences of HC variable region and light LC variable region described above are provided.

According to some embodiments, the polynucleotide sequence encodes an antibody or antibody fragment or chain capable of binding to an epitope within the human PVR protein to which binds: (i) a monoclonal antibody (herein identified as 4E5) having a heavy chain variable region of SEQ ID NO: 2 and a light chain variable region of SEQ ID NO: 10; (ii) a monoclonal antibody (herein identified as 7D4) having a heavy chain variable region of SEQ ID NO:18 and a light chain variable region of SEQ ID NO: 26; or (iii) a monoclonal antibody (herein identified as 5B9) having a heavy chain variable region of SEQ ID NO: 34 and a light chain variable region of SEQ ID NO: 42.

According to some embodiments, the polynucleotide sequence encodes an antibody or antibody fragment or chain comprising the sequence set forth in SEQ ID NO: 2 or SEQ ID NO: 69. According to some embodiments, the polynucleotide sequence encodes an antibody or antibody fragment or chain comprising the sequence set forth in SEQ ID NO: 10 or SEQ ID NO: 71.

According to other embodiments, the polynucleotide sequence encodes an antibody or antibody fragment or chain comprising the sequence set forth in SEQ ID NO: 18 or SEQ ID NO: 73. According to additional embodiments, the polynucleotide sequence encodes an antibody or antibody fragment or chain comprising the sequence set forth in SEQ ID NO: 26 or SEQ ID NO: 75.

According to other embodiments, the polynucleotide sequence encodes an antibody or antibody fragment or chain comprising the sequence set forth in SEQ ID NO: 34 or SEQ ID NO: 77. According to additional embodiments, the polynucleotide sequence encodes an antibody or antibody fragment or chain comprising the sequence set forth in SEQ ID NO: 42 or SEQ ID NO: 79.

According to yet some embodiments, the polynucleotide sequence according to the invention encodes an antibody or antibody fragment or chain comprising the six CDR sequences: (i) heavy chain CDR1 having the sequence: GFDFSRYW (SEQ ID NO: 4) or RYWMT (SEQ ID NO: 80), heavy chain CDR2 having the sequence: EIHPDSSKINYTPSQ (SEQ ID NO: 6), heavy chain CDR3 having the sequence: PDGNYNALDY (SEQ ID NO: 82), light chain CDR1 having the sequence: KASQDVGTAVT (SEQ ID NO: 12), light chain CDR2 having the sequence: WASTRHT (SEQ ID NO: 14), and light chain CDR3 having the sequence: QQYSRYPYT (SEQ ID NO: 16); (ii) heavy chain CDR1 having the sequence EYTMH (SEQ ID NO: 83), heavy chain CDR2 having the sequence: GIDPNNGGTNYNQNFKG (SEQ ID NO: 22), heavy chain CDR3 having the sequence: VIPLEY (SEQ ID NO: 24), light chain CDR1 having the sequence: KASQNVYTNVA (SEQ ID NO: 28), light chain CDR2 having the sequence: SASYRYR (SEQ ID NO: 30), and light chain CDR3 having the sequence: QQYNSYPLA (SEQ ID NO: 32); or (iii) heavy chain CDR1 having the sequence SNYWIE (SEQ ID NO: 84), heavy chain CDR2 having the sequence: EIFPGSGRINFNEKFKG (SEQ ID NO: 38), heavy chain CDR3 having the sequence: TKIYGNSFDY (SEQ ID NO: 40), light chain CDR1 having the sequence: KASQDVGTAV (SEQ ID NO: 85), light chain CDR2 having the sequence: WASSRHN (SEQ ID NO: 46), and light chain CDR3 having the sequence: QQYSRYPLT (SEQ ID NO: 48).

According to some embodiments, the polynucleotide sequences defined above encodes a molecule selected from the group consisting of: an antibody, an antibody fragment comprising at least an antigen-binding portion, and an antibody conjugate comprising said antibody or antibody fragment. Each possibility represents a separate embodiment of the present invention.

According to some embodiments, the polynucleotide sequence encoding a monoclonal antibody heavy chain variable region, comprises a sequence set forth in SEQ ID NO: 1 or SEQ ID NO: 68, or a variant thereof having at least 90% sequence identity.

According to some embodiments, the polynucleotide sequence encoding a monoclonal antibody heavy chain variable region, comprises a sequence set forth in SEQ ID NO: 17 or SEQ ID NO: 72, or a variant thereof having at least 90% sequence identity.

According to some embodiments, the polynucleotide sequence encoding a monoclonal antibody heavy chain variable region, comprises a sequence set forth in SEQ ID NO: 33 or SEQ ID NO: 76, or a variant thereof having at least 90% sequence identity.

According to some embodiments, the polynucleotide sequence encoding a monoclonal antibody light chain variable region, comprises a sequence set forth in SEQ ID NO: 9 or SEQ ID NO: 70, or a variant thereof having at least 90% sequence identity.

According to some embodiments, the polynucleotide sequence encoding a monoclonal antibody light chain variable region, comprises a sequence set forth in SEQ ID NO: 25 or SEQ ID NO: 74, or a variant thereof having at least 90% sequence identity.

According to some embodiments, the polynucleotide sequence encoding a monoclonal antibody light chain variable region, comprises a sequence set forth in SEQ ID NO: 41 or SEQ ID NO: 78, or a variant thereof having at least 90% sequence identity.

The present invention provides, according to some embodiments, a polypeptide comprising at least one sequence encoded by at least one polynucleotide sequence disclosed above.

In a further aspect, the present invention provides a nucleic acid construct comprising a nucleic acid molecule encoding at least one antibody chain or fragment thereof according to the present invention. According to some embodiments the nucleic acid construct is a plasmid.

According to some embodiments the plasmid comprises a polynucleotide sequence set forth in SEQ ID NO: 1, SEQ ID NO: 17, or SEQ ID NO: 33.

According to some embodiments the plasmid comprises a polynucleotide sequence set forth in SEQ ID NO: 68, SEQ ID NO: 72, or SEQ ID NO: 76.

According to other embodiments the plasmid comprises a polynucleotide sequence set forth in SEQ ID NO: 9, SEQ ID NO: 25, or SEQ ID NO: 41.

According to other embodiments the plasmid comprises a polynucleotide sequence set forth in SEQ ID NO: 70, SEQ ID NO: 74, or SEQ ID NO: 78.

In still another aspect the present invention provides a hybridoma cell capable of producing an antibody or an antibody fragment comprising the specific CDR sequences and/or specific heavy and light chain variable regions defined above.

According to some embodiments, a hybridoma cell is provided comprising at least one polynucleotide sequence disclosed above.

According to some embodiments, the hybridoma is a cable of producing a monoclonal antibody comprising the six complementarity determining regions (CDRs) sequences: (i) heavy chain CDR1 having the sequence: GFDFSRYW (SEQ ID NO: 4) or RYWMT (SEQ ID NO: 80), heavy chain CDR2 having the sequence: EIHPDSSKINYTPSQ (SEQ ID NO: 6), heavy chain CDR3 having the sequence: PDGNYNALDY (SEQ ID NO: 82), light chain CDR1 having the sequence: KASQDVGTAVT (SEQ ID NO: 12), light chain CDR2 having the sequence: WASTRHT (SEQ ID NO: 14), and light chain CDR3 having the sequence: QQYSRYPYT (SEQ ID NO: 16); (ii) heavy chain CDR1 having the sequence EYTMH (SEQ ID NO: 83), heavy chain CDR2 having the sequence: GIDPNNGGTNYNQNFKG (SEQ ID NO: 22), heavy chain CDR3 having the sequence: VIPLEY (SEQ ID NO: 24), light chain CDR1 having the sequence: KASQNVYTNVA (SEQ ID NO: 28), light chain CDR2 having the sequence: SASYRYR (SEQ ID NO: 30), and light chain CDR3 having the sequence: QQYNSYPLA (SEQ ID NO: 32); or (iii) heavy chain CDR1 having the sequence SNYWIE (SEQ ID NO: 84), heavy chain CDR2 having the sequence: EIFPGSGRINFNEKFKG (SEQ ID NO: 38), heavy chain CDR3 having the sequence: TKIYGNSFDY (SEQ ID NO: 40), light chain CDR1 having the sequence: KASQDVGTAV (SEQ ID NO: 85), light chain CDR2 having the sequence: WASSRHN (SEQ ID NO: 46), and light chain CDR3 having the sequence: QQYSRYPLT (SEQ ID NO: 48).

Antibodies or fragments thereof according to the present invention may be attached to a cytotoxic moiety, a radioactive moiety, or an identifiable moiety.

The present invention provides, according to another aspect, a pharmaceutical composition comprising as an active ingredient, at least one antibody, antibody fragment or conjugates thereof, that recognizes PVR with high affinity and specificity, and optionally at least one pharmaceutical acceptable excipient, diluent, salt or carrier.

According to some embodiments, the pharmaceutical composition comprises a monoclonal antibody or a fragment thereof which is capable of binding to an epitope within the human PVR protein to which binds a monoclonal antibody selected from the group consisting of: (i) an antibody herein identified as 4E5 (also denoted PVR.07), having a heavy chain variable region of SEQ ID NO: 2 and a light chain variable region of SEQ ID NO: 10; (ii) an antibody herein identified as 7D4 (also denoted PVR.01) having a heavy chain variable region of SEQ ID NO: 18 and a light chain variable region of SEQ ID NO: 26; and (ii) an antibody herein identified as 5B9 (also denoted PVR.09) having a heavy chain variable region of SEQ ID NO: 34 and a light chain variable region of SEQ ID NO: 42.

According to some embodiments, the pharmaceutical composition comprises a monoclonal antibody or antibody fragment thereof comprising the six CDRs: (i) heavy chain CDR1 having the sequence: GFDFSRYW (SEQ ID NO: 4) or RYWMT (SEQ ID NO: 80, heavy chain CDR2 having the sequence: EIHPDSSKINYTPSQ (SEQ ID NO: 6), heavy chain CDR3 having the sequence: PDGNYNALDY (SEQ ID NO: 82), light chain CDR1 having the sequence: KASQDVGTAVT (SEQ ID NO: 12), light chain CDR2 having the sequence: WASTRHT (SEQ ID NO: 14), and light chain CDR3 having the sequence: QQYSRYPYT (SEQ ID NO: 16); (ii) heavy chain CDR1 having the sequence EYTMH (SEQ ID NO: 83), heavy chain CDR2 having the sequence: GIDPNNGGTNYNQNFKG (SEQ ID NO: 22), heavy chain CDR3 having the sequence: VIPLEY (SEQ ID NO: 24), light chain CDR1 having the sequence: KASQNVYTNVA (SEQ ID NO: 28), light chain CDR2 having the sequence: SASYRYR (SEQ ID NO: 30), and light chain CDR3 having the sequence: QQYNSYPLA (SEQ ID NO: 32); or (iii) heavy chain CDR1 having the sequence SNYWIE (SEQ ID NO: 84), heavy chain CDR2 having the sequence: EIFPGSGRINFNEKFKG (SEQ ID NO: 38), heavy chain CDR3 having the sequence: TKIYGNSFDY (SEQ ID NO: 40), light chain CDR1 having the sequence: KASQDVGTAV (SEQ ID NO: 85), light chain CDR2 having the sequence: WASSRHN (SEQ ID NO: 46), and light chain CDR3 having the sequence: QQYSRYPLT (SEQ ID NO: 48).

According to some embodiments, the pharmaceutical composition comprises a monoclonal antibody or fragment thereof comprising a heavy chain variable region having a sequence selected from the group consisting of SEQ ID NO: 2, SEQ ID NO: 69, SEQ ID NO: 18, SEQ ID NO: 73, SEQ ID NO: 34, and SEQ ID NO: 77. Each possibility represent a separate embodiment of the invention According to some embodiments, the pharmaceutical composition comprises a monoclonal antibody or fragment thereof comprising a light chain variable region having a sequence selected from the group consisting of SEQ ID NO: 10, SEQ ID NO: 71, SEQ ID NO: 26, SEQ ID NO: 75, SEQ ID NO: 42, and SEQ ID NO: 79. Each possibility represents a separate embodiment of the invention.

According to a specific embodiment, the pharmaceutical composition comprises a monoclonal antibody or fragment thereof comprising a heavy chain variable region having the sequence set forth in SEQ ID NO: 2 or SEQ ID NO: 69 and a light chain variable region having the sequence set forth in SEQ ID NO: 10 or SEQ ID NO: 71.

According to a specific embodiment, the pharmaceutical composition comprises a monoclonal antibody or fragment thereof comprising a heavy chain variable region having the sequence set forth in SEQ ID NO: 18 or SEQ ID NO: 73 and a light chain variable region having the sequence set forth in SEQ ID NO: 26 or DES ID NO: 75.

According to a specific embodiment, the pharmaceutical composition comprises a monoclonal antibody or fragment thereof comprising a heavy chain variable region having the sequence set forth in SEQ ID NO: 34 or SEQ ID NO: 77 and a light chain variable region having the sequence set forth in SEQ ID NO: 42 or SEQ ID NO: 79.

According to some embodiments, the pharmaceutical composition comprises a combination of at least two antibodies, or antibody fragments, which recognizes human PVR.

According to yet other embodiments, the pharmaceutical composition comprises one mAb or fragment that specifically binds PVR according to the invention, and one mAb or fragment that specifically binds a different antigen, such as, cell-receptor, tumor antigen or immunomodulatory protein.

Also provided are pharmaceutical compositions, comprising at least one antibody, antibody fragment or antibody conjugate according to the invention, for use in restoring NK cytotoxicity by inhibiting binding of PVR to TIGIT expressed on NK cells.

According to some embodiments, the antibody, antibody fragment or antibody conjugate is capable of inhibiting human PVR binding to TIGIT expressed on T-cells.

According to some embodiments, the pharmaceutical composition according to the present invention is for use in cancer immunotherapy or in enhancing immune response.

The cancer can be any cancer that express PVR. According to some embodiments, the cancer overexpresses PVR.

According to some embodiments of the invention, the cancer is a metastatic cancer.

According to some embodiments, the pharmaceutical composition according to the present invention is for use in inhibiting formation or distribution of metastases or reducing the total number of metastases in a subject.

According to some embodiments of the invention, the cancer is selected from the group consisting of a melanoma, a breast cancer, an ovarian cancer, a pancreatic cancer, a colorectal cancer, a colon cancer, a cervical cancer, a kidney cancer, a lung cancer, a thyroid cancer, a prostate cancer, a brain cancer, a renal cancer, a throat cancer, a laryngeal carcinoma, a bladder cancer, a hepatic cancer, a fibrosarcoma, an endometrial cells cancer, a glioblastoma, sarcoma, a myeloid, a leukemia and a lymphoma. Each possibility represents a separate embodiment of the invention.

According to some embodiments, the cancer is a solid cancer. According to some specific embodiments, the solid cancer is selected from the group consisting of melanoma (skin), lung, colon, breast, uterine, and renal cancer. According to specific embodiments, the cancer is selected from the group consisting of breast cancer, lung cancer, and liposarcoma.

According to other embodiments, the cancer is hematologic cancer. According to some embodiments, the hematologic cancer is myeloid leukemia, acute lymphoblastic leukemia, chronic lymphocytic leukemia, myeloproliferative diseases, multiple myeloma, or myelodysplastic syndrome. Each possibility represents a separate embodiment of the invention. According to certain embodiments, the cancer is leukemia. According to specific embodiments, the cancer is acute myeloid leukemia (AML).

According to some embodiments, the pharmaceutical composition according to the present invention is for use in treating a viral infection.

According to some embodiments, the viral infection is caused by a virus which binds a target cell via a PVR on a surface of the infected cell.

According to some embodiments, the pharmaceutical composition according to the present invention is for use in treating an angiogenesis-related disease or disorder. According to certain embodiments, the angiogenesis-related disease or disorder is selected from the group consisting of: cancer, cell proliferative diseases of the eye (ocular diseases), retinal disorders, and inflammatory disease. Each possibility represents a separate embodiment of the invention.

According to yet another aspect, the present invention provides a method of inhibiting binding of human PVR to at least one ligand by using a monoclonal antibody or antibody fragment defined above.

According to an additional aspect, the present invention provides a method for enhancing immune response in a subject in need thereof comprising administering to said subject a therapeutically effective amount of a monoclonal antibody, antibody fragment or antibody conjugate defined above.

According to yet another aspect, the present invention provides a method of treating cancer comprising administering to a subject in need thereof, a therapeutically effective amount of a pharmaceutical composition comprising at least one antibody, antibody fragment or conjugate thereof, that recognizes human PVR with high affinity and specificity and capable of inhibiting its binding to its ligand.

According to some embodiments, the antibody in the pharmaceutical composition administered is selected from the group consisting of: (i) a monoclonal antibody comprising the CDR sequences contained in heavy chain variable region set forth in SEQ ID NO: 2 and the CDR sequences contained in light chain variable region set forth in SEQ ID NO: 10; (ii) a monoclonal antibody comprising the CDR sequences contained in heavy chain variable region set forth in SEQ ID NO: 18 and the CDR sequences contained in light chain variable region set forth in SEQ ID NO: 26; or (iii) a monoclonal antibody comprising the CDR sequences contained in heavy chain variable region set forth in SEQ ID NO: 34 and the CDR sequences contained in light chain variable region set forth in SEQ ID NO: 42.

According to some specific embodiments, the monoclonal antibody in the pharmaceutical composition administered comprises: heavy chain CDR1 comprises the sequence selected from the group consisting of GFDFSRYW (SEQ ID NO: 4) and RYWMT (SEQ ID NO: 80); heavy chain CDR2 comprises the sequence: EIHPDSSKINYTPSQ (SEQ ID NO: 6); heavy chain CDR3 comprises the sequence: PDGNYNALDY (SEQ ID NO: 82); light chain CDR1 comprises the sequence: KASQDVGTAVT (SEQ ID NO: 12); light chain CDR2 comprises the sequence: WASTRHT (SEQ ID NO: 14); and light chain CDR3 comprises the sequence: QQYSRYPYT (SEQ ID NO: 16). Each possibility represents a separate embodiment of the invention.

According to other specific embodiments, the monoclonal antibody in the pharmaceutical composition administered comprises: heavy chain CDR1 comprises the sequence EYTMH (SEQ ID NO: 83); heavy chain CDR2 comprises the sequence: GIDPNNGGTNYNQNFKG (SEQ ID NO: 22); heavy chain CDR3 comprises the sequence: VIPLEY (SEQ ID NO: 24); light chain CDR1 comprises the sequence: KASQNVYTNVA (SEQ ID NO: 28); light chain CDR2 comprises the sequence: SASYRYR (SEQ ID NO: 30); and light chain CDR3 comprises the sequence: QQYNSYPLA (SEQ ID NO: 32).

According to other specific embodiments, the monoclonal antibody in the pharmaceutical composition administered comprises: heavy chain CDR1 comprises the sequence SNYWIE (SEQ ID NO: 84); heavy chain CDR2 comprises the sequence: EIFPGSGRINFNEKFKG (SEQ ID NO: 38); heavy chain CDR3 comprises the sequence: TKIYGNSFDY (SEQ ID NO: 40); light chain CDR1 comprises the sequence: KASQDVGTAV (SEQ ID NO: 85); light chain CDR2 comprises the sequence: WASSRHN (SEQ ID NO: 46); and light chain CDR3 comprises the sequence: QQYSRYPLT (SEQ ID NO: 48).

According to some embodiments of the invention, the therapeutically effective amount results in a decrease in tumor size or in the number of metastases in the subject.

According to some embodiments, the method of treating cancer comprises administering or performing at least one additional anti-cancer therapy. According to certain embodiments, the additional anticancer therapy is surgery, chemotherapy, radiotherapy, or immunotherapy.

According to some embodiments, the method of treating cancer comprises administration of a monoclonal antibody that recognizes human PVR with high affinity and specificity and an additional anti-cancer agent. According to some embodiments, the additional anti-cancer agent is selected from the group consisting of: immune-modulator, activated lymphocyte cell, kinase inhibitor and chemotherapeutic agent.

According to other embodiments, the additional immune-modulator is an antibody, antibody fragment or antibody conjugate that binds to an antigen other than human PVR.

According to some embodiments, the additional immune-modulator is an antibody against an immune checkpoint molecule. According to some embodiments, the additional immune modulator is an antibody against an immune checkpoint molecule selected from the group consisting of human programmed cell death protein 1 (PD-1), PD-L1 and PD-L2, carcinoembryonic antigen-related cell adhesion molecule 1 (CEACAM1), lymphocyte activation gene 3 (LAG3), CD137, OX40 (also referred to as CD134), killer cell immunoglobulin-like receptors (KIR), TIGIT and any combination thereof. Each possibility represents a separate embodiment of the invention.

According to some embodiments, the anti-cancer agent is selected from the group consisting of: Erbitux, cytarabine, fludarabine, fluorouracil, mercaptopurine, methotrexate, thioguanine, gemcitabine, vincristine, vinblastine, vinorelbine, carmustine, lomustine, chlorambucil, cyclophosphamide, cisplatin, carboplatin, ifosfamide, mechlorethamine, melphalan, thiotepa, dacarbazine, bleomycin, dactinomycin, daunorubicin, doxorubicin, idarubicin, mitomycin, mitoxantrone, plicamycin, etoposide, teniposide and any combination thereof. Each possibility represents a separate embodiment of the invention.

According to some embodiments, the anti-cancer agent is epidermal growth factor receptor (EGFR) inhibitor. According to some embodiments, the EGFR inhibitor is selected from the group consisting of: Cetuximab (Erbitux®), Panitumumab (Vectibix®), and necitumumab (Portrazza®). According to some embodiments, the EGFR inhibitor is Cetuximab (Erbitux®).

According to some embodiments of the invention, the subject is a human subject.

According to some embodiments of the invention, the use further comprises the use of an agent that downregulates the activity or expression of an immune co-inhibitory receptor.

According to some embodiments of the invention, the immune cell is a T cell.

According to some embodiments of the invention, the immune co-inhibitory receptor is selected from the group consisting of PD-1, TIGIT, DNAM-1, CTLA-4, LAG3, TIM3, BTLA, VISTA, B7H4, CD96, BY55, LAIR1, SIGLEC10, and 2B4. Each possibility represents a separate embodiment of the invention.

According to an aspect, the present invention provides a method for modulating immune system function and/or activity comprising modulating the binding of PVR to TIGIT using an antibody according to the invention.

According to an aspect, the present invention provides a method of preventing or treating a viral infection of a virus that utilizes CD155 as an entry receptor, in a subject in need thereof, the method comprises administering to the subject a therapeutically effective amount of an anti PVR monoclonal antibody described herein. According to some embodiments the virus is selected from the group consisting of: polio virus, coxsackie virus, adeno virus and human deficiency virus (HIV).

According to yet another aspect, the present invention provides a method for treating an angiogenesis-related disease or disorder. According to certain embodiments, the angiogenesis-related disease or disorder is selected from the group consisting of: cancer, cell proliferative diseases of the eye (ocular diseases), retinal disorders, and inflammatory disease. Each possibility represents a separate embodiment of the invention.

According to some embodiments, the method of treating cancer involves preventing or reducing formation, growth or spread of metastases in a subject by inhibiting angiogenesis.

According to an aspect, the present invention provides a method of diagnosing or prognosing cancer or infectious disease in a subject, the method comprises determining the expression level of PVR in a biological sample of said subject using at least one antibody as described herein.

The present invention further comprises, according to another aspect, a method of determining or quantifying the expression of PVR, the method comprising contacting a biological sample with an antibody or antibody fragment, and measuring the level of complex formation, wherein the antibody or antibody fragment comprises the complementarity determining regions (CDRs) selected from the group consisting of: (i) heavy chain CDR1 having the sequence: GFDFSRYW (SEQ ID NO: 4) or RYWMT (SEQ ID NO: 80), heavy chain CDR2 having the sequence: EIHPDSSKINYTPSQ (SEQ ID NO: 6), heavy chain CDR3 having the sequence: PDGNYNALDY (SEQ ID NO: 82), light chain CDR1 having the sequence: KASQDVGTAVT (SEQ ID NO: 12), light chain CDR2 having the sequence: WASTRHT (SEQ ID NO: 14), and light chain CDR3 having the sequence: QQYSRYPYT (SEQ ID NO: 16); (ii) heavy chain CDR1 having the sequence EYTMH (SEQ ID NO: 83), heavy chain CDR2 having the sequence: GIDPNNGGTNYNQNFKG (SEQ ID NO: 22), heavy chain CDR3 having the sequence: VIPLEY (SEQ ID NO: 24), light chain CDR1 having the sequence: KASQNVYTNVA (SEQ ID NO: 28), light chain CDR2 having the sequence: SASYRYR (SEQ ID NO: 30), and light chain CDR3 having the sequence: QQYNSYPLA (SEQ ID NO: 32); or (iii) heavy chain CDR1 having the sequence SNYWIE (SEQ ID NO: 84), heavy chain CDR2 having the sequence: EIFPGSGRINFNEKFKG (SEQ ID NO: 38), heavy chain CDR3 having the sequence: TKIYGNSFDY (SEQ ID NO: 40), light chain CDR1 having the sequence: KASQDVGTAV (SEQ ID NO: 85), light chain CDR2 having the sequence: WASSRHN (SEQ ID NO: 46), and light chain CDR3 having the sequence: QQYSRYPLT (SEQ ID NO: 48).

Determining and quantifying methods may be performed in-vitro or ex-vivo according to some embodiments or may be used in diagnosing conditions associated with expression of PVR. The antibodies according to the present invention may be also used to configure screening methods. For example, an enzyme-linked immunosorbent assay (ELISA), or a radioimmunoassay (RIA) can be constructed for measuring levels of secreted or cell-associated polypeptide using the antibodies and methods known in the art.

According to some embodiments, the method for detecting or quantifying the presence of PVR comprises the steps of:
  i. incubating a sample with an antibody specific to PVR or an antibody fragment thereof comprising at least an antigen-binding portion;
  ii. detecting the bound PVR using a detectable probe.

According to some embodiments, the method further comprises the steps of:
  iii. comparing the amount of (ii) to a standard curve obtained from a reference sample containing a known amount of PVR; and
  iv. calculating the amount of the PVR in the sample from the standard curve.

According to some particular embodiments the sample is a body fluid.

According to some embodiments, the method is performed in-vitro or ex-vivo.

A kit for measuring the expression of PVR in biological sample is also provided comprising at least one antibody or antibody fragment comprising the complementarity determining regions (CDRs) selected from the group consisting of: (i) heavy chain CDR1 having the sequence: GFDFSRYW (SEQ ID NO: 4) or RYWMT (SEQ ID NO: 80), heavy chain CDR2 having the sequence: EIHPDSSKINYTPSQ (SEQ ID NO: 6), heavy chain CDR3 having the sequence: PDGNYNALDY (SEQ ID NO: 82), light chain CDR1 having the sequence: KASQDVGTAVT (SEQ ID NO: 12), light chain CDR2 having the sequence: WASTRHT (SEQ ID NO: 14), and light chain CDR3 having the sequence: QQYSRYPYT (SEQ ID NO: 16); (ii) heavy chain CDR1 having the sequence EYTMH (SEQ ID NO: 83), heavy chain CDR2 having the sequence: GIDPNNGGTNYNQNFKG (SEQ ID NO: 22), heavy chain CDR3 having the sequence: VIPLEY (SEQ ID NO:24), light chain CDR1 having the sequence: KASQNVYTNVA (SEQ ID NO: 28), light chain CDR2 having the sequence: SASYRYR (SEQ ID NO: 30), and light chain CDR3 having the sequence: QQYNSYPLA (SEQ ID NO: 32); or (iii) heavy chain CDR1 having the sequence SNYWIE (SEQ ID NO: 84), heavy chain CDR2 having the sequence: EIFPGSGRINFNEKFKG (SEQ ID NO: 38), heavy chain CDR3 having the sequence: TKIYGNSFDY (SEQ ID NO: 40), light chain CDR1 having the sequence: KASQDVGTAV (SEQ ID NO: 85), light chain CDR2 having the sequence: WASSRHN (SEQ ID NO: 46), and light chain CDR3 having the sequence: QQYSRYPLT (SEQ ID NO: 48).

According to an aspect, the present invention provides a kit for detecting cancer, the diagnostic kit comprises an antibody of fragment thereof as disclosed herein.

According to some embodiments, the invention provides a method of diagnosing, assessing the severity or staging an immune-related disease or a proliferative disease comprising determining the expression or activity of PVR in a sample from a subject using an antibody according to the present invention or a fragment or conjugate thereof, and comparing the expression or activity of PVR to a reference amount of PVR expression or activity. Said reference amount may be obtained from a sample taken from a normal subject, from the same subject while being in a different stage of the disease or is determined from clinical data of a large population of subjects.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 3A illustrates a non-blocking anti-PVR antibody (anti-PVR mAb antibody 2G3, also termed hPVR.17). FIGS. 3B-3D show that three of the antibodies generated, namely 5B9 (also termed hPVR.09), 7D4 (also termed hPVR.01) and 4E5 (also termed hPVR.07), respectively, are anti-PVR blocking mAbs as shown by blockage of TIGIT-Ig binding. Hybridomas soups (5 µl of/well) were added to HepG2 cells. TIGIT-Fc was used at 2 µg/well to final concentration of 20 µg/ml and levels of cell bound TIGIT were measured by FACS after adding fluorescently labeled anti-Fc Ab. Filled histograms depict background staining by the anti-Fc reagent.

FIGS. 7A-7D are graphs of FACS analysis depicting that PVR is the main TIGIT ligand. FIG. 7A illustrates that HepG2 cells (human hepatocellular carcinoma cells) express PVR and Nectin-2. FIG. 7B illustrates that purified anti-PVR mAb 4E5 (also termed hPVR.07) (0.15 µg) almost completely (above 97%) blocks TIGIT-Ig (2 µg/ml) binding, despite the fact that these cells also express Nectin-2. FIG. 7C illustrates that CHO cells express high levels of hNectin-2. FIG. 7D shows lack of staining of the same CHO cells as in FIG. 7C by all PVR mAbs, meaning that there is no direct recognition of Nectin-2 by anti-PVR mAbs, and thus the blocking of TIGIT binding seen in FIG. 7B cannot be explained by blocking of Nectin-2 but rather it is the result of a direct PVR blocking.

FIG. 10A illustrates binding of TIGIT-Fc to Nectin2 expressing cells; FIG. 10B illustrates binding of DNAM-FC to Nectin-2 expressing cells. FIG. 10C illustrates binding of TIGIT to PVR expressing cells. FIG. 10D illustrates binding of DNAM-1 to PVR expressing cells.

DETAILED DESCRIPTION OF THE INVENTION

Figure 1A:
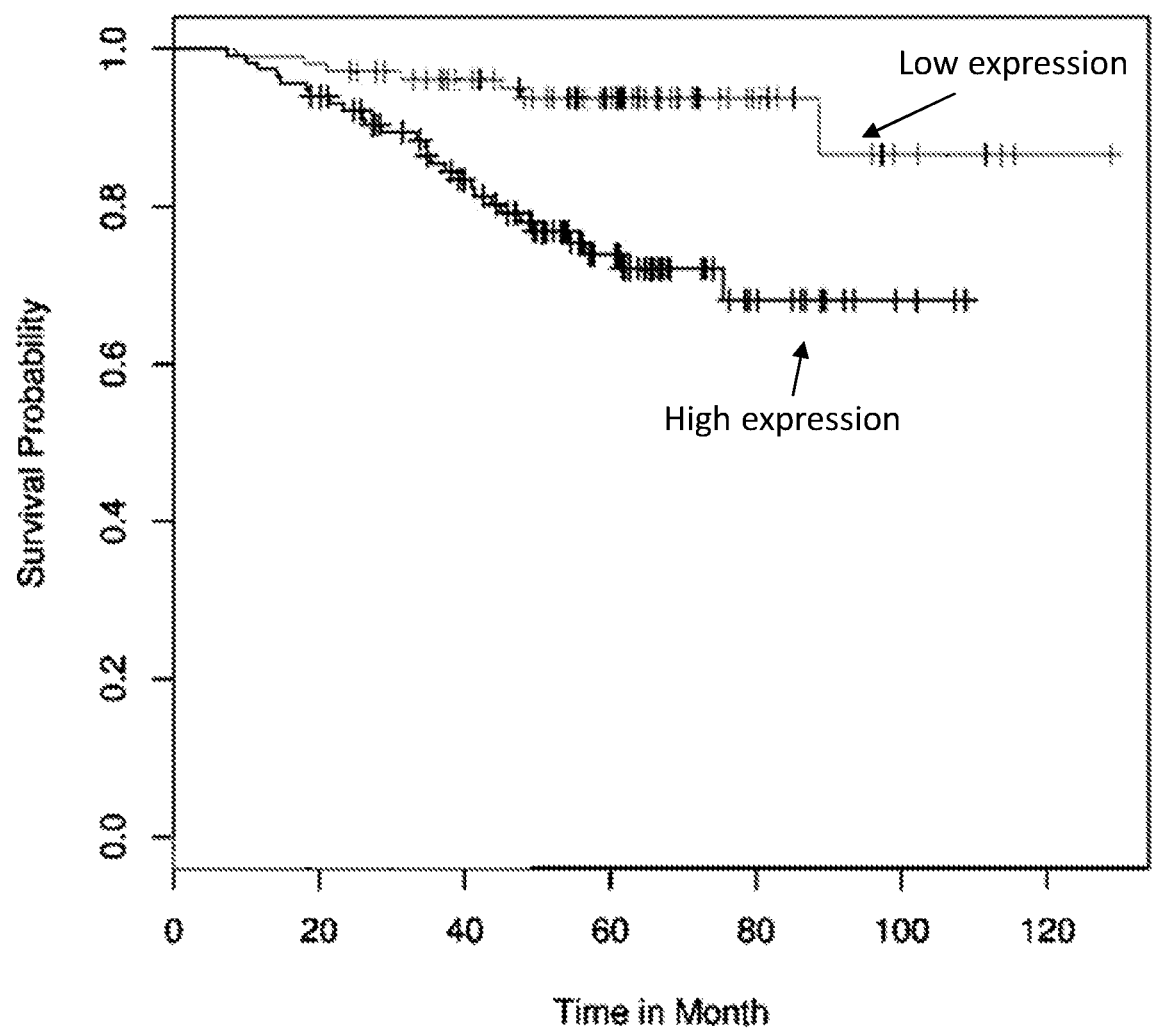
FIGS. 1A-1C are graphs depicting the correlation of PVR mRNA expression levels (high or low as indicated) with survival probability. The correlation was measured for lung cancer (FIG. 1A), breast cancer (FIG. 1B) and liposarcoma (FIG. 1C). Data sets of mRNA expression were obtained from the GEO site and analyzed using bioprofiling.de site, as follows: for lung cancer GEO dataset ID: GSE31210, for breast cancer GEO dataset ID: GSE25055 and for liposarcoma GEO dataset ID: GSE30929.

The present invention provides monoclonal antibodies specific to the human poliovirus receptor (PVR). The invention also provides production and use of the mAbs as therapeutic agents. In particular, the mAbs of the present invention may be used, alone or in combination with other agents, for restoring and augmenting anti-tumor killing activity of immune cells, and as diagnostic reagents.

The term "antigen" as used herein refers to a molecule or a portion of a molecule capable of eliciting antibody formation and being specifically bound by an antibody. An antigen may have one or more than one epitope. The specific binding referred to above is meant to indicate that the antigen will react, in a highly selective manner, with its corresponding antibody and not with the multitude of other antibodies which may be evoked by other antigens. An antigen according to some embodiments of the present invention is a PVR protein.

The term "PVR" as used herein refers to the poliovirus receptor, also known as CD155 (cluster of differentiation 155). The PVR is a transmembrane glycoprotein with a N-terminal signal sequence, three extracellular immunoglobulin (Ig)-like domains, a transmembrane domain and a cytoplasmic tail. It has a molecular size of approximately 80 kDa and a structure composed of three Ig-like domains, specifically an outermost V-like domain followed by two C2-like domains. An exemplary PVR according to the invention is set forth in GenBank accession numbers: NP_001129240.1, NP_001129241.1, NP_001129242.2 and NP_006496.4. These poliovirus receptors share the sequence of the extracellular domain and therefore can be targeted by the affinity binding moiety of the invention.

The term "antigenic determinant" or "epitope" as used herein refers to the region of an antigen molecule that specifically reacts with a particular antibody. Peptide sequences derived from an epitope can be used, alone or in conjunction with a carrier moiety, applying methods known in the art, to immunize animals and to produce additional polyclonal or monoclonal antibodies. Isolated peptides derived from an epitope may be used in diagnostic methods to detect antibodies.

It should be noted that the affinity can be quantified using known methods such as, Surface Plasmon Resonance (SPR) (described in Scarano S, Mascini M, Turner A P, Minunni M. Surface plasmon resonance imaging for affinity-based biosensors. Biosens Bioelectron. 2010, 25: 957-66), and can be calculated using, e.g., a dissociation constant, Kd, such that a lower Kd reflects a higher affinity.

The antibodies or a fragment thereof according to the invention binds to an epitope in hPVR. Specifically, the antibodies bind to an epitope within amino acids 1-343 of the PVR as set forth in NP_006496.4.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (Fragment crystalline) domains. The antigen binding domains, Fab, include regions where the polypeptide sequence varies. The term F(ab')$_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hyper-variable domains known as complementarity determining regions (CDRs 1-3). These domains contribute specificity and affinity of the antigen-binding site.

CDR identification or determination from a given heavy or light chain variable sequence, is typically made using one of few methods known in the art. For example, such determination is made according to the Kabat (Wu T. T and Kabat E. A., *J Exp Med,* 1970; 132:211-50) and IMGT (Lefranc M-P, et al., *Dev Comp Immunol,* 2003, 27:55-77).

When the term "CDR having a sequence", or a similar term is used, it includes options wherein the CDR comprises the specified sequences and also options wherein the CDR consists of the specified sequence.

The antigen specificity of an antibody is based on the hyper variable region (HVR), namely the unique CDR sequences of both light and heavy chains that together form the antigen-binding site.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ). Both isotypes are found in all antibody classes.

The term "antibody" is used in the broadest sense and includes monoclonal antibodies (including full length or intact monoclonal antibodies), polyclonal antibodies, multivalent antibodies, and antibody fragments long enough to exhibit the desired biological activity, namely binding to human PVR.

Antibody or antibodies according to the invention include intact antibodies, such as polyclonal antibodies or monoclonal antibodies (mAbs), as well as proteolytic fragments thereof, such as the Fab or F(ab')$_2$ fragments. Single chain antibodies also fall within the scope of the present invention.

Antibody Fragments

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., Proc. Natl. Acad. Sci. (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv).

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv). Techniques for the production of single-chain antibodies (U.S. Pat. No. 4,946,778) can be adapted to produce single-chain antibodies to PVR.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). Monoclonal antibodies may also be isolated from phage antibody libraries using the techniques described, for example, in Clackson et al., Nature 1991, 352, 624-628 or Marks et al., J. Mol. Biol., 1991, 222:581-597.

The design and development of recombinant monovalent antigen-binding molecules derived from monoclonal antibodies through rapid identification and cloning of the functional variable heavy (VH) and variable light (VL) genes and the design and cloning of a synthetic DNA sequence optimized for expression in recombinant bacteria are described in Fields et at. 2013, 8(6):1125-48.

The mAbs of the present invention may be of any immunoglobulin class including IgG, IgM, IgE, IgA, and IgD. A hybridoma producing a mAb may be cultivated in-vitro or in-vivo. High titers of mAbs can be obtained by in-vivo production where cells from the individual hybridomas are injected intra-peritoneally into pristine-primed Balb/c mice to produce ascites fluid containing high concentrations of the desired mAbs. mAbs may be purified from such ascites fluids, or from culture supernatants, using methods well known to those of skill in the art.

Anti-idiotype antibodies specifically immunoreactive with the hypervariable regions of an antibody of the invention are also comprehended.

The invention provides a monoclonal antibody or an antibody fragment comprising an antigen binding domain (ABD) which comprises three CDRs of a light chain and three CDRs of a heavy chain, wherein said ABD has at least 90% sequence identity or similarity with an ABD of a monoclonal mouse antibody comprising: (i) a heavy variable chain comprising the amino acid sequence SEQ ID NO: 69 and a light variable chain comprising the amino acid sequence SEQ ID NO: 71 (herein identified as 4E5 or hPVR.07); (ii) a heavy variable chain comprising the amino acid sequence SEQ ID NO: 73 and a light variable chain comprising the amino acid sequence SEQ ID NO: 75 (herein identified as 7D4 or hPVR.01); or (iii) a heavy variable chain comprising the amino acid sequence SEQ ID NO: 77 and a light variable chain comprising the amino acid sequence SEQ ID NO: 79 (herein identified as 5B9 or hPVR.09). Such antibody may have an ABD domain having at least 93%, at least 94%, at least 95%, at least 96, at least 97, at least 98, at least 99% sequence identity or similarity or 100% sequence identity with corresponding ABD of 4E5, 7D4 or 5B9.

Sequence identity is the amount of amino acids or nucleotides which match exactly between two different sequences. Sequence similarity permits conservative substitution of amino acids to be determined as identical amino acids.

The invention also provides conservative amino acid variants of the antibody molecules according to the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved. The term "antibody analog" as used herein refers to an antibody derived from another antibody by one or more conservative amino acid substitutions.

The term "antibody variant" as used herein refers to any molecule comprising the antibody of the present invention. For example, fusion proteins in which the antibody or an antigen-binding-fragment thereof is linked to another chemical entity is considered an antibody variant.

Analogs and variants of the antibody sequences are also within the scope of the present application. These include, but are not limited to, conservative and non-conservative substitution, insertion and deletion of amino acids within the sequence. Such modification and the resultant antibody analog or variant are within the scope of the present invention as long as they confer, or even improve the binding of the antibody to the human PVR.

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. These substitutions may enhance oral bioavailability, penetration, and targeting to specific cell populations, immunogenicity, and the like. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, according to one table known in the art, the following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

It should be emphasized that the variant chain sequences are determined by sequencing methods using specific primers. Different sequencing methods employed on the same sequence may result in slightly different sequences due to technical issues and different primers, particularly in the sequence terminals. Therefore, different variants of the anti-PVR variable chain sequences are specified along the application.

The terms "molecule having the antigen-binding portion of an antibody" and "antigen-binding-fragments" as used herein are intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see e.g., WO 93/15210, U.S. patent application Ser. No. 08/256,790, WO 96/13583, U.S. patent application Ser. No. 08/817,788, WO 96/37621, U.S. patent application Ser. No. 08/999,554), and single-chain antibodies incorporating such reactive fraction, as well as any other type of molecule in which such antibody reactive fraction has been physically inserted. Such molecules may be provided by any known technique, including, but not limited to, enzymatic cleavage, peptide synthesis or recombinant techniques.

The monoclonal antibodies herein specifically include "chimeric" antibodies in which a portion of the heavy and/or light chain is identical with or homologous to corresponding sequences in antibodies derived from a particular species, or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules of which different portions are derived from different animal species, such as those having a variable region derived from a murine mAb and a human immunoglobulin constant region. Antibodies that have variable region framework residues substantially from human antibody (termed an acceptor antibody) and CDRs substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539).

According to some specific embodiments, the monoclonal antibody is a chimeric monoclonal antibody.

According to some embodiments, the chimeric antibody comprises human-derived constant regions.

According to some embodiments the human constant regions of the chimeric antibody are selected from the group consisting of: human IgG1, human IgG2, human IgG3, and human IgG4.

According to a specific embodiment the chimeric monoclonal antibody or fragment thereof, comprises a constant region subclass of human IgG1 subtype.

According to a particular embodiment, a chimeric monoclonal antibody which recognizes PVR is provided comprising a set of six CDRs selected from the group consisting of: (i) SEQ ID NOs: 4 or 80, 6 or 81, 8 or 82, 12, 14, and, 16; (ii) SEQ ID Nos: 20 or 83, 22, 24, 28, 30, and 32; and (iii) SEQ ID Nos: 36 or 84, 38, 40, 44 or 85, 46, and 48.

Pharmacology

In pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired exposure.

Typically, the antibodies and fragments and conjugates thereof of the present invention comprising the antigen binding portion of an antibody or comprising another polypeptide including a peptide-mimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, topically, intranasally, subcutaneously, intramuscularly, intravenously, intra-arterially, intraarticulary, intralesionally, intratumorally or parenterally. Ordinarily, intravenous (i.v.) administration is used for delivering antibodies.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered, its persistence in the blood circulation, and the judgment of the treating physician.

As used herein the term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The cancer amendable for treatment by the present invention includes, but is not limited to: carcinoma, lymphoma, blastoma, sarcoma, and leukemia or lymphoid malignancies. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high-grade immunoblastic NHL; high-grade lymphoblastic NHL; high-grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amendable for treatment of the invention include metastatic cancers.

According to other embodiments, the pharmaceutical composition according to the invention are for use in treating cancer characterized by PVR overexpression. PVR overexpression related cancer types can be identified using known data bases such as The Cancer Genome Atlas (TCGA). According to certain embodiments, the cancer is selected from the group consisting of adrenocortical carcinoma (ACC), chromophobe renal cell carcinoma (KICH), liver hepatocellular carcinoma (LIHC), colon and rectal adenocarcinoma (COAD, READ), pancreatic ductal adenocarcinoma (PAAD), pheochromocytoma & paraganglioma (PCPG), papillary kidney carcinoma (KIRP), lung adenocarcinoma (LUAD), head and neck squamous cell carcinoma (HNSC), prostate adenocarcinoma (PRAD), uterine corpus endometrial carcinoma (UCEC), cervical cancer (CESC), cutaneous melanoma (SKCM), mesothelioma (MESO), urothelial bladder cancer (BLCA), clear cell kidney carcinoma (KIRC), lung squamous cell carcinoma (LUSC), uterine carcinosarcoma (UCS), sarcoma (SARC), ovarian serous cystadenocarcinoma (OV), papillary thyroid carcinoma (THCA), glioblastoma multiforme (GBM), breast cancer (BRCA), lower grade glioma (LGG), and diffuse large B-cell lymphoma (DLBC). Each possibility represents a separate embodiment of the invention.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The pharmaceutical composition according to the present invention may be administered together with an anti-neoplastic composition.

The term "treatment" as used herein refers to both therapeutic treatment and prophylactic or preventative measures. Those in need of treatment include those already with the disorder as well as those in which the disorder is to be prevented.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include melanoma, lung, thyroid, breast, colon, prostate, hepatic, bladder, renal, cervical, pancreatic, leukemia, lymphoma, myeloid, ovarian, uterus, sarcoma, biliary, or endometrial cancer.

According to some embodiments, the method of treating cancer comprises administering the pharmaceutical composition as part of a treatment regimen comprising administration of at least one additional anti-cancer agent.

According to some embodiments, the anti-cancer agent is selected from the group consisting of an antimetabolite, a mitotic inhibitor, a taxane, a topoisomerase inhibitor, a topoisomerase II inhibitor, an asparaginase, an alkylating agent, an antitumor antibiotic, and combinations thereof. Each possibility represents a separate embodiment of the invention.

According to some embodiments, the antimetabolite is selected from the group consisting of cytarabine, gludarabine, fluorouracil, mercaptopurine, methotrexate, thioguanine, gemcitabine, and hydroxyurea. According to some embodiments, the mitotic inhibitor is selected from the group consisting of vincristine, vinblastine, and vinorelbine.

According to some embodiments, the topoisomerase inhibitor is selected from the group consisting of topotecan and irenotecan. According to some embodiments, the alkylating agent is selected from the group consisting of busulfan, carmustine, lomustine, chlorambucil, cyclophosphamide, cisplatin, carboplatin, ifosamide, mechlorethamine, melphalan, thiotepa, dacarbazine, and procarbazine. According to some embodiments, the antitumor antibiotic is selected from the group consisting of bleomycin, dactinomycin, daunorubicin, doxorubicin, idarubicin, mitomycin, mitoxantrone, and plicamycin. According to some embodiments, the topoisomerase II is selected from the group consisting of etoposide and teniposide. Each possibility represents a separate embodiment of the present invention.

According to some particular embodiments, the additional anti-cancer agent is selected from the group consisting of bevacizumab, carboplatin, cyclophosphamide, doxorubicin hydrochloride, gemcitabine hydrochloride, topotecan hydrochloride, thiotepa, and combinations thereof. Each possibility represents a separate embodiment of the present invention.

Monoclonal antibodies according to the present invention may be used as part of combined therapy with at least one anti-cancer agent. According to some embodiments, the additional anti-cancer agent is an immuno-modulator, an activated lymphocyte cell, a kinase inhibitor or a chemotherapeutic agent.

According to some embodiments, the anti-cancer agent is an immuno-modulator, whether agonist or antagonist, such as antibody against an immune checkpoint molecule.

Checkpoint immunotherapy blockade has proven to be an exciting new venue of cancer treatment. Immune checkpoint pathways consist of a range of co-stimulatory and inhibitory molecules which work in concert in order to maintain self-tolerance and protect tissues from damage by the immune system under physiological conditions. Tumors take advantage of certain checkpoint pathways in order to evade the immune system. Therefore, the inhibition of such pathways has emerged as a promising anti-cancer treatment strategy.

The anti-cytotoxic T lymphocyte 4 (CTLA-4) antibody ipilimumab (approved in 2011) was the first immunotherapeutic agent that showed a benefit for the treatment of cancer patients. The antibody interferes with inhibitory signals during antigen presentation to T cells. Anti-programmed cell death 1 (PD-1) antibody pembrolizumab (approved in 2014) blocks negative immune regulatory signaling of the PD-1 receptor expressed by T cells. An additional anti-PD-1 agent was filed for regulatory approval in 2014 for the treatment of non-small cell lung cancer (NSCLC). Active research is currently exploring many other immune checkpoints, among them: CEACAM1, NKG2A, B7-H3, B7-H4, VISTA, CD112R, lymphocyte activation gene 3 (LAG3), CD137, OX40 (also referred to as CD134), and killer cell immunoglobulin-like receptors (KIR).

According to some specific embodiments, the immuno-modulator is selected from the group consisting of: an antibody inhibiting CTLA-4, an anti-human programmed cell death protein 1 (PD-1), PD-L1 and PD-L2 antibody, an activated cytotoxic lymphocyte cell, a lymphocyte activating agent, an antibody against CEACAM, an antibody against TIGIT, and a RAF/MEK pathway inhibitor. Each possibility represents a separate embodiment of the present invention. According to some specific embodiments, the additional immuno-modulator is selected from mAb to PD-1, mAb to PD-L1, mAb to PD-L2, mAb to CEACAM1, mAb to CTLA-4, mAB to TIGIT, Interleukin 2 (IL-2) or lymphokine-activated killer (LAK) cell.

According to other embodiments the additional anti-cancer agent is a chemotherapeutic agent. The chemotherapy agent, which could be administered together with the antibody according to the present invention, or separately, may comprise any such agent known in the art exhibiting anticancer activity, including but not limited to: mitoxantrone, topoisomerase inhibitors, spindle poison vincas: vinblastine, vincristine, vinorelbine (taxol), paclitaxel, docetaxel; alkylating agents: mechlorethamine, chlorambucil, cyclophosphamide, melphalan, ifosfamide; methotrexate; 6-mercaptopurine; 5-fluorouracil, cytarabine, gemcitabin; podophyllotoxins: etoposide, irinotecan, topotecan, dacarbazin; antibiotics: doxorubicin (adriamycin), bleomycin, mitomycin; nitrosoureas: carmustine (BCNU), lomustine, epirubicin, idarubicin, daunorubicin; inorganic ions: cisplatin, carboplatin; interferon, asparaginase; hormones: tamoxifen, leuprolide, flutamide, and megestrol acetate.

According to some embodiments, the chemotherapeutic agent is selected from alkylating agents, antimetabolites, folic acid analogs, pyrimidine analogs, purine analogs and related inhibitors, vinca alkaloids, epipodophyllotoxins, antibiotics, L-asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. According to another embodiment, the chemotherapeutic agent is selected from the group consisting of 5-fluorouracil (5-FU), leucovorin (LV), irenotecan, oxaliplatin, capecitabine, paclitaxel and doxetaxel. One or more chemotherapeutic agents can be used.

In some embodiments, the pharmaceutical composition according to the present invention is for use in treating cancer or for use in enhancing the immune response.

The term "enhancing immune response" refers to increasing the responsiveness of the immune system and inducing or prolonging its memory. The pharmaceutical composition according to the present invention may be used to stimulate immune system upon vaccination. Thus, in one embodiment the pharmaceutical composition can be used for improving vaccination.

In certain embodiments, the cancer is selected from lung, thyroid, breast, colon, melanoma, prostate, hepatic, bladder, renal, cervical, pancreatic, leukemia, lymphoma, myeloid, ovarian, uterus, sarcoma, biliary, and endometrial cells cancer. Each possibility represents a separate embodiment of the invention.

According to some embodiments, a pharmaceutical composition, comprising at least one antibody or fragment thereof according to the present invention, and a pharmaceutical composition, comprising an additional immunomodulator or a kinase inhibitor, are used in treatment of cancer by separate administration.

According to still another aspect the present invention provides a method of treating cancer in a subject in need thereof comprising administering to said subject a therapeutically effective amount of a monoclonal antibody or antibody fragment according to the present invention.

The term "effective amount" as used herein refers to a sufficient amount of the monoclonal antibody of the antibody fragment that, when administered to a subject will have the intended therapeutic effect. The effective amount required to achieve the therapeutic end result may depend on a number of factors including, for example, the specific type of the tumor and the severity of the patient's condition, and whether the combination is further co-administered with radiation. The effective amount (dose) of the active agents, in the context of the present invention should be sufficient to affect a beneficial therapeutic response in the subject over time, including but not limited to inhibition of tumor growth, reduction in the rate of tumor growth, prevention of tumor and metastasis growth and enhanced survival.

Toxicity and therapeutic efficacy of the compositions described herein can be determined by standard pharmaceutical procedures in cell cultures or experimental animals, e.g., by determining the IC50 (the concentration which provides 50% inhibition) and the maximal tolerated dose for a subject compound. The data obtained from these cell culture assays and animal studies can be used in formulating a range of dosages for use in humans. The dosage may vary depending inter alia upon the dosage form employed, the dosing regimen chosen, the composition of the agents used for the treatment and the route of administration utilized, among other relevant factors. The exact formulation, route of administration and dosage can be chosen by the individual physician in view of the patient's condition. Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

The term "administering" or "administration of" a substance, a compound or an agent to a subject can be carried out using one of a variety of methods known to those skilled in the art. For example, a compound or an agent can be administered enterally or parenterally. Enterally refers to administration via the gastrointestinal tract including per os, sublingually or rectally. Parenteral administration includes administration intravenously, intradermally, intramuscularly, intraperitoneally, subcutaneously, ocularly. sublingually, intranasally, by inhalation, intraspinally, intracerebrally, and transdermally (by absorption, e.g., through a skin duct). A compound or agent can also appropriately be introduced by rechargeable or biodegradable polymeric devices or other devices, e.g., patches and pumps, or formulations. which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Antibodies are generally administered in the range of about 0.1 to about 20 mg/kg of patient weight, commonly about 0.5 to about 10 mg/kg, and often about 1 to about 5 mg/kg. In this regard, it is preferred to use antibodies having a circulating half-life of at least 12 hours, preferably at least 4 days, more preferably up to 21 days. Chimeric antibodies are expected to have circulatory half-lives of up to 14-21 days. In some cases it may be advantageous to administer a large loading dose followed by periodic (e.g., weekly) maintenance doses over the treatment period. Antibodies can also be delivered by slow-release delivery systems, pumps, and other known delivery systems for continuous infusion.

The term "about" means that an acceptable error range, e.g., up to 5% or 10%, for the particular value should be assumed.

Angiogenesis

According to an aspect, the present invention provides a pharmaceutical composition according to the present invention for use in treating an angiogenesis-related disease or disorder.

Angiogenesis is an important cellular event in which vascular endothelial cells proliferate, prune and reorganize to form new vessels from preexisting vascular networks. There is compelling evidence that the development of a vascular supply is essential for normal and pathological proliferative processes and inflammation. The vascular compartment is necessary not only for organ development and differentiation during emnbryogenesis, but also for wound healing, tissue repair and reproductive functions in the adult.

Angiogenesis is also implicated in the pathogenesis of a variety of disorders, including but not limited to, tumors, proliferative retinopathies, age-related macular degeneration, rheumatoid arthritis, and psoriasis. Angiogenesis is essential for the growth of most primary tumors and their subsequent metastasis. Tumors can absorb sufficient nutrients and oxygen by simple diffusion up to a size of 1-2 mm, at which point their further growth requires the elaboration of a vascular supply. This process is thought to involve recruitment of the neighboring host mature vasculature to begin sprouting new blood vessel capillaries, which grow toward, and subsequently infiltrate, the tumor mass. In addition, tumor angiogenesis involves the recruitment of circulating endothelial precursor cells from the bone marrow to promote neovascularization.

Diagnosis

The present invention further discloses methods for diagnosing and prognosing cancer.

According to an aspect, the present invention provides a diagnostic and/or prognostic method of cancer or infectious disease in a subject, the method comprises the step of determining the expression level of PVR in a biological sample of said subject using at least one antibody as described herein.

The term "biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived there from and the progeny thereof. Additionally, the term may encompass circulating tumor or other cells. The term specifically encompasses a clinical sample, and further includes cells in cell culture, cell supernatants, cell lysates, serum, plasma, urine, amniotic fluid, biological fluids including aqueous humour and vitreous for eyes samples, and tissue samples. The term also encompasses samples that have been manipulated in any way after procurement, such as treatment with reagents, solubilisation, or enrichment for certain components.

Determining the expression level of PVR can be performed by a labeled anti-PVR antibody as described herein. Determining the expression can be performed, for example, by ELISA.

The method of the invention can further comprise the step of comparing said level of expression to a control level.

The following examples are presented in order to more fully illustrate some embodiments of the invention. They should, in no way be construed as limiting the scope of the invention.

EXAMPLES

Experimental Procedures

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are well known in the art. Other general references referring to well-known procedures are provided throughout this document for the convenience of the reader.

Example 1. High PVR Expression Correlates with Poor Prognosis

Figure 1B:
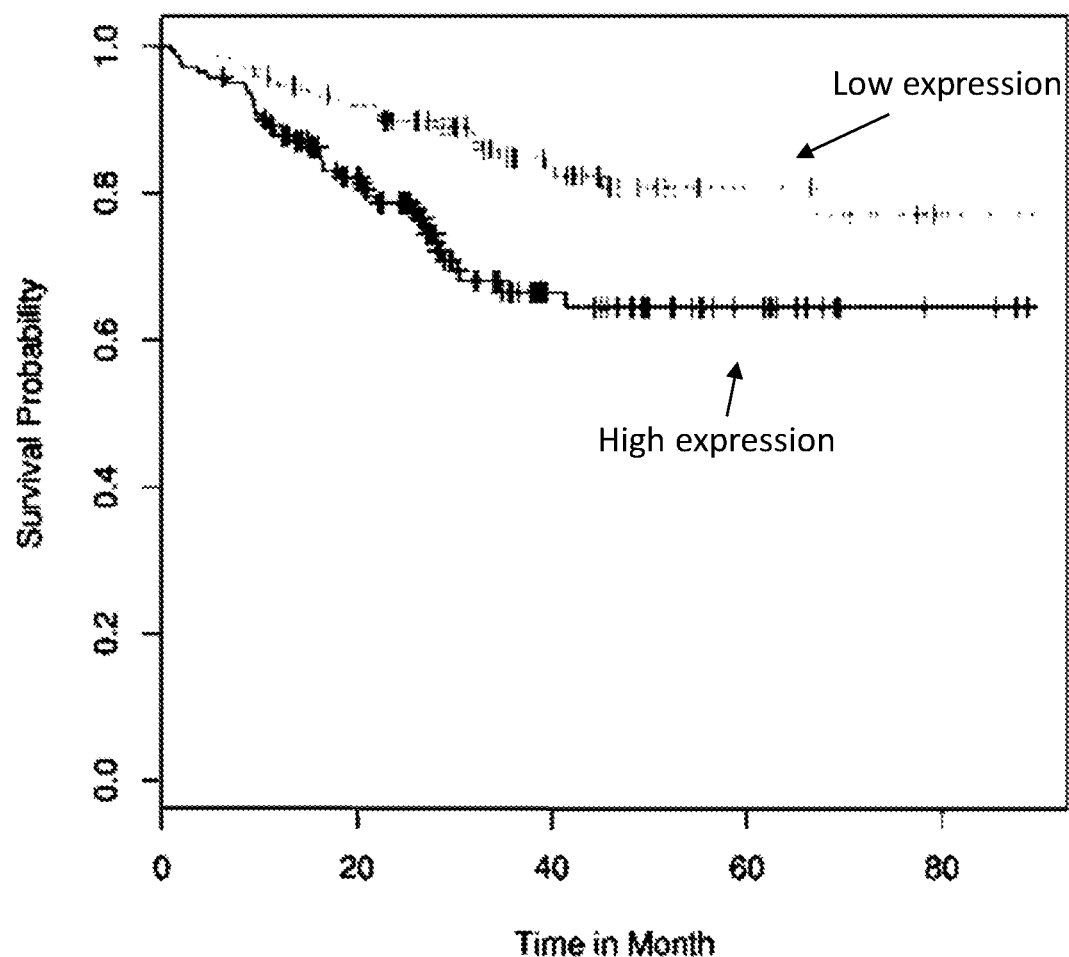
Figure 1C:
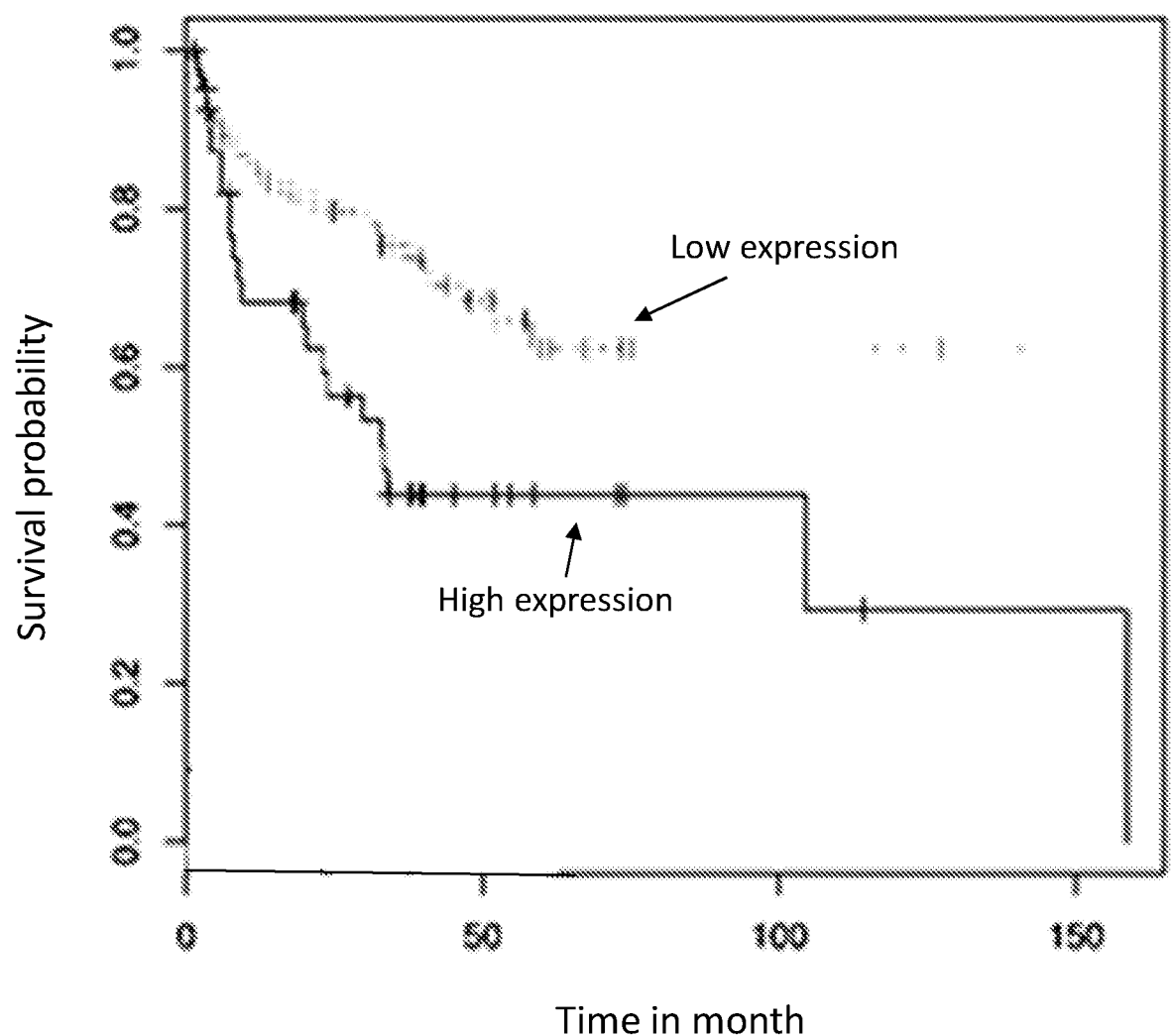
Figure 2:
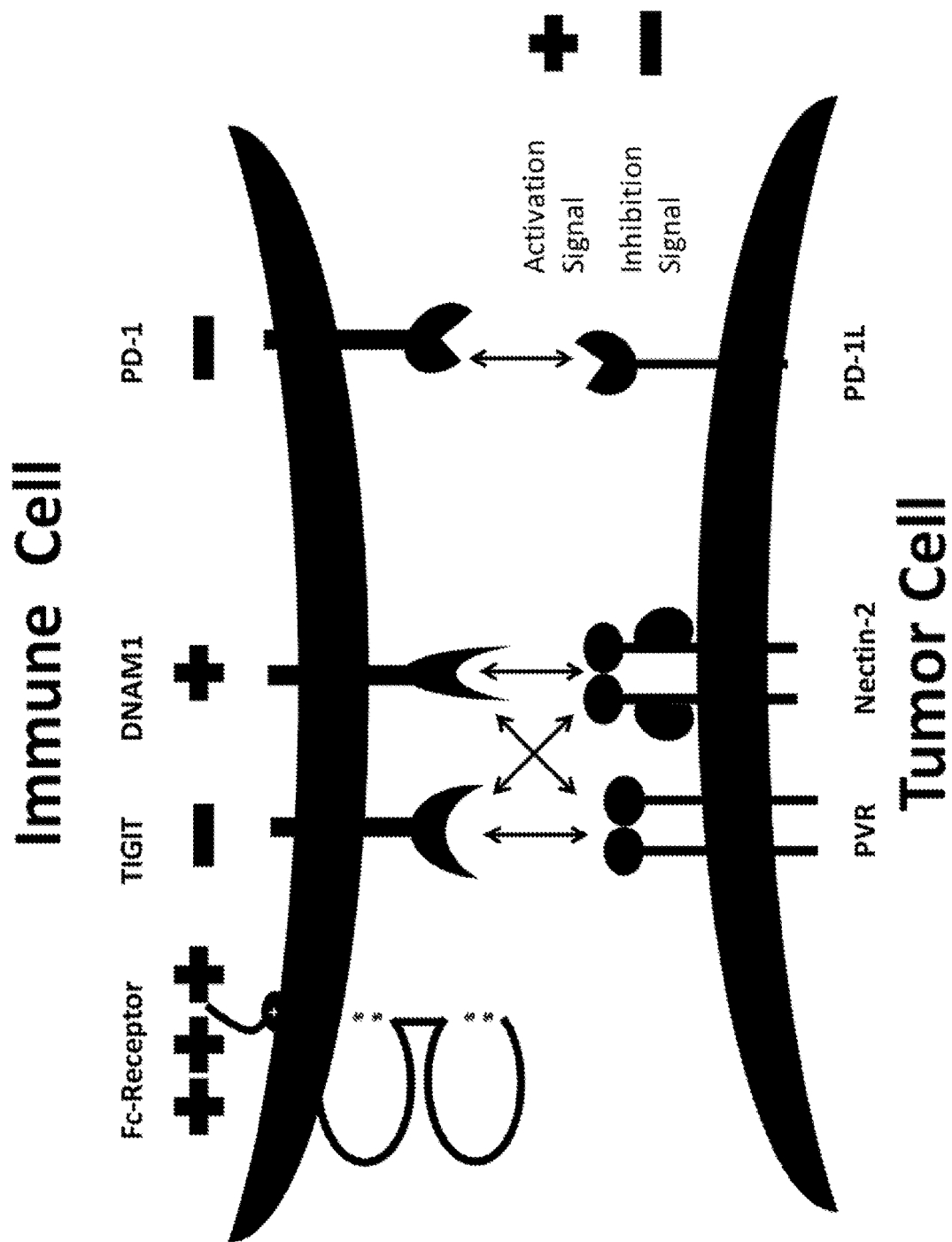
FIG. 2 is a schematic illustration of receptor expression on immune and tumor cells. TIGIT relates to a co-inhibitory receptor on many immune cells (e.g. T cells); DNAM-1 (also termed CD226) relates to an activating receptor on many immune cells (e.g. T cells); Fc Receptor relates to the strong activating receptor expressed mainly on NK cells but also on myeloid cells including neutrophils and macrophages; PVR relates to an inhibitory ligand for TIGIT (weaker binding to DNAM-1), expressed by many tumor cells; Nectin-2 relates to an activating ligand for DNAM-1 (marginal recognition by TIGIT), expressed by many tumor cells. Binding of anti-PVR according to the present invention shows a dual effect: 1) enhancing the killing of tumor cells via Fc receptors; and 2) increasing activation of immune cells by blocking the interaction with TIGIT.

PVR and Nectin-2 are ligands for the inhibitory receptor TIGIT (FIG. 2). The results illustrate that high PVR expression levels correlated with poor cancer prognosis of lung cancer, breast cancer and liposarcoma (FIGS. 1A-C, respectively). GEO expression of PVR was correlated to survival using bioprofiling.de the relevant data sets are ID: GSE31210, GSE25055, GSE30929. Furthermore, using the same analysis, Nectin-2 expression was mostly a positive marker for survival.

Example 2. Generation and Purification of Anti-PVR mAbs

In order to generate anti-PVR antibodies, a recombinant protein was produced and purified, hPVR-Fc, that combines extracellular part of human PVR and human Fc region of an immunoglobulin G carrier as an immunogen.

BALB/c mice were injected with 50 µg of the immunogen in complete Freund's adjuvant and 2 weeks later in incomplete Freund's adjuvant. After 2 weeks, the sera were screened for the antibody titer. The best responders (the serum was monitored by ELISA assay for the titer of the anti-hPVR-Fc antibodies) were boosted with the immunogen in PBS. Three days later, spleen cells were collected, and after lysis of red blood cells, fused with SP2/0 cells. The cells were seeded in 20% RPMI 1640 medium containing hypoxanthine, aminopterine, and thymidine for hybridoma selection and screened for mAbs using ELISA. Stable hybridoma cell lines were generated by fusing SP2/0 myeloma cells with spleen cells of an immunized mouse.

Positive outcomes (cell lines secreting antibodies that recognize hPVR-Fc) were further selected to develop a product that will have several differentiating characteristics: a) high yield to reduce the antibody-production costs; b) the lack of cross-reactivity between mouse and human PVR and several other ligands of the immune cell receptors; c) a strong binding capacity to the native, mature human PVR molecules expressed on the surface of live cells (the antibodies were chosen from a comprehensive anti-hPVR monoclonal antibody pool with proven capability to recognize hPVR in different techniques e.g. flow cytometry, western blot, ELISA). Indeed, the human and mouse PVR have high level of homology and it is not easy to generate a mouse monoclonal antibody that recognizes a human homologue. More importantly, human PVR is extensively glycosylated on its extracellular region. For these reasons, it is not easy to generate an antibody that recognizes a native protein using common antigens (such as *E. coli* derived ones).

The present inventors have used the hPVR-Fc immunogen, a molecule produced in mammalian human embryonic kidney 293 (HEK 293T) cells and purified under native conditions by immunoaffinity chromatography, to closely mimic the native protein, human PVR. In conclusion, from a pool of generated anti-hPVR mAbs, representatives that recognize a native human PVR form on live cells were identified, which is a prerequisite to develop a derivative that would influence the human immune cell response during the treatment.

Figure 3B:
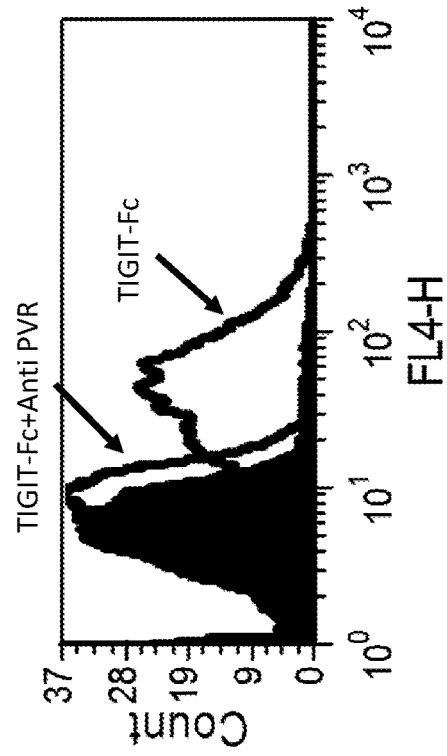
FIGS. 3A-3D. are graphs depicting FACS analysis of the four anti-PVR antibodies generated. Shown is the efficacy of the antibodies in blocking the direct binding of TIGIT-Fc to a tumor cell line.
Figure 3D:
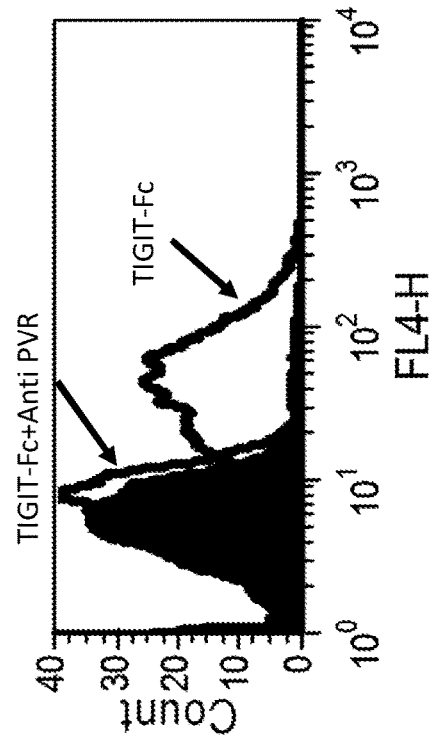
Figure 3A:
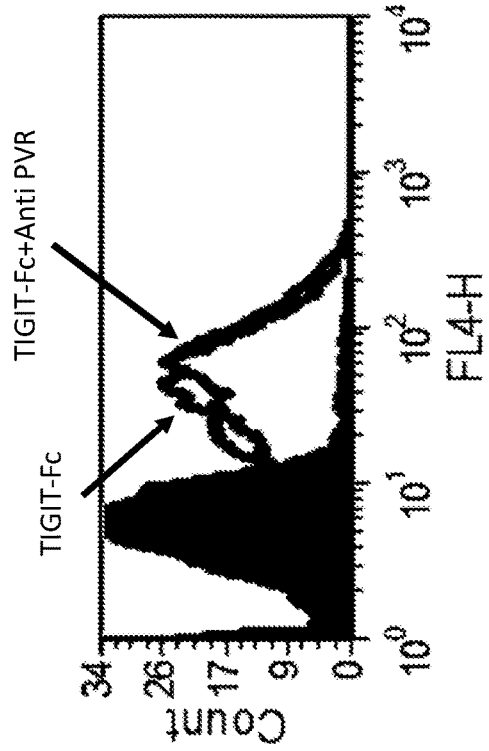
Figure 3C:
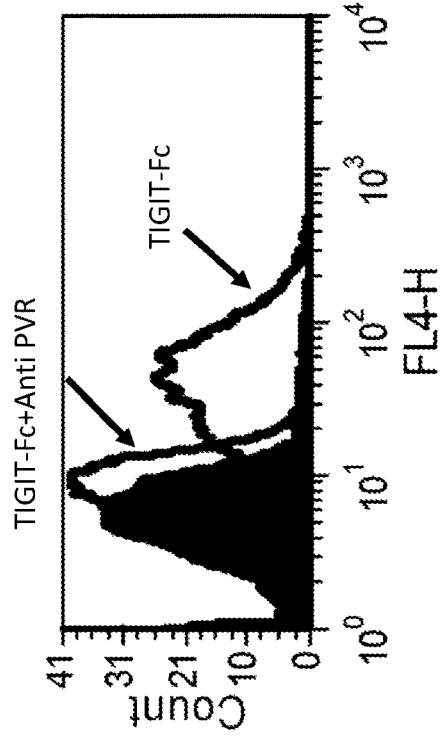

Four anti-PVR antibodies were generated. Of these, three antibodies were blocking anti-PVR mAbs, namely antibody 5B9 (also termed hPVR.09), antibody 7D4 (also termed hPVR.01) and antibody 4E5 (also termed hPVR.07). These antibodies all block TIGIT-Ig binding (as illustrated in FIGS. 3B-D, respectively). A fourth antibody was generated which does not block TIGIT-Ig binding and was termed 2G3 (also termed hPVR.17) (FIG. 3A).

Surface plasmon resonance (SPR) Biosensor Biacore™ T100 (GE Healthcare) was used to determine Koff, Kon and $K_D$ between the antibodies and hPVR (Table 1).

TABLE 1

| Antibodies affinity measurement by Biacore ™ | |
|---|---|
| mAB | Affinity |
| 4E5 | $7.22E^{-10}$ |
| 5B9 | $1.62E^{-09}$ |
| 7D4 | $1.93E^{-10}$ |

Chimeric monoclonal antibodies, comprising human heavy chain constant IgG1 region set forth in SEQ ID NO:

86 (corresponding to GenBank: AAA02914.1), were produced from the above three antibodies, using methods known in the art.

Figure 4:
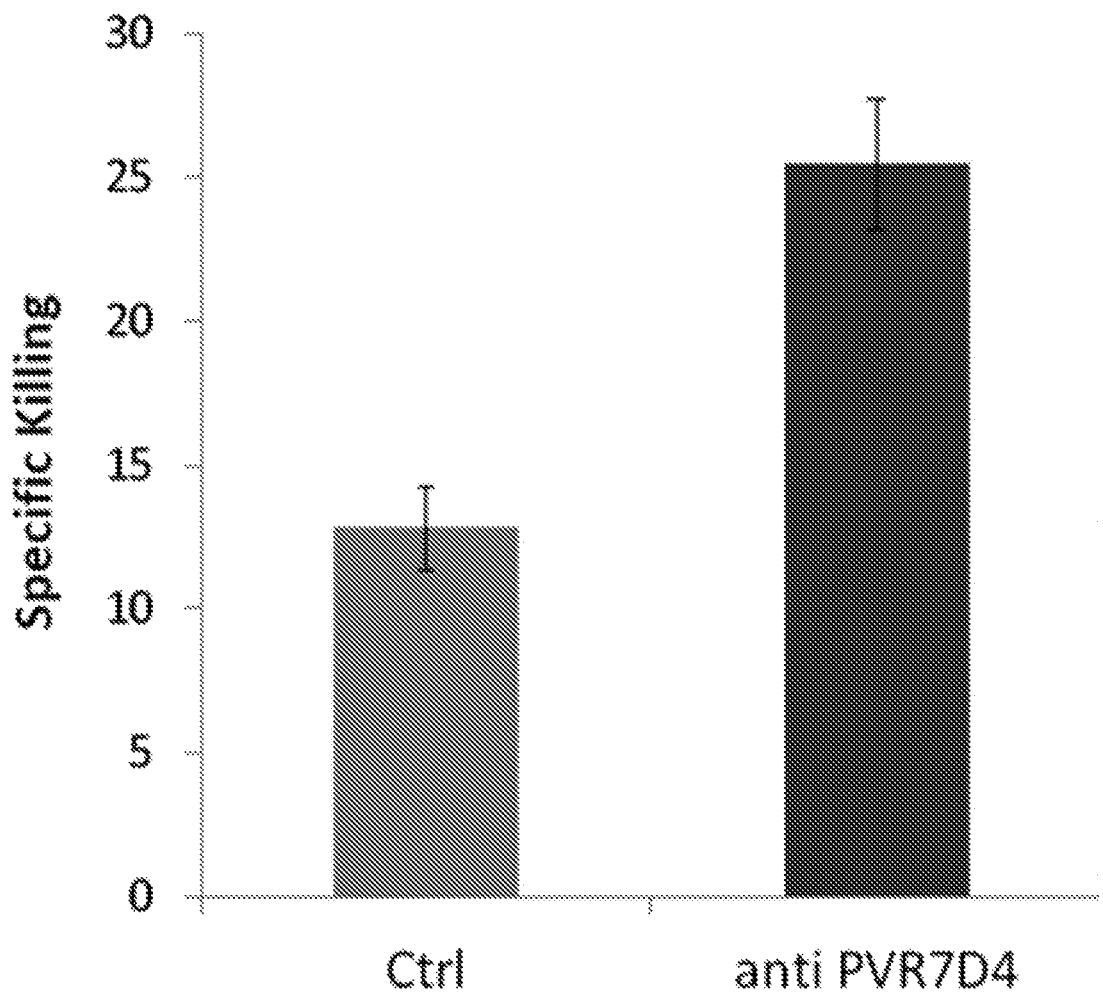
FIG. 4 is a graph that shows how blocking of PVR-TIGIT interactions with the anti-PVR mAb antibody 7D4 (also termed hPVR.01) enhances NK cell killing of the human cell line MDA-MB-231 (Breast Adenocarcinoma). Specific killing is calculated based on the secretion of [35S]—Methionine from the target cells. Control (Ctrl) is non-related mouse IgG. P Value=0.0056.

Example 3. Blocking of PVR-TIGIT Interactions with Anti-PVR mAb Enhanced NK Cell Killing of Human Cell Lines The target cells were labeled with [35S]-Methionine 12 hours prior to the assay. Indicated antibodies were added to the final concentration of 5 µg/ml and incubated with the labeled targets (5000 cells/well) for 30 minutes on ice. The assays were performed in RPMI medium in 96U shaped plates at 37° C. for 5 hours. Labeled targets were incubated with effector NK cells at 10:1 E:T ratio. Following incubation, plates were centrifuged (1600 rpm, 5 min, 4° C.) and supernatants (50 µl) were collected and transferred to opaque Opti-plates (Packard). 150 µl scintillation liquid (Perkin Elmer) was added and analyzed by a micro beta, β-counter (Perkin Elmer). The maximal labeling was determined by adding 100 µl of 0.1N NaOH to an equal amount of targets (5000/well). Spontaneous release was determined in wells containing target cells only. Final specific killing was calculated as follows: ((radioactive reading−spontaneous release)/(maximal labeling−spontaneous release))*100=specific killing. As shown in FIG. 4, culturing of NK cells with the anti-PVR mAb 7D4 (also termed hPVR.01) enhanced (by two folds) NK cell killing of the human breast Adenocarcinoma cell line MDA-MB-231.

Example 4. Blocking of PVR-TIGIT Interactions with Anti-PVR mAb Enhanced NK Cell Killing of Human Cancer Cell Lines Target cells were labeled with [35S]-Methionine 12 hours prior to the assay. Indicated antibodies were added to the final concentration of 5 µg/ml and incubated with the labeled targets (5000 cells/well for 30 minutes on ice. The cells were incubated with effector NK cells at 10:1 E:T ratio. The assays were performed in RPMI medium in 96-U shaped plates at 37° C. for 5 hours. Following incubation, plates were centrifuged (1600 rpm, 5 min, 4° C.) and supernatants (50 µl) were collected and transferred to opaque Opti-plates (Packard). 150 µl scintillation liquid (Perkin Elmer) was added and analyzed by a micro beta, β-counter (Perkin Elmer). The maximal labeling was determined by adding 100 µl of 0.1N NaOH to an equal amount of targets (5000/well). Spontaneous release was determined in wells containing target cells only. Final specific killing was calculated as follows: ((radioactive reading−spontaneous release)/(maximal labeling−spontaneous release))*100=specific killing.

Figure 5:
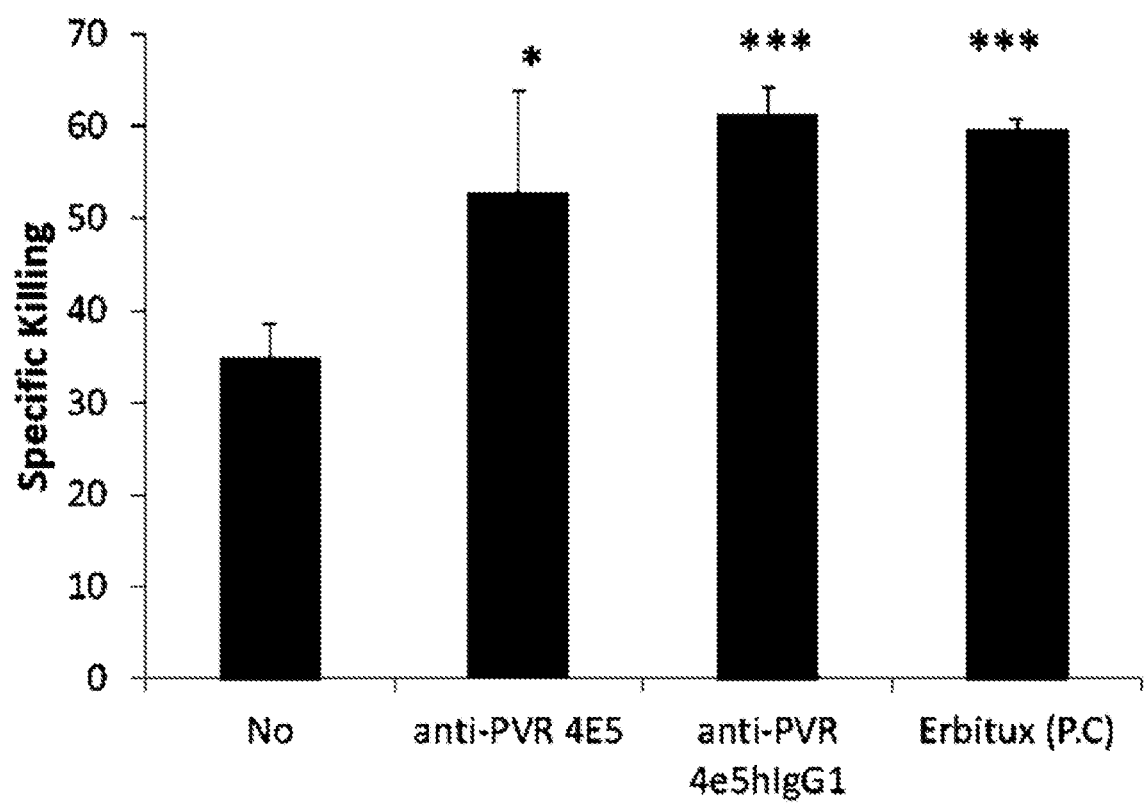
FIG. 5 is a graph depicting that blocking of PVR-TIGIT interactions using the anti-PVR mAb 4E5 (also termed hPVR.07) enhances NK cell killing of human cancer cell line HepG2 (hepatocellular carcinoma). No—killing of HepG2 without mAb; anti-PVR 4E5—killing of HepG2 with mouse anti-PVR 4E5mIgG1 (no activation of human Fc receptor); anti-PVR 4e5hIgG1—killing of HepG2 with anti-PVR 4E5-hIgG1 (activation of human Fc receptor), Erbitux (P.C)—a positive control mAb Erbitux (anti-EGFR). All mAbs were used at 10 µg/ml. P values: anti-PVR 4E5—0.04, anti-PVR 4e5hIgG1—0.000746 and Erbitux (positive control)—0.003219.

As shown in FIG. 5, blocking of PVR-TIGIT interactions with the anti-PVR mAb 4E5 (also termed hPVR.07) enhances NK cell killing of human cancer cell line HepG2 (hepatocellular carcinoma). It is thus clear that blocking of PVR leads to enhanced killing of the target cells. The killing is further enhanced when the human IgG counterpart of 4E5 was used in a chimeric version of the mAb. The killing is equivalent to the positive control (Erbitux©).

Example 5. Human Tumor Cell Lines Express PVR and Nectin-2

Figure 6A:
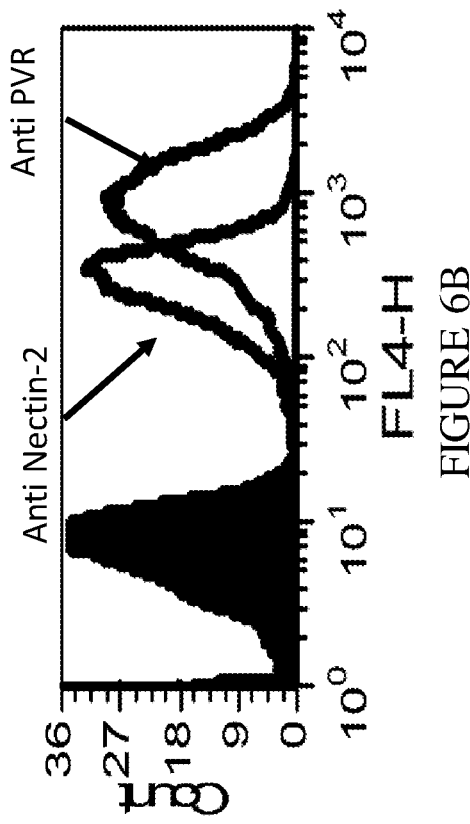
FIGS. 6A-6O are graphs depicting that human tumor cell lines express PVR and Nectin-2. Melanoma cells (FIGS. 6A-E), breast cancer cells (FIGS. 6F-H), colorectal cells (FIG. 6I), kidney cells (FIG. 6J), lung cancer cells (FIG. 6K), prostate cancer cells (FIG. 6L), brain tumor cells (FIG. 6M), and hepatocellular carcinoma cells (FIGS. 6N-O) all express PVR and Nectin-2. mAbs were used at 0.2 µg/well: a commercial anti-Nectin-2 mAb and the anti-PVR mAb 4E5 (also termed hPVR.07).
Figure 6B:
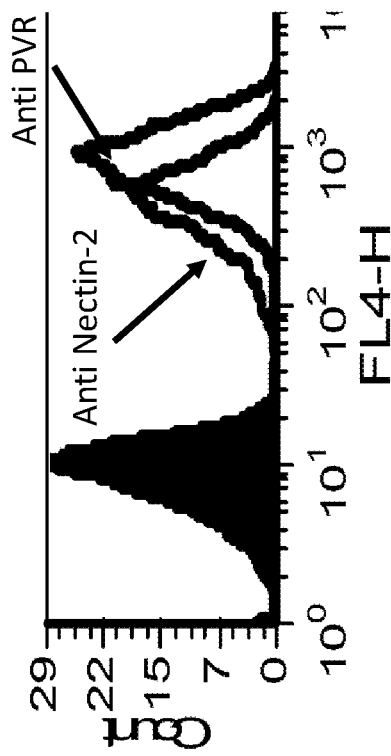
Figure 6C:
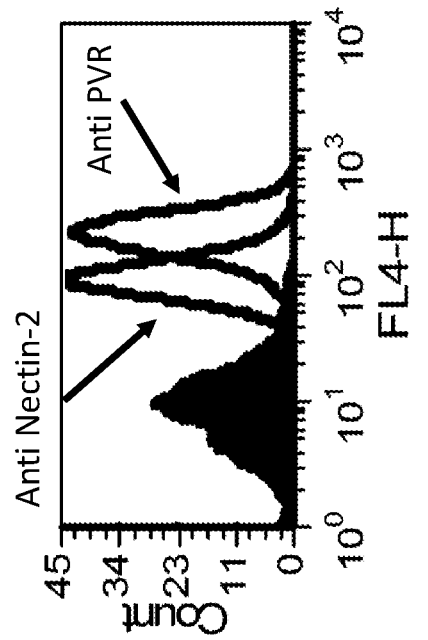
Figure 6D:
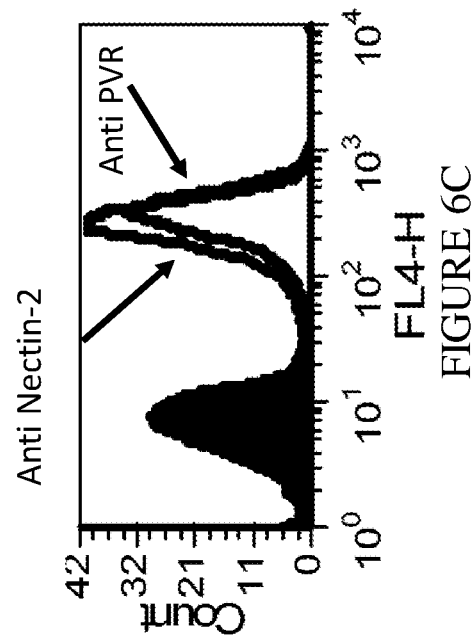
Figure 6E:
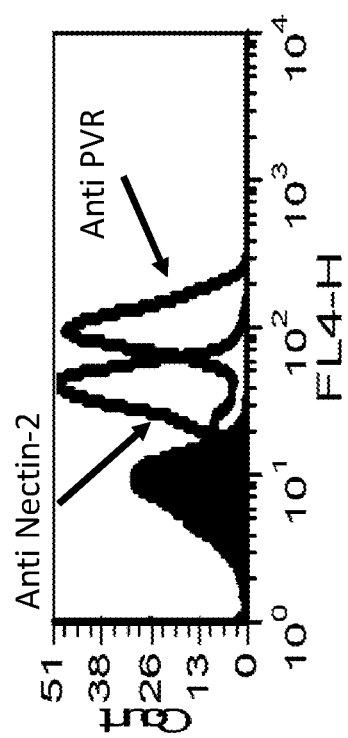
Figure 6G:
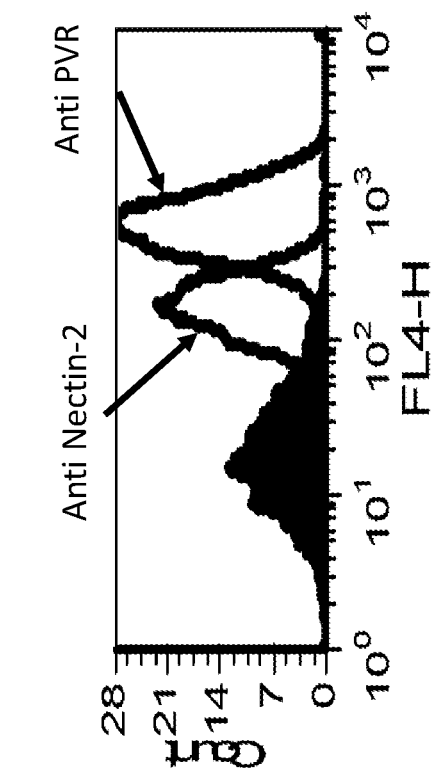
Figure 6F:
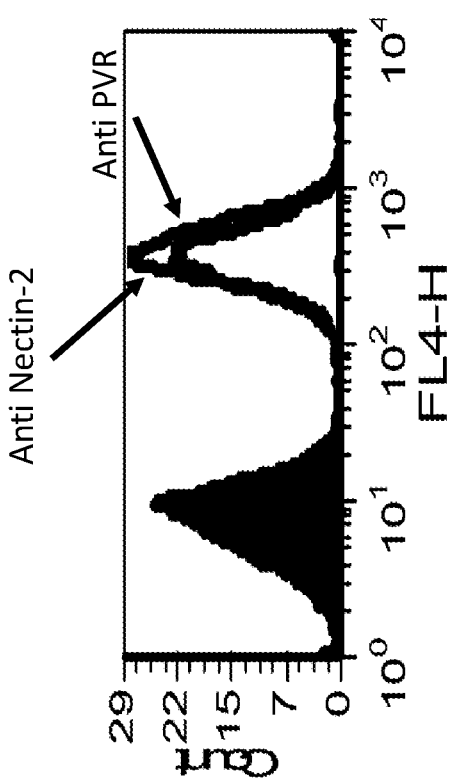
Figure 6H:
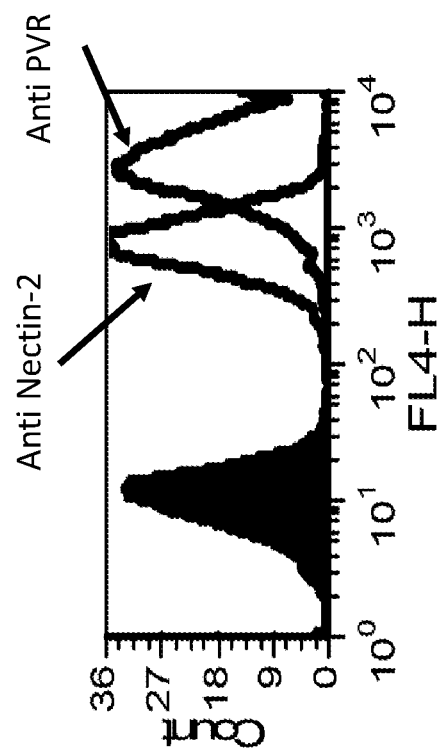
Figure 6J:
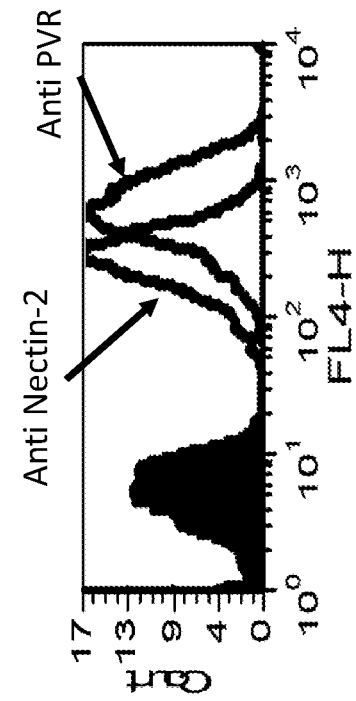
Figure 6L:
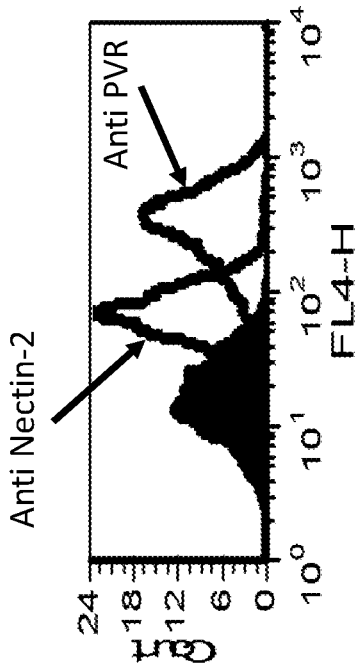
Figure 6I:
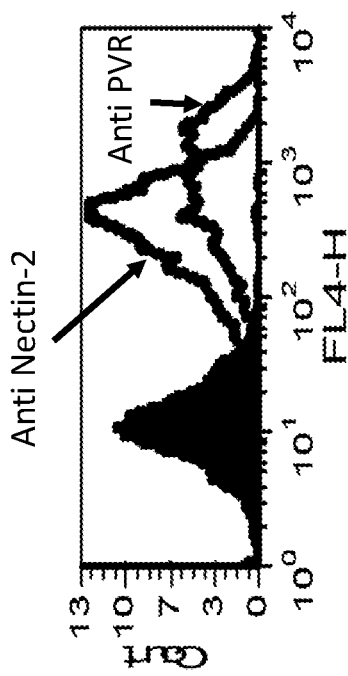
Figure 6K:
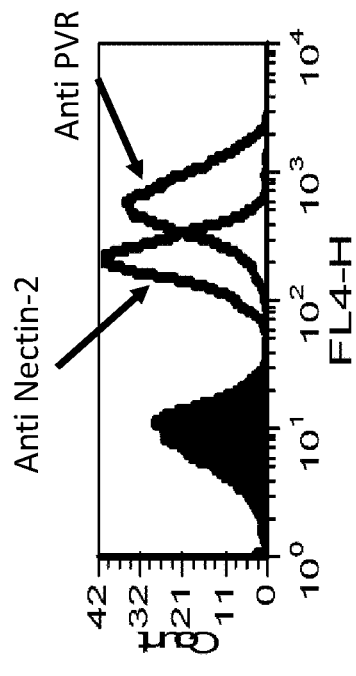
Figure 6M:
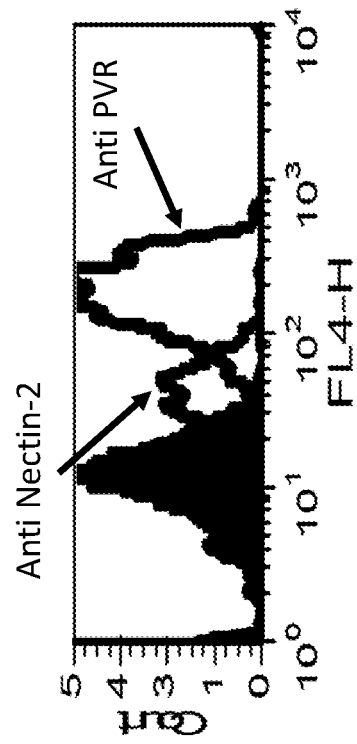
Figure 6N:
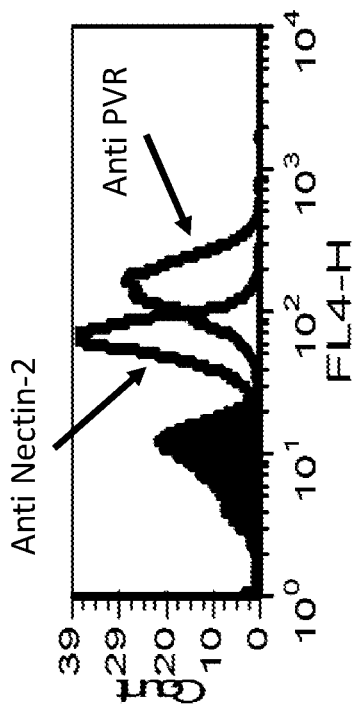
Figure 6O:
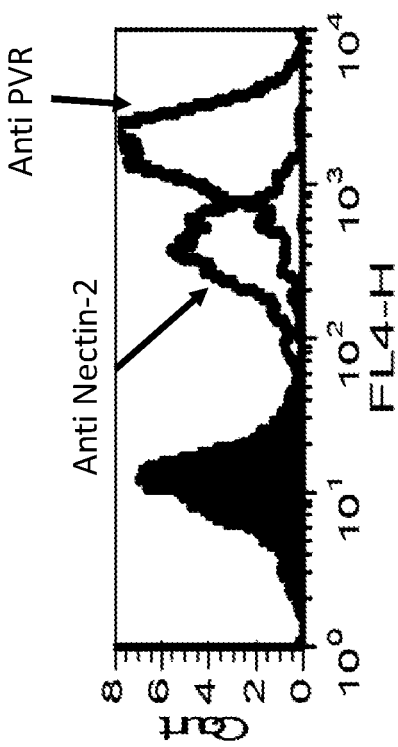

To examine the expression of PVR and Nectin-2 on tumor cells, expression levels of these proteins on different tumor cell lines was examined by FACS analysis using the anti PVR-4E5 Ab and the anti-Nectin-2 Ab (clone TX-31), both at 2 µg/ml. As shown in FIGS. 6A-O, various human tumor cell lines express PVR and Nectin-2. Specifically, it is shown that melanoma cells (FIGS. 6A-E), breast cancer cells (FIGS. 6F-H), colorectal cells (FIG. 6I), kidney cells (FIG. 6J), lung cancer cells (FIG. 6K), prostate cancer cells (FIG. 6L), brain tumor cells (FIG. 6M), and hepatocellular carcinoma cells (FIGS. 6N-O) all express PVR and Nectin-2.

Example 6. PVR is the Main TIGIT Ligand

FIGS. 7A-7C demonstrate that PVR is the main TIGIT ligand. Specifically, it was shown that HepG2 cells (human hepatocellular carcinoma cells) express both PVR and Nectin-2 (FIG. 7A). Culturing of HepG2 cells with purified anti-PVR mAb 4E5, also termed hPVR.07 (0.15 µg/well), almost completely blocked TIGIT-Ig binding (2 µg/ml) (FIG. 7B), despite the fact that these cells also express Nectin-2. As shown in FIGS. 7C and 7D, it is clear that there was no direct recognition of Nectin-2 by anti-PVR mAbs.

Example 7. Binding of mAb Clones to Human and Primate PVR

Figure 8A:
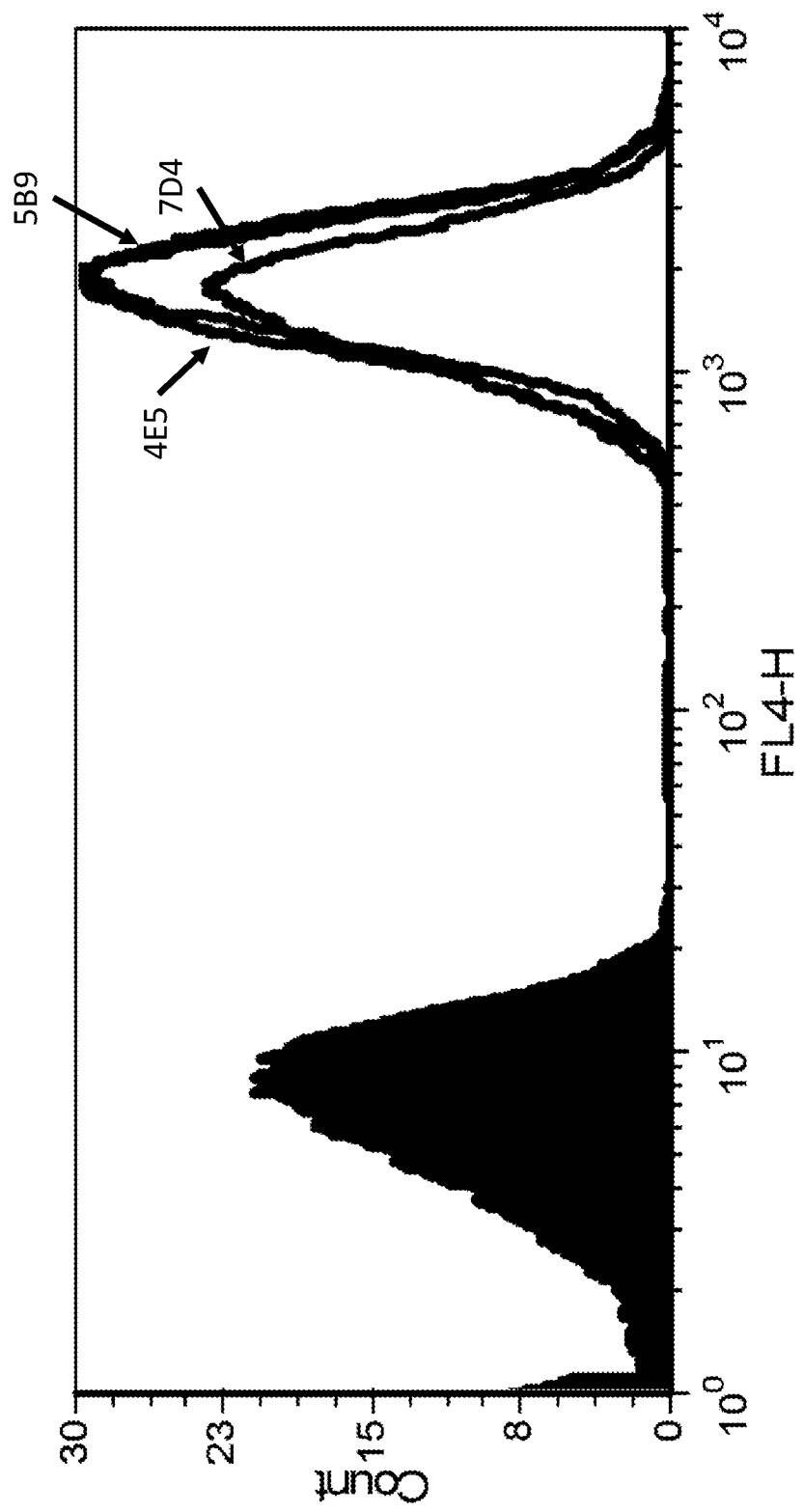
FIGS. 8A-8C depict a similar binding efficacy of all of the anti-PVR mAbs to human PVR. All three blocking clones generate similar (less than 10% difference) binding to both endogenous PVR HepG2 cells (FIG. 8A) and overexpressed hPVR B16-hPVR cells (FIG. 8B). Binding was also examined using Vero cell line from African green monkey (FIG. 8C) which express a PVR protein with 93% similarity to human PVR. In this case the different Abs showed differential staining intensities. 0.2 µg of each mAb used in all cases.
Figure 8B:
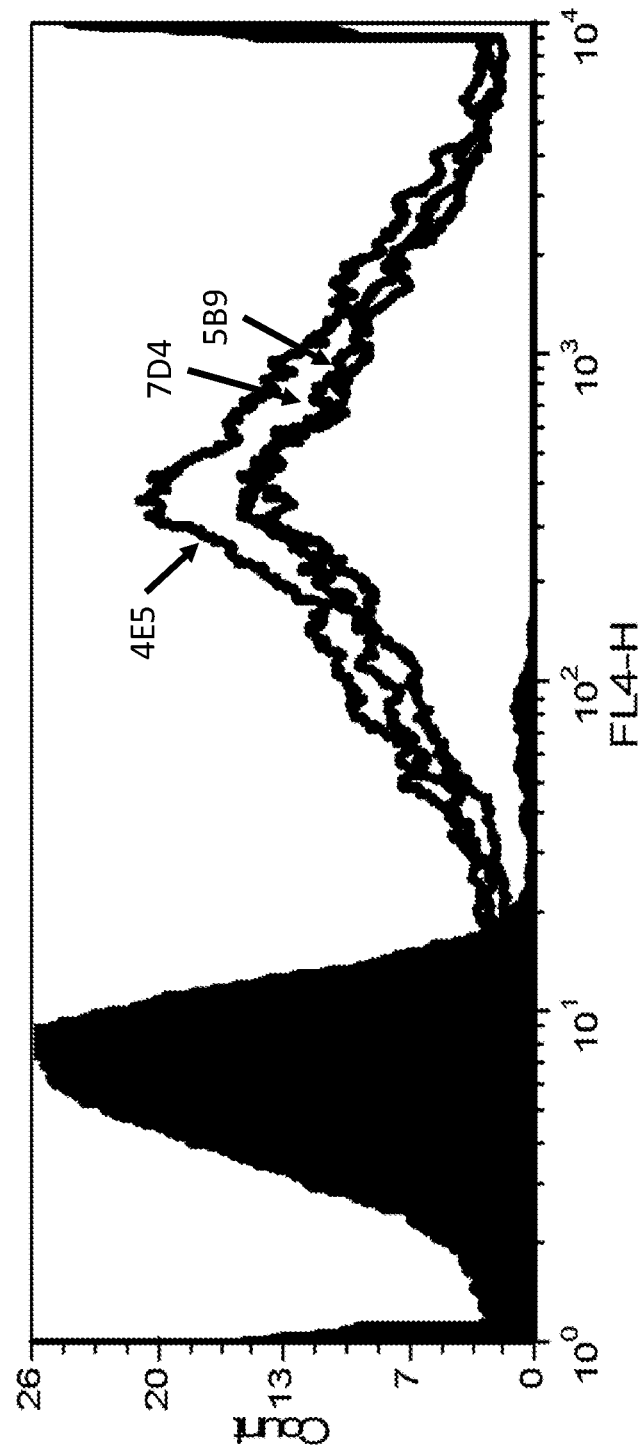
Figure 8C:
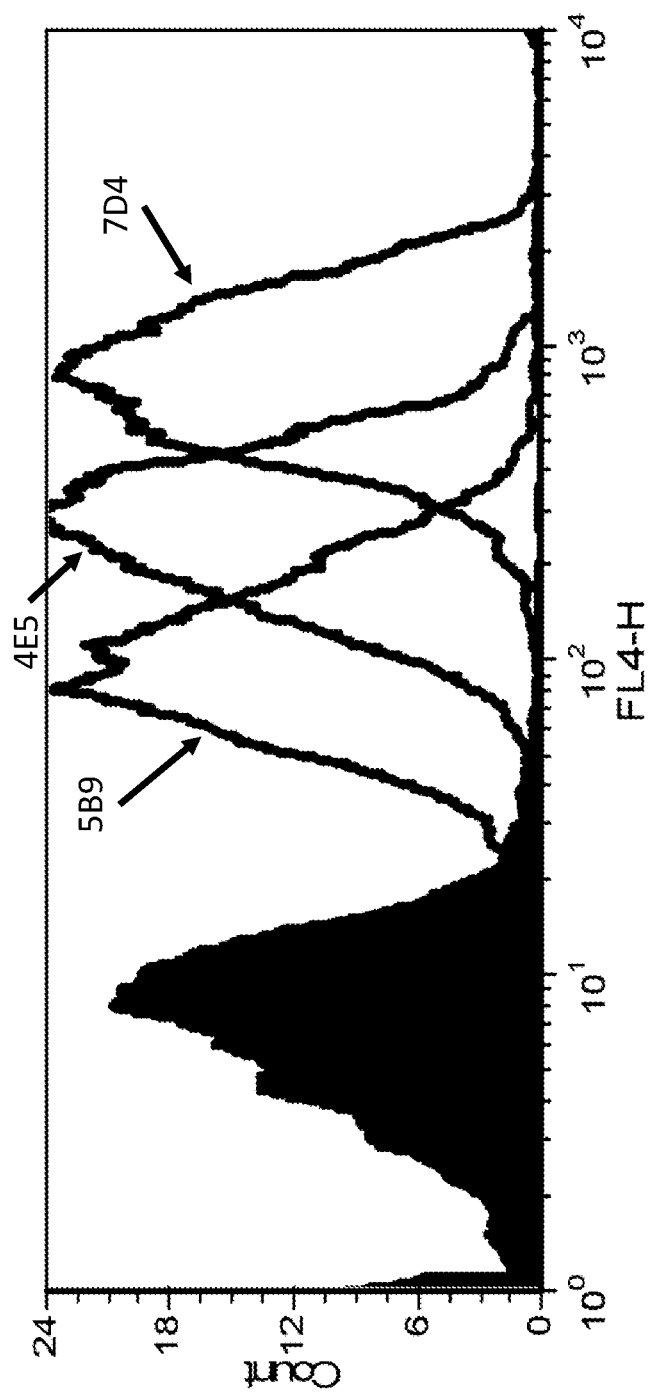

As shown in FIGS. 8A-C, all anti-PVR antibody clones tested bind to human PVR (hPVR), using FACS analysis. Briefly, cells were trypsinaized and transferred for staining at $2*10^5$ cell per well. Indicated antibodies were added for 30 min on ice. All antibodies were used at final concentration of 2 µg/ml. Bound anti-PVR Ab detection was performed using anti-mouse IgG-647. Mouse IgG1 kappa was used as a negative control.

FIG. 8A illustrates that endogenous hPVR was detected by FACS staining on the surface of HepG2 hepatocellular carcinoma cells. In FIG. 8B the murine cell line B16 was used. Murine PVR sequence is different from the human species and is not recognized by the anti-human PVR antibodies as can be seen by the lack of signal (left panel). When the full-length hPVR protein (NP_006496.4 amino acids 1-418) was overexpressed in these cells All three clones resulted in identical signal (right panel) further supporting the claim that this staining is the result of a specific binding of these Abs to the human PVR protein.

Figure 9:
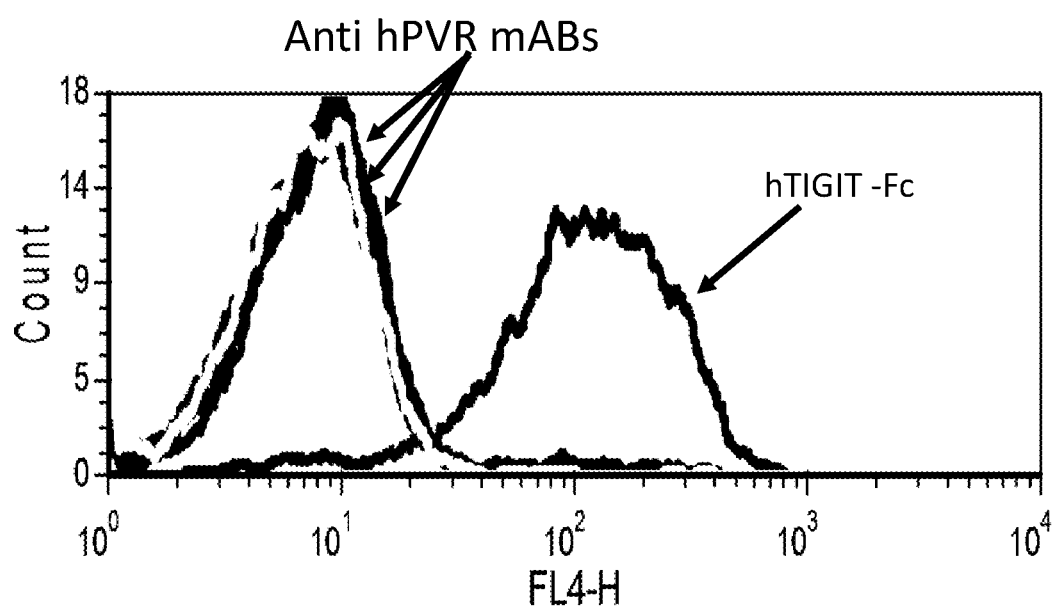
FIG. 9 is a graph depicting that the anti-PVR antibodies of the invention do not recognize canine PVR. Human TIGIT-Fc (10 µg/ml) is strongly cross-reactive and binds to the canine MDCK cell line. None of the PVR mAbs were able to bind to these cells suggesting that do not recognize the canine PVR.
Figure 10A:
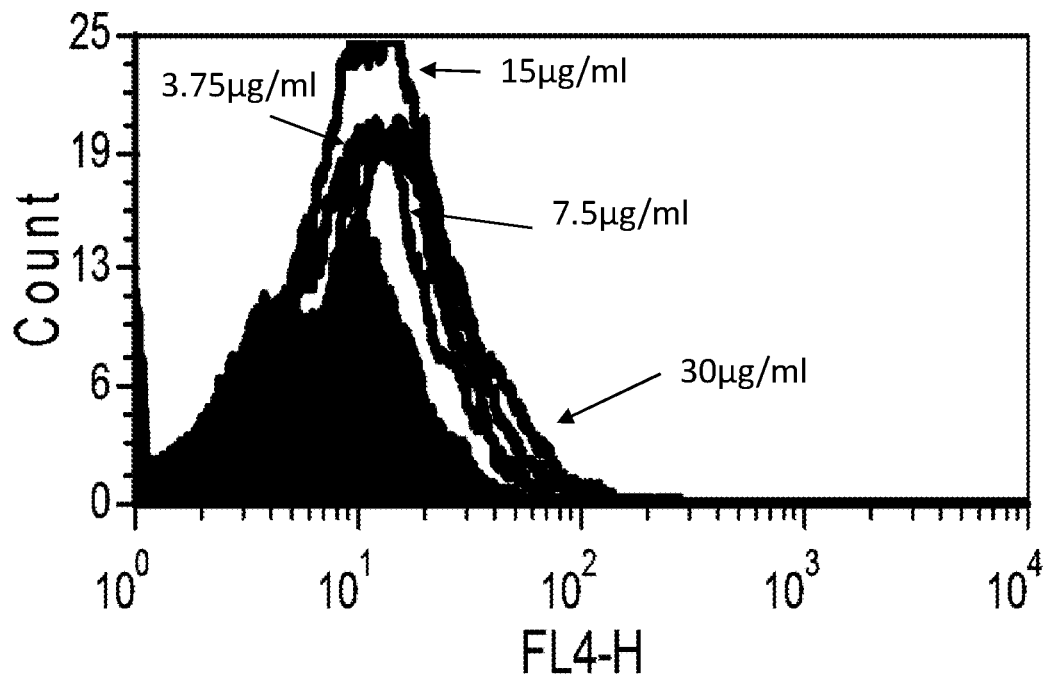
FIGS. 10A-10D depict that Nectin-2 is preferentially bound by DNAM-1 and not by TIGIT. Cells over expressing either PVR or Nectin2 were stained using the indicated antibody concentrations.
Figure 10B:
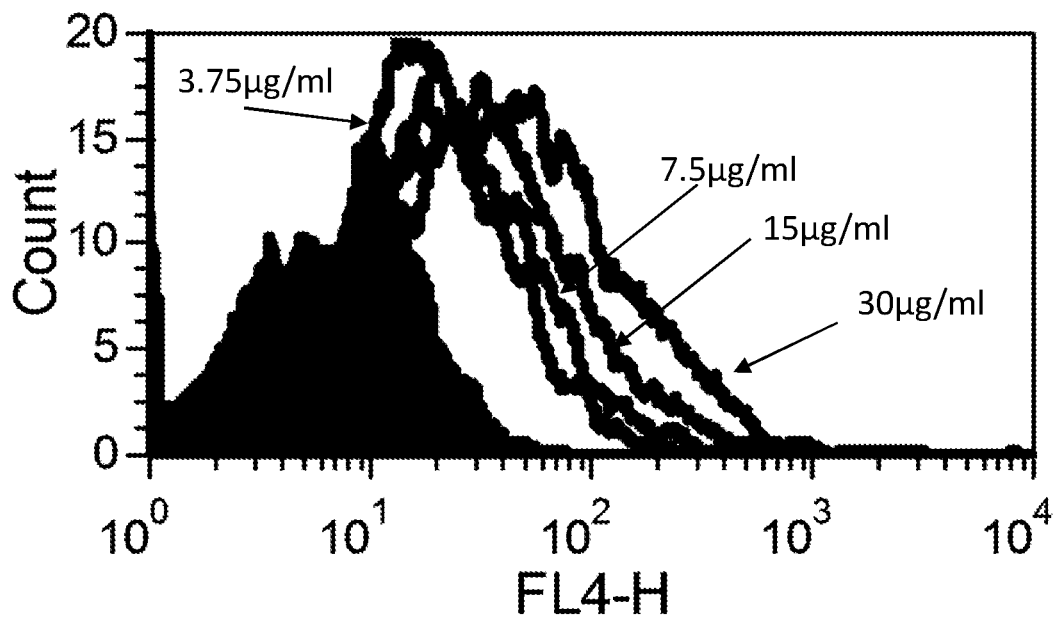
Figure 10C:
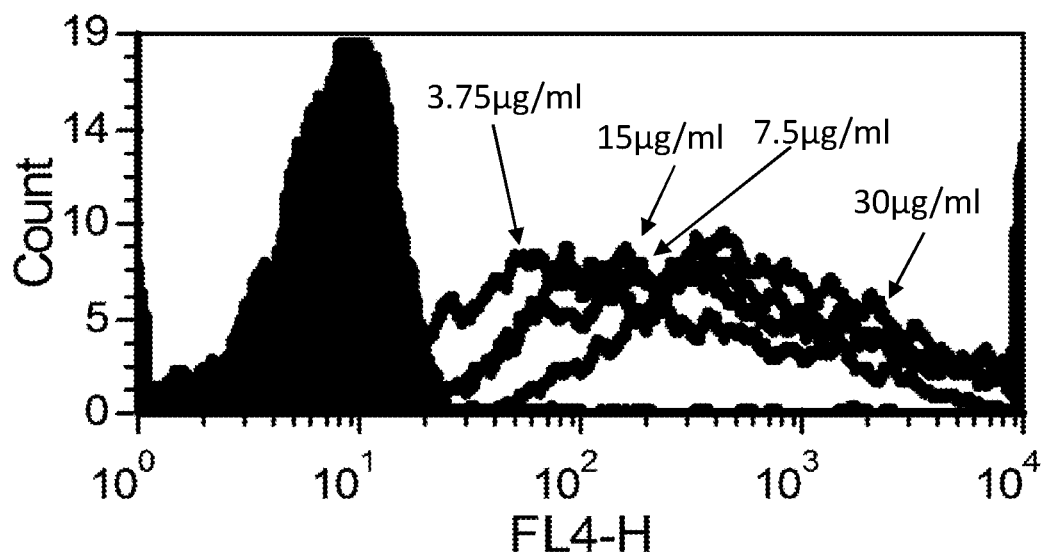
Figure 10D:
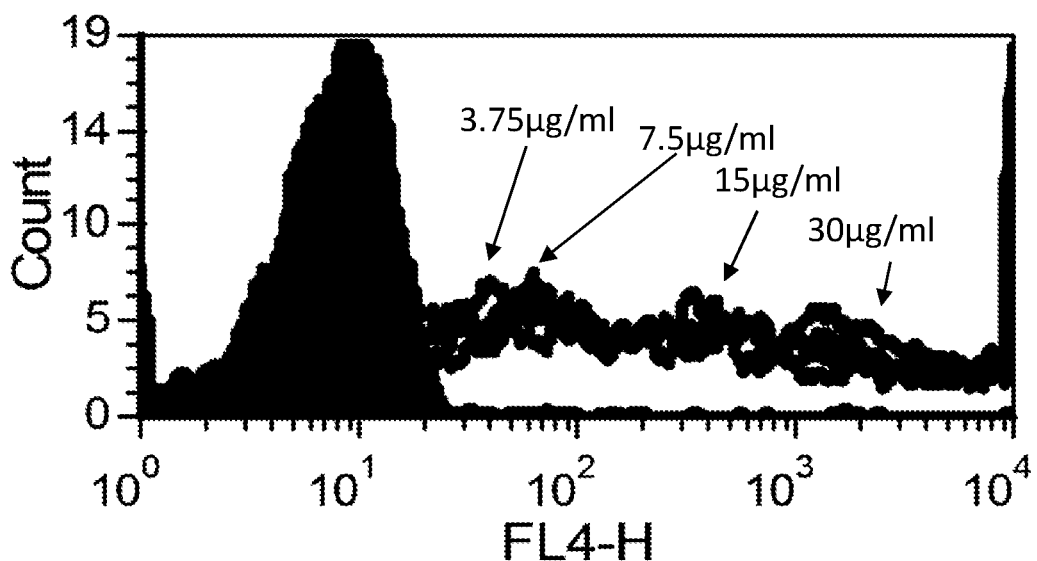

PVR amino acid sequence is conserved across some species. The amino acid conservation of human PVR was compared to that of African green monkeys in-silico and was found to have a similarity of 93% to human PVR. FACS staining of African green monkey Vero cells demonstrated that the monkey's PVR is efficiently recognized by all three human mAbs (FIG. 8C). It was further found that these human anti-PVR antibodies do not recognize PVR from canine and rodents such as hamster or mouse. FIG. 9 shows FACS analysis for the canine PVR expressing MDCK cells. As can be seen, none of the anti-human Abs resulted in a positive signal, while PVR expression itself is suggested by the strong TIGIT-Ig signal.

Example 8. Nectin-2 is Preferentially Bound by DNAM-1

TIGIT-Fc and DNAM-1-Fc were used at the indicated concentrations in FIG. 10 to stain cells overexpressing hNectin-2: RPMI-8866 cell line (FIGS. 10A and 10B), (or B16-hPVR cell line (FIGS. 10C and 10D). Bound fusion protein detection was made using anti-human-IgG APC and analyzed by FACS.

For the PVR binding the signal by TIGIT-Fc was 2-4 folds higher than that of the DNAM-1-Fc, similarly to a previous report (Yu. X et al., 2009, Nat Immunol., 10(1):48-57). At the same time, the binding of hNectin-2 to DNAM-1-Fc was 2-10 folds stronger than its binding to TIGIT-Fc, which is contradictory to one report (Yu. X et al 2009), but corroborated by another study (Zhu Y et al., 2016, J Exp Med., 8; 213(2):167-76). Taken together, the results illustrate that DNAM-1 is the preferential receptor for Nectin-2 binding. Accordingly, blocking of PVR will prevent the inhibitory signaling of TIGIT, while allowing the co-stimulatory signaling by DNAM-1. DNAM-1 mediates cellular adhesion to other cells bearing its ligands.

Example 9. Anti PVR Antibodies Enhance T Cell Proliferation

Figure 11:
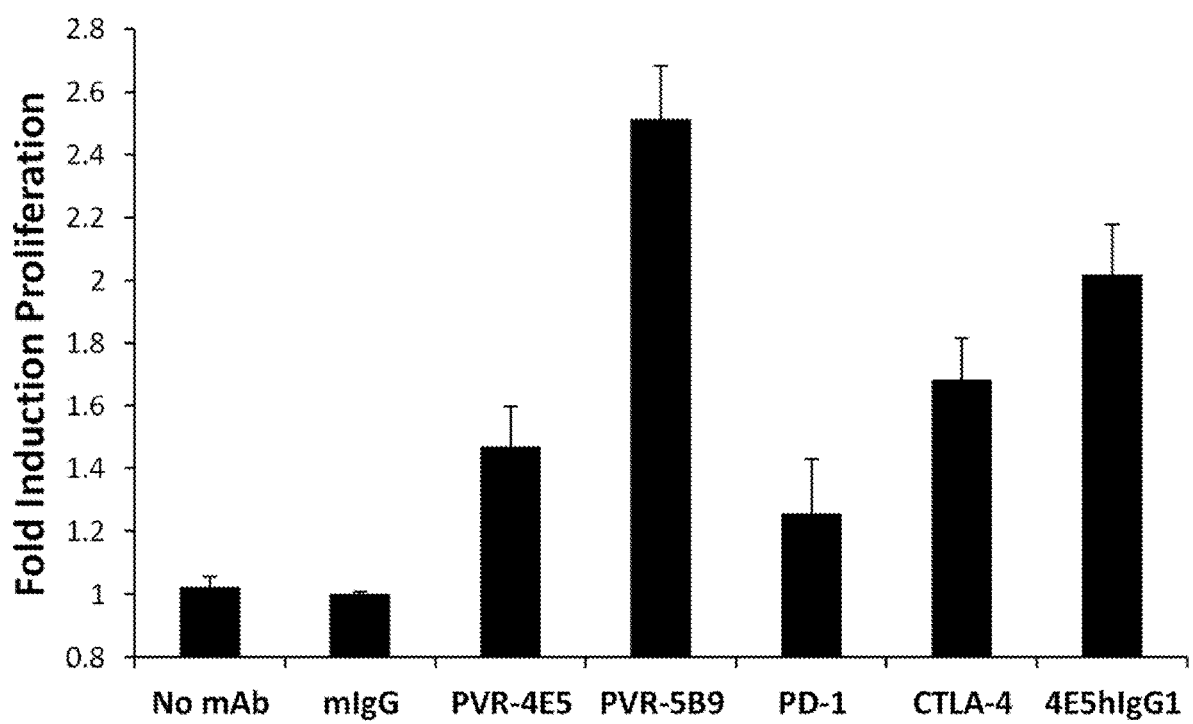
FIG. 11 shows the effect of anti-PVR antibodies on T cell proliferation. Human PBMCs were CFSE labeled and incubated with target cells in the presence of the indicated antibodies. Results are presented as fold increased proliferation relative to the control. The results are of pooled 7 experiments total of 10 healthy donors. P values: for mAb 4E5—0.000241, for mAb 5B9—$1.96E^{-05}$, for anti PD-1—0.016303, for anti CTLA4—0.000171, and for 4E5hIgG1—0.008176.
Figure 12:
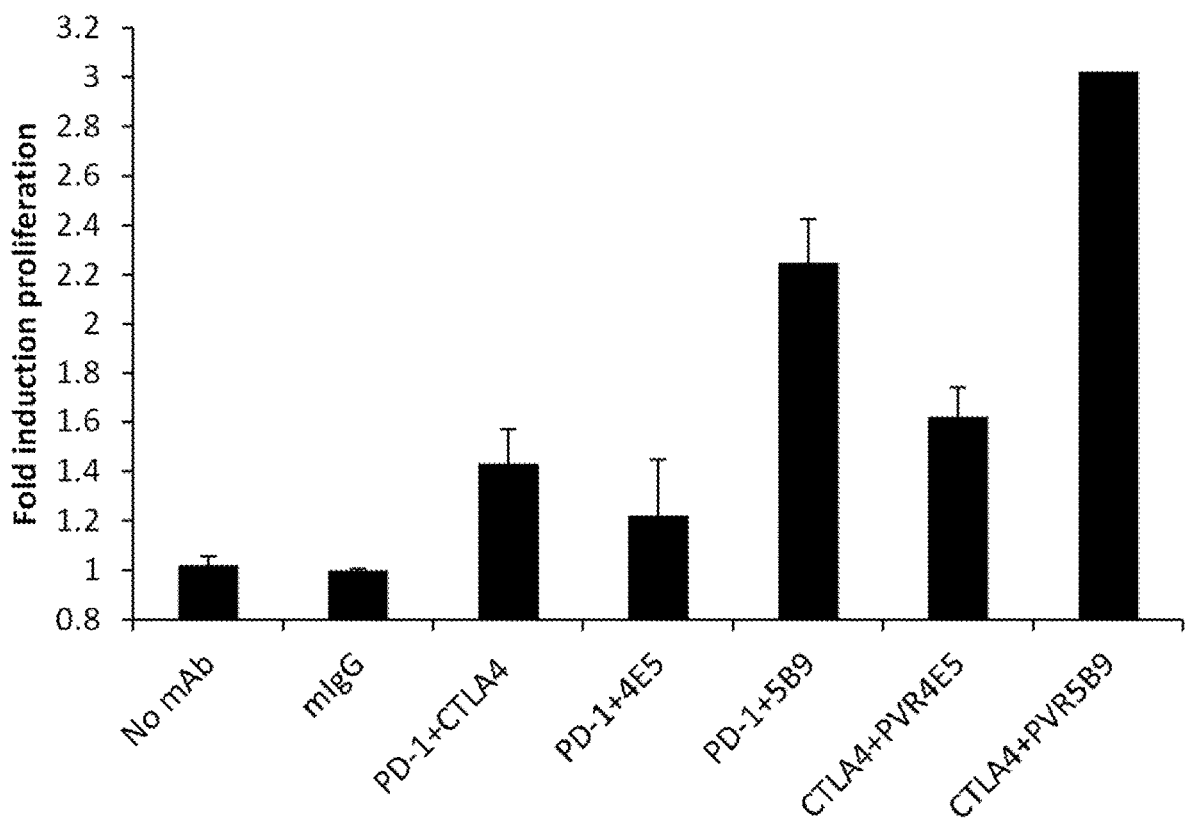
FIG. 12 shows the combined effect of anti-PVR antibodies and other antibodies on T cell proliferation. Human PBMCs were CFSE labeled and incubated with target cells in the presence of the indicated combination of antibodies. Results are presented as fold increased proliferation relative to the control. The results are 7 independent experiments using 12 healthy donors. P. Values: anti PD1+anti CTLA—47.54E$^{-03}$, anti PD-1+4E5—7.02E$^{-02}$, anti PD-1+5B9—1.11E$^{-04}$, anti CTLA4+4E5—1.37E$^{-03}$, anti CTLA4+5B9—5.47E$^{-06}$.
Figure 13:
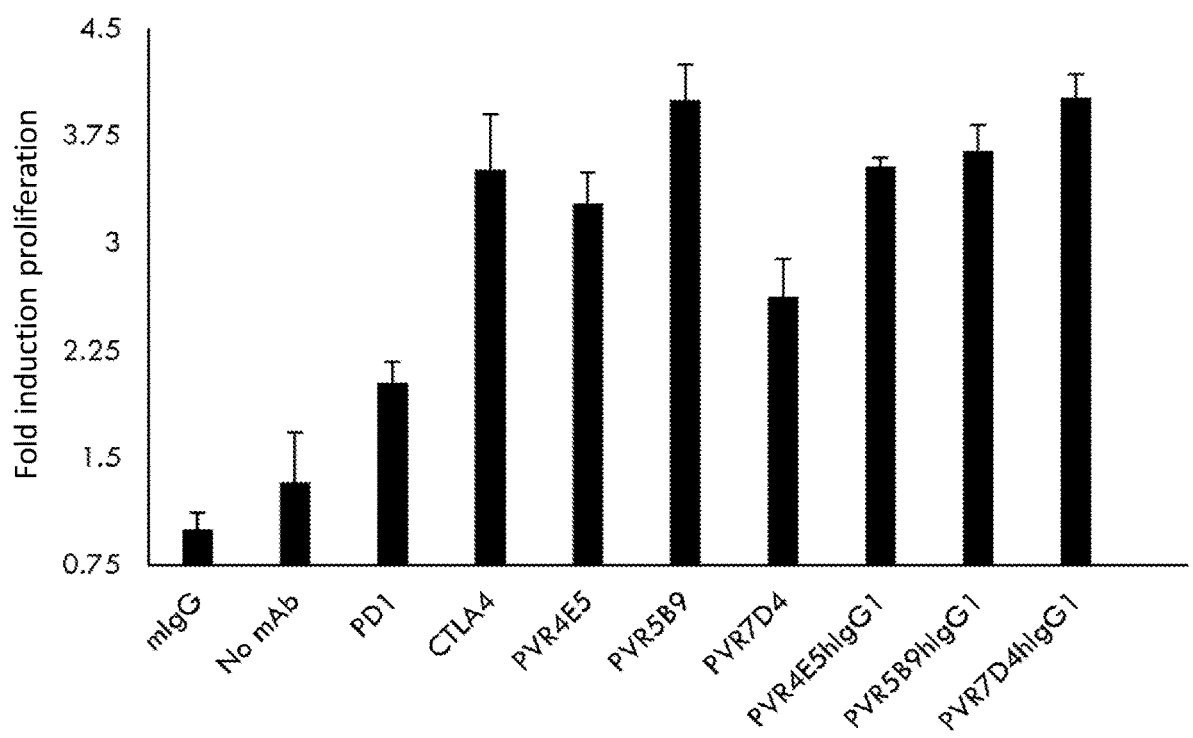
FIG. 13 depicts the specific effect of anti-PVR antibodies on CD8 T cell proliferation. Human PBMCs were CFSE labeled and incubated with target cells (A549) in the presence of the indicated antibodies. CD8 positive cells were count by FACS after 9-12 days in culture. Results are presented as fold increased proliferation relative to the control. The results are of 2 independent experiments using healthy PBMC donors.
Figure 14:
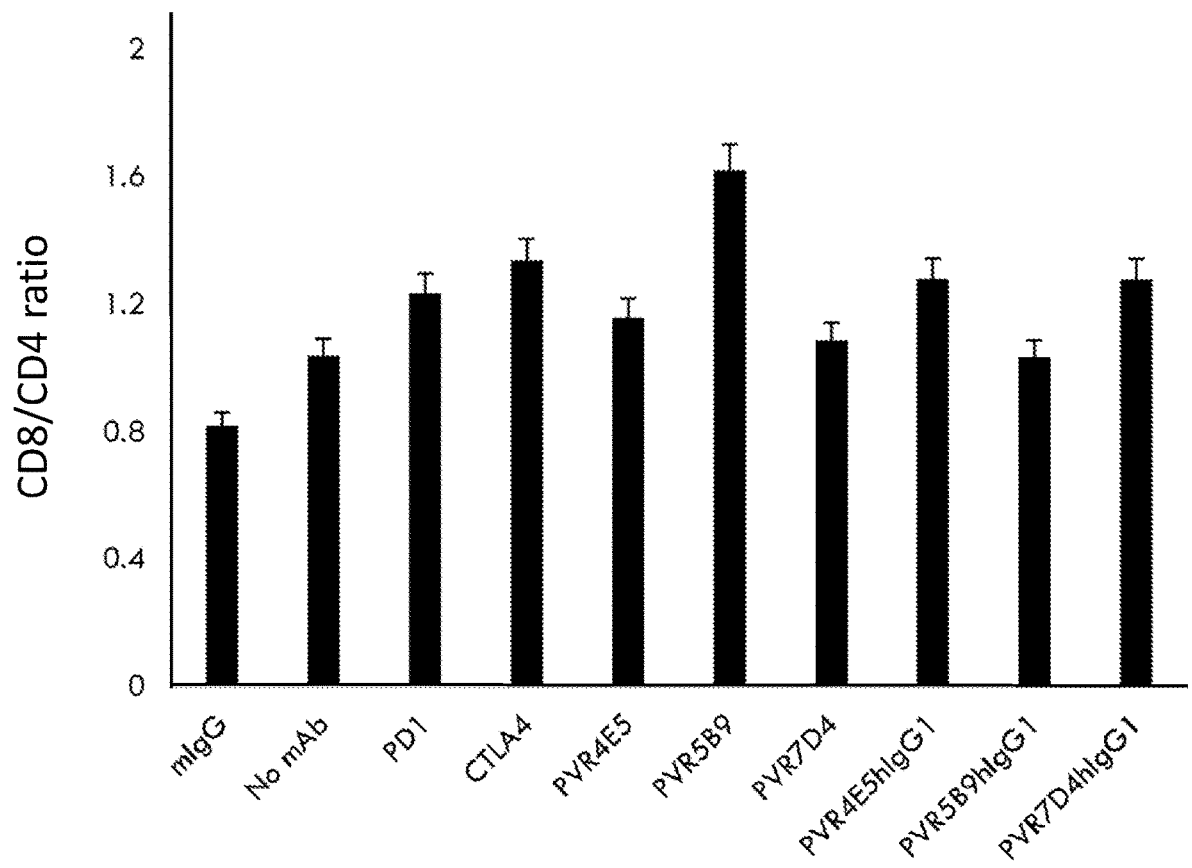
FIG. 14 depicts the ratio of CD8 cells to CD4 cells following the induction with different antibodies. Human PBMCs were CFSE labeled and incubated with target cells (A549) in the presence of the indicated antibodies. Cells were counted after 9-12 days in culture. The results are of pooled 2 experiments total of 2 healthy donors.

To test the effect of the anti PVR mAbs on T cell proliferation, human peripheral blood mononuclear cell (PBMC) were stained with carboxyfluorescein succinimidyl ester (CFSE) and incubated with target cells in the present of antibodies at a concentration of 4 µg/ml. CFSE dilution was measured on CD45 positive cells after 5-9 days in culture. As shown in FIG. 11, Anti PVR 5B9 activity exceeds the PD-1 and CTLA4 antibodies activity as a single agent. Also, chimeric anti PVR 4E5hIgG1 clone, having a human IgG1 constant region, was superior to its mouse counterpart. Next, the combined effect of anti PVR mAbs and other antibodies that were found to enhance T cell proliferation was examined. Human PBMC were stained with Carboxyfluorescein succinimidyl ester (CFSE) and incubated with target cells in the present of antibodies at a concentration of 4 µg/ml. CFSE dilution was measured on CD45 positive cells after 5-9 days in culture. The results show that the proliferation activity of anti-PVR 5B9, when combined with either PD-1 or CTLA-4, exceeds the activity of a combination of PD-1 and CTLA4 (FIG. 12). Also, the activity of a combination of anti-PVR 4E5 and CTLA-4 equals PD-1 and CTLA4 combination. Next, the specific induction of CD8 was examined. As shown in FIG. 13, Anti PVR antibodies CD8 T cell proliferation activity exceeds the activity of PD1. Also, the induction activity of anti PVR 5B9 antibody exceeds that of CTLA1. The ratio of CD8/CD4 proliferation was evaluated for the different antibodies (FIG. 14). Anti PVR 5B9 had the highest CD8/CD4 ratio. The DNA sequence of the variable heavy and light chains were used to construct chimeric antibodies, comprising the human IgG1 isotype constant domains and constant light (CL) human IgG Kappa domain. T-cell proliferation induced by mouse and human chimeric counterpart antibodies was measured by the CFSE assay. The numbers shown in Table 2 represent relative level of proliferation compared to control.

TABLE 2

A summary of the effect of anti PVR antibodies on T cell proliferation.

| Name of clone | Fc Type | Effect on T cell proliferation (CFSE) | Effect on T cell proliferation cell count |
|---|---|---|---|
| 4E5 | Mouse IgG1 | 198% | 320% |
|  | Human IgG1 | 275% | 353% |
| 5B9 | Mouse IgG1 | 300% | 410% |
|  | Human IgG1 | 270% | 364% |
| 7D4 | Mouse IgG1 | 141% | 260% |
|  | Human IgG1 | 280% | 360% |

Next, the PVR-antibodies effect on NK degranulation was examined. During degranulation, cytolytic granules in NK cells are released and the lysosome-associated membrane protein-1 (LAMP-1, CD107a) which is present on cytolytic granules surface is transported to the cell surface and becomes accessible for antibody binding. This marker allows identification of activated NK cells. NK cells were incubated with 5 different target cells, together with the anti PVR antibodies (mouse and their chimeric human counterpart antibodies). Degranulation was evaluated using anti-CD107a antibodies.

TABLE 3

Effect of anti-PVR antibodies on NK degranulation activity.

| | | Target cancer cells | | | | |
|---|---|---|---|---|---|---|
| Clone | Fc Type | MDA-MB-231 | HepG2 | MV-411 | Mel-624* | A549 |
| 4E5 | Mouse IgG1 | 125% | 150% | 150% | 120% | — |
|  | Human IgG1 | 305% | 260% | 160% | 145% | 260% |
| 5B9 | Mouse IgG1 | 132% | 160% | 150% | 120% | — |
|  | Human IgG1 | 300% | 260% | 220% | 145% | 240% |
| 7D4 | Mouse IgG1 | 124% | 160% | 150% | 115% | — |
|  | Human IgG1 | 220% | 200% | 130% | 120% | 165% |

*Expression of hPVR in Mel 624 is low therefore the relative effect is low.

Figure 15:
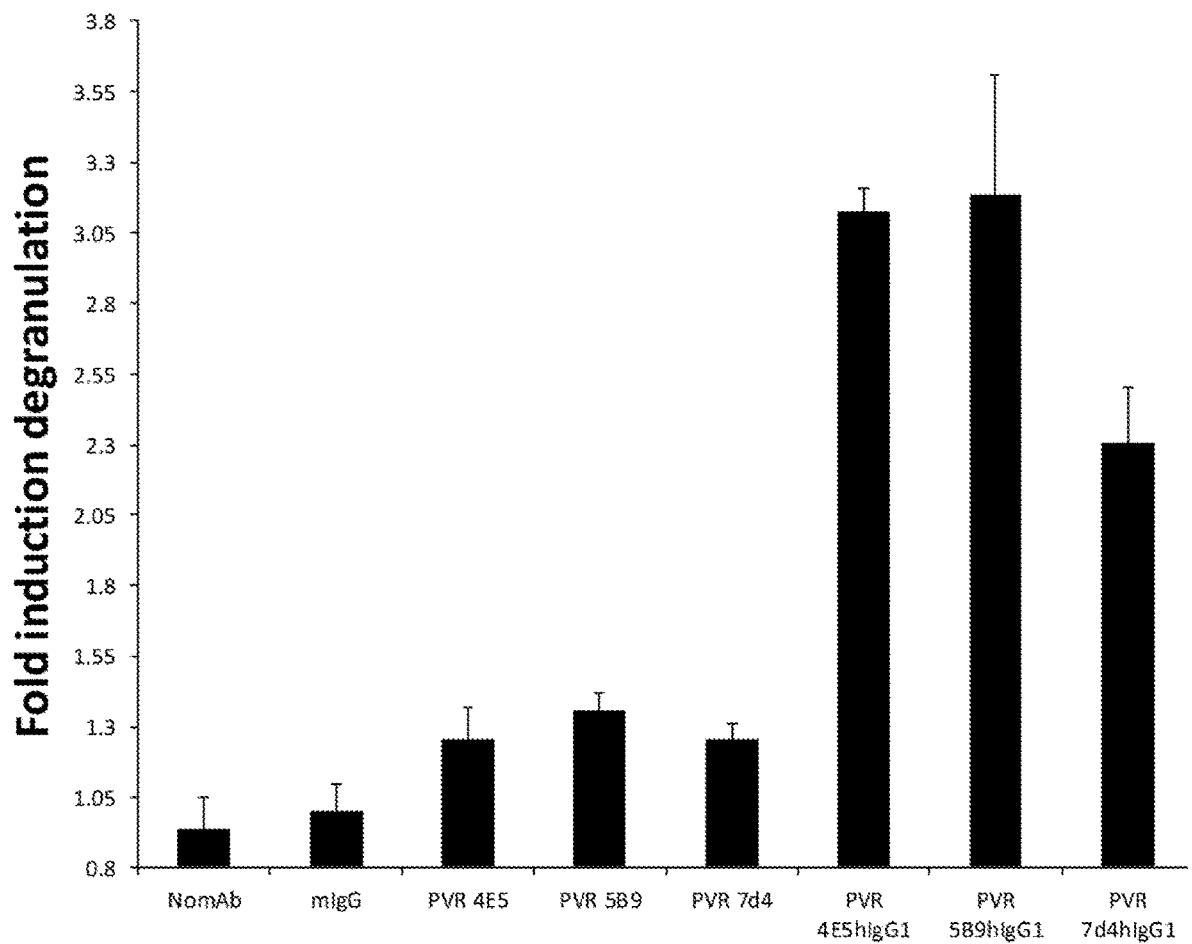
FIG. 15 shows the effect of anti-PVR antibodies on NK degranulation. Human NK cells were incubated with MDA-MB-231 cells (triple negative breast cancer cell line) in the presence of the indicated antibodies. The results are representative of 7 independent experiments done with 5 different healthy NK cell donors. P values: PVR4E5—0.005063, PVR5B9—0.00374, PVR7D4—0.019448, PVR4E5—hIgG1—2.03E$^{-05}$, PVR5B9-hIgG1—1.45E$^{-05}$, PVR7D4-hIgG1 5.8E$^{-05}$.
Figure 16A:
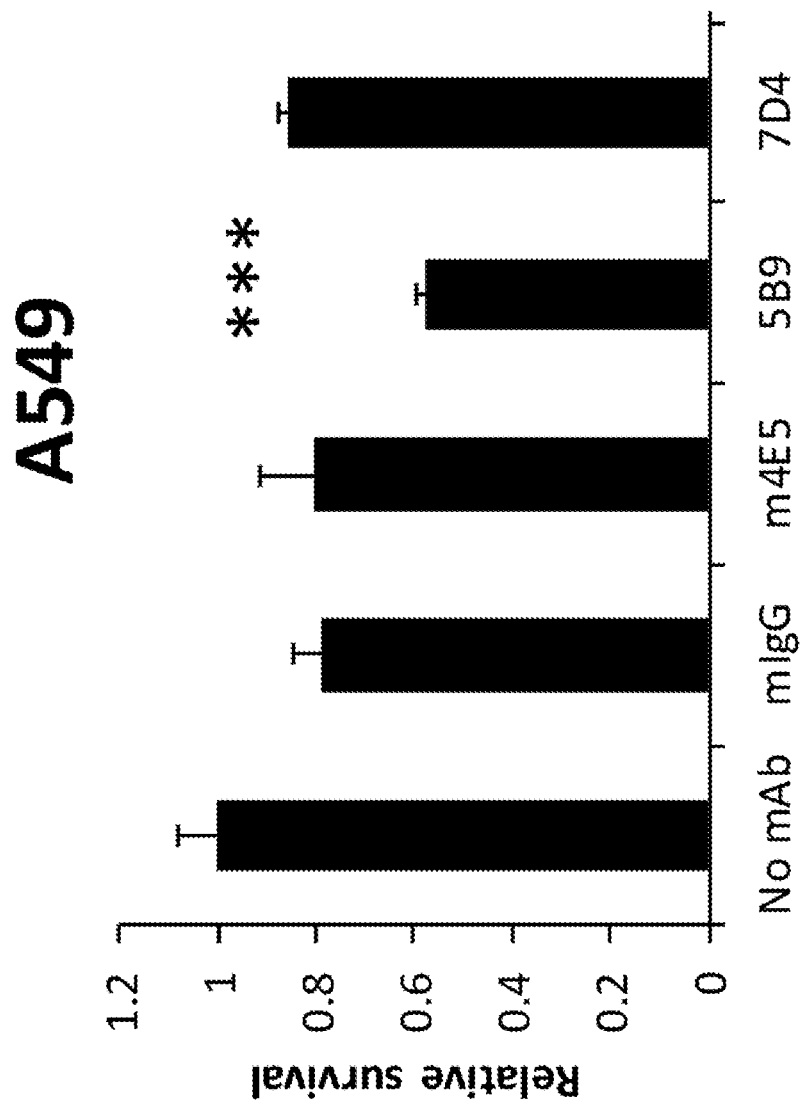
FIGS. 16A-16D shows the effect of the anti-PVR antibodies on tumor cell survival in the absence of immune cells. The survival of A549 cells (FIG. 16A), U373 cells (FIG. 16B), HCT116 cells (FIG. 16C), and Mel-624 (FIG. 16D) was examined using MTT cell survival assay in the presence of 50 microgram/ml of the indicated mAb for 24 hours. Significance is calculated by a single tailed Student TTEST, *<0.05, <0.03, and *<0.02.
Figure 16B:
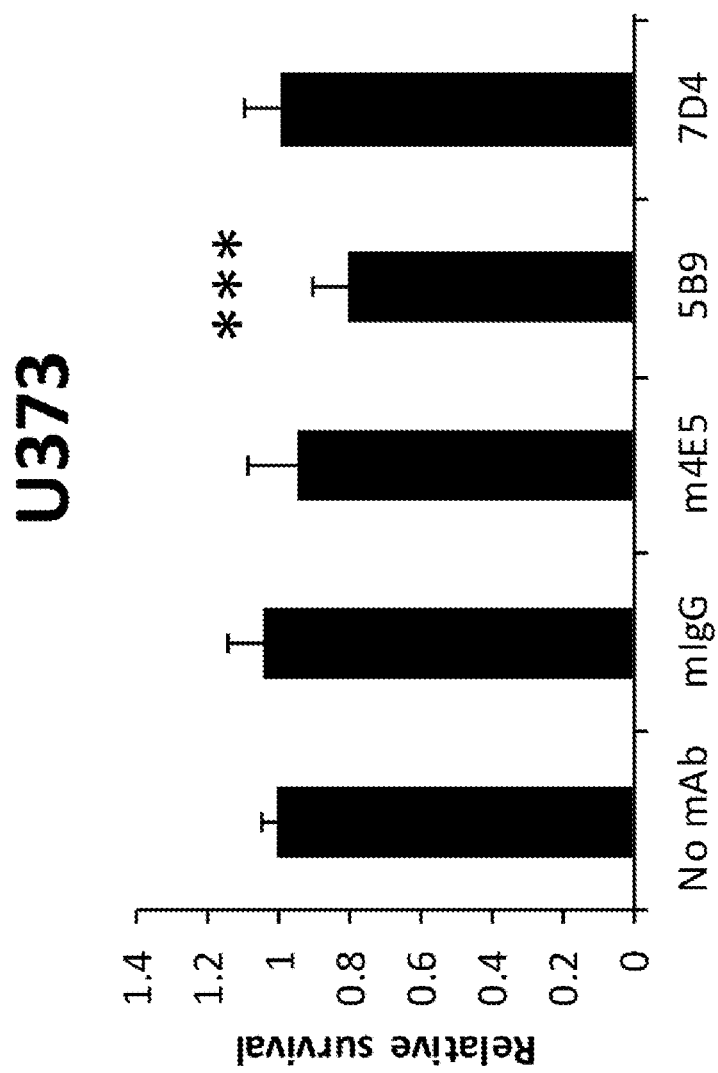
Figure 16C:
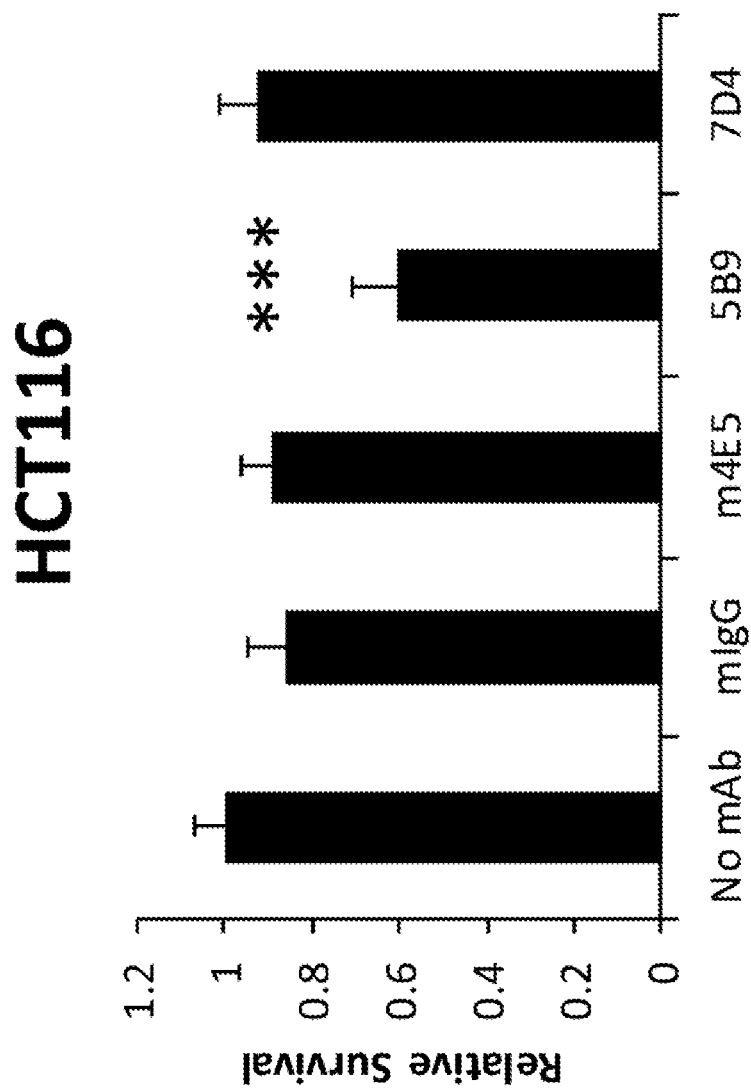
Figure 16D:
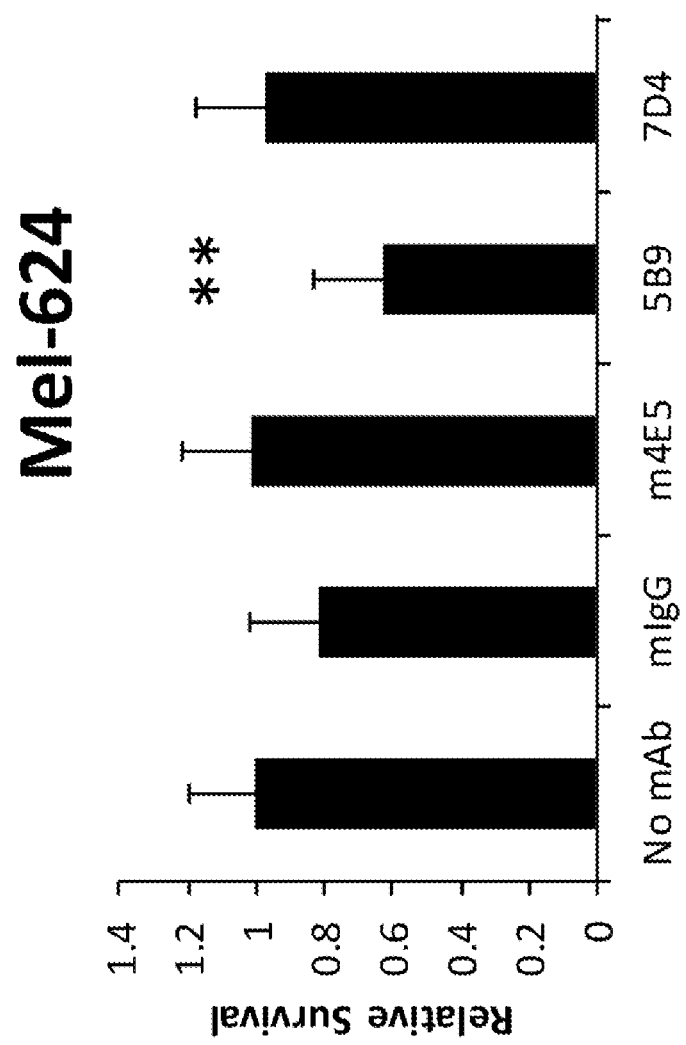

As shown in Table 3 and FIG. 15, all antibodies showed an NK degranulation activity, wherein the chimeric antibodies had a significantly higher activity compared to their corresponded mouse antibody.

Example 10. Anti PVR Antibodies Reduce the Survival of Tumor Cells in the Absence of Immune Cells The survival of A549, U373, HCT116, and Mel-624 cells was examined using MTT cell survival assay in the presence of 50 microgram/ml of different anti-PVR mAb for 24 hours. As shown in FIGS. 16A-16D and Table 4, PVR blocking by 5B9 mAb significantly reduced viability of 20-40% compared to mIgG.

TABLE 4

Effect of anti-PVR antibodies on survival of tumor cells.
Percentage of dead cells within 24 hrs across several target cell lines relative to mIgG treated cells.

| mAb | MDA-MB-231 | HCT-116 | Mel-624 | A549 |
|---|---|---|---|---|
| 4E5 | 12% | 20% | — | 25% |
| 5B9 | 20% | 22% | 32% | 25% |
| 7D4 | 17% | 27% | 12% | 25% |

Example 11. In-Vivo Effect of Anti-PVR Antibodies on Human Tumor in a Humanized Mouse Model—Short Term Humanization The anti-tumor efficacy of the antibodies is studied in vivo. To estimate the efficacy of the antibodies described herein in inhibition of human cancer, the antibody is studied in a model combining both tumors and lymphocytes of human origin. NOD scid gamma (NSG) mice are engrafted with hPBMCs to restore immune-competence and challenged with human cancer cells. At predetermined time point/tumor size mice are treated with anti human PVR antibody according to the invention, administered in multiple doses at different time-points post tumor challenge. Same experiments are performed with chimeric anti-PVR antibodies. Tumor growth curves and body weight are measured 3x/week and upon sacrificing the mice, extensive phenotypic analysis of TILs and immune populations in different organs is performed.

A similar model with tumor lines in PBMC huNSG mice is performed according to Gupta P., Oncoimmunology. 2015 Mar. 6; 4(2): e981449.

Example 12. In-Vivo Effect of Anti-PVR Antibodies on Human Tumor in a Humanized Mouse Model—Long Term Humanization To estimate the efficacy of anti-PVR antibodies in inhibition of human cancer, the antibody is studied in a model combining both tumors and lymphocytes of human origin. Newborn NOD scid gamma (NSG) pups are irradiated and engrafted with CD34+HSC to restore immune-competence. 1-2 weeks after determination of immune cells reconstitution, mice are challenged with human cancer cells and at predetermined time point/tumor size treated anti human PVR antibody according to the invention, administered in multiple doses on different time points. Same experiments are performed with humanized anti-PVR antibodies. Tumor growth curves and body weight are measured 3x/week. Upon sacrificing the mice, extensive phenotypic analysis of TILs and immune populations in different organs is performed.

A similar model used to study the tumor inhibitory activity of the antibodies of the present invention, was established by The Jackson Laboratory (http://immune-checkpoint.com/wp-content/uploads/sites/24/2015/01/Day-1-15.45-Rick-Huntress.pdf).

Example 13. Induction of IFNγ Secretion

To test the effect of the anti PVR mAbs on cytokine secretion, human peripheral blood mononuclear cell (PBMC) from 2 healthy donors were incubated with target cells in the present of antibodies (mIgG, 5B9mIgG, anti CTL-4 antibody termed Ipilimumab), at concentrations of 1 and 0.1 µg/ml. Levels of IFNγ after 6 days in culture were measured. Significant induction of IFNγ by the anti-PVR 5B9 antibody was observed (P=7.34548E$^{11}$ for 1 µg/ml and 2.73179E$^{-08}$ for 0.1 µg/ml).

The secretion of IFNγ is a key component of anti-tumor immunity, induction of IFNγ secretion by anti-PVR mAbs indicates potential additional anti-tumorigenic effect of these compounds in cancer treatment.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

The invention claimed is:

1. An isolated monoclonal antibody or an antibody fragment, comprising a CDR set, the CDR set comprising a heavy chain (HC) CDR1, a heavy chain (HC) CDR2, a heavy chain (HC) CDR3, a light chain (LC) CDR1, a light chain (LC) CDR2, and a light chain (LC) CDR3 selected from the group consisting of:
   i. the HC CDR1 sequence comprises a sequence selected from the group consisting of GYTFSNYWIE (SEQ ID NO: 36) and SNYWIE (SEQ ID NO: 84); the HC CDR2 sequence comprises EIFPGSGRINFNEKFKG (SEQ ID NO: 38); the HC CDR3 sequence comprises TKIYGNSFDY (SEQ ID NO: 40); the LC CDR1 comprises a sequence selected from the group consisting of KASQDVGTAVV (SEQ ID NO: 44) and KASQDVGTAV (SEQ ID NO: 85); the LC CDR2 sequence comprises a sequence selected from the group consisting of: WASSRHN (SEQ ID NO: 46), WASSRHA (SEQ ID NO: 56), WASSRHR (SEQ ID NO: 57), WASSRHD (SEQ ID NO: 58), WASSRHE (SEQ ID NO: 59), WASSRHP (SEQ ID NO: 60), and WASSRHT (SEQ ID NO: 61); and the LC CDR3 sequence comprises QQYSRYPLT (SEQ ID NO: 48);
   ii. the HC CDR1 sequence comprises a sequence selected from the group consisting of GFDFSRYW (SEQ ID NO: 4) and RYWMT (SEQ ID NO: 80); the HC CDR2 sequence comprises a sequence selected from the group consisting of EIHPDSSKINYTPSQ (SEQ ID NO: 6) and EIHPDSSKINYTPSQKD (SEQ ID NO: 81); the HC CDR3 sequence comprises a sequence selected from the group consisting of PDGNYNALDYW (SEQ ID NO: 8) and PDGNYNALDY (SEQ ID NO: 82); the LC CDR1 sequence comprises KASQDVGTAVT (SEQ ID NO: 12); LC CDR2 is WASTRHT (SEQ ID NO: 14); and the LC CDR3 sequence comprises QQYSRYPYT (SEQ ID NO: 16); and
   iii. the HC CDR1 sequence comprises a sequence selected from the group consisting of GYTFTEYTMH (SEQ ID NO: 20) and EYTMH (SEQ ID NO: 83); the HC CDR2 sequence comprises GIDPNNGGTNYNQNFKG (SEQ ID NO: 22); the HC CDR3 sequence comprises VIPLEY (SEQ ID NO: 24); the LC CDR1 sequence comprises KASQNVYTNVA (SEQ ID NO: 28); the LC CDR2 sequence comprises SASYRYR (SEQ ID NO: 30); and the LC CDR3 sequence comprises QQYNSYPLA (SEQ ID NO: 32).

2. The isolated monoclonal antibody or the antibody fragment of claim 1, wherein the HC CDR1 comprises the sequence SNYWIE (SEQ ID NO: 84); HC CDR2 comprises a sequence set forth in EIFPGSGRINFNEKFKG (SEQ ID NO: 38); and HC CDR3 comprises the sequence: TKIYGNSFDY (SEQ ID NO: 40).

3. The isolated monoclonal antibody or the antibody fragment of claim 1, wherein the HC CDR1 sequence comprises GYTFSNYWIE (SEQ ID NO: 36); the HC CDR2 sequence comprises EIFPGSGRINFNEKFKG (SEQ ID NO: 38); the HC CDR3 comprises TKIYGNSFDY (SEQ ID NO: 40); the LC CDR1 sequence comprises KASQDVGTAVV (SEQ ID NO: 44); the LC CDR2 sequence comprises WASSRHE (SEQ ID NO: 59); and the LC CDR3 sequence comprises QQYSRYPLT (SEQ ID NO: 48).

4. The isolated monoclonal antibody or the antibody fragment of claim 1, wherein the HC CDR1 sequence comprises a sequence selected from the group consisting of GYTFSNYWIE (SEQ ID NO: 36) and SNYWIE (SEQ ID NO: 84); the HC CDR2 sequence comprises EIFPGSGRINFNEKFKG (SEQ ID NO: 38); the HC CDR3 sequence comprises TKIYGNSFDY (SEQ ID NO: 40); the LC CDR1 sequence comprises a sequence selected from the group consisting of KASQDVGTAVV (SEQ ID NO: 44) and KASQDVGTAV (SEQ ID NO: 85); the LC CDR2 sequence comprises WASSRHE (SEQ ID NO: 59; and LC CDR3 sequence comprises QQYSRYPLT (SEQ ID NO: 48).

5. The isolated monoclonal antibody of claim 1 capable of inhibit binding of PVR to T cell immunoreceptor with Ig and ITIM domains (TIGIT).

6. A polynucleotide sequence encoding at least one region of a HC or a LC sequence of a monoclonal antibody or antibody fragment of claim 1.

7. A plasmid comprising at least one polynucleotide sequence of claim 6.

8. A hybridoma cell comprising a polynucleotide sequence of claim 6.

9. The monoclonal antibody of claim 1 attached to a cytotoxic moiety, a radioactive moiety, or an identifiable moiety.

10. A pharmaceutical composition comprising as an active ingredient, at least one isolated antibody or fragment thereof, of claim 1 and a pharmaceutical acceptable excipient, diluent, salt or carrier.

11. The pharmaceutical composition of claim 10 for use in modulating the immune system activity by inhibiting binding of PVR to TIGIT.

* * * * *